(12) United States Patent
Wandinger-Ness et al.

(10) Patent No.: US 8,765,803 B1
(45) Date of Patent: Jul. 1, 2014

(54) RAB7 GTPASE INHIBITORS AND RELATED METHODS OF TREATMENT

(75) Inventors: Angela Wandinger-Ness, Albuquerque, NM (US); Larry Sklar, Albuquerque, NM (US); Jacob Agola, Albuquerque, NM (US); Zurab Surviladze, Albuquerque, NM (US); Jeffrey Aubé, Lawrence, KS (US); Jennifer Golden, Olathe, KS (US); Chad E. Schroeder, Lawrence, KS (US); Denise S. Simpson, Lawrence, KS (US)

(73) Assignees: STC.UNM, Albuquerque, NM (US); University of Kansas, Lawrence, KS (US)

( * ) Notice: Subject to any disclaimer, the term of this patent is extended or adjusted under 35 U.S.C. 154(b) by 3 days.

(21) Appl. No.: 13/404,921

(22) Filed: Feb. 24, 2012

Related U.S. Application Data

(60) Provisional application No. 61/464,271, filed on Mar. 2, 2011.

(51) Int. Cl.
*A01N 43/10* (2006.01)
*A01N 43/16* (2006.01)

(52) U.S. Cl.
USPC ........................................ 514/443; 514/453

(58) Field of Classification Search
None
See application file for complete search history.

(56) References Cited

PUBLICATIONS

Edinger et al. Developmental Cell 5, p. 571-582, 2003.*
Spinosa et al. The Journal of Neuroscience, 28(7), 1640-1648, 2008.*
East M. P. , R. A. Kahn, Semin Cell Dev Biol (2010) e-pub; 22,3-9 (2011).
Gillingham A. K. , S. Munro, Annu Rev Cell Dev Biol 23, 579 (2007).
Jaffe A. B. , A. Hall, Annu Rev Cell Dev Biol 21, 247 (2005).
Mitra S. , K. W. Cheng, G. B. Mills, Semin Cell Dev Biol (2010) e-pub; 22,57-68 (2011).
Parri M. , P. Chiarugi, Cell Commun Signal 8, 23 (2010).
Stein M. P. , J. Dong, A. Wandinger-Ness, Adv Drug Deliv Rev 55, 1421 (2003).
Grant B. J. , A. A. Gorfe, J. A. McCammon, PLoS Comput Biol 5, e1000325 (2009).
Bos J. L. , H. Rehmann, A. Wittinghofer, Cell 129, 865 (2007).
Barr F. , D. G. Lambright, Curr Opin Cell Biol 22, 461 (2010).
Sebti S. M. , A. D. Hamilton, Oncogene 19, 6584 (2000).
Sousa S. F. , P. A. Fernandes, M. J. Ramos, Curr Med Chem 15, 1478 (2008).
Sane K. M. et al., J Pharmacol Exp Ther 333, 23 (2010).
Machida S. , N. Kato, K. Harada, J. Ohkanda, J Am Chem Soc (2010) e-pub; 133,958-963 (2011).

(Continued)

*Primary Examiner* — Nissa Westerberg
(74) *Attorney, Agent, or Firm* — Henry D. Coleman; R. Neil Sudol

(57) ABSTRACT

This invention relates to compounds and their use as inhibitors or activators of Rab7 GTPase to treat or prevent the onset of Rab 7 GTPase-associated disorders such as neuropathies, cancer, metabolic diseases of bone and lipid storage. The invention is also applicable to infectious diseases where Rab7 is inactivated or its protein-protein interactions are modulated to facilitate intracellular survival of pathogens. The compound described acts as a competitive inhibitor of nucleotide binding and as such also has utility as a scaffold for targeting other small GTPases. In one aspect, methods of treatment of the invention are used to treat or prevent the onset of hereditary sensory neuropathies such as Charcot-Marie-Tooth type 2B disease. Related pharmaceutical compositions, assays, and drug screens are also provided.

3 Claims, 53 Drawing Sheets

Compound Chemical Structure

Compound

Target

Compound Identifiers: ML282; MLS000673908; CID1067700
2-(benzoylcarbamothioylamino)-5,5-dimethyl-4,7-dihydrothieno
[4,5-d]pyran-3-carboxylic acid

(56) References Cited

PUBLICATIONS

Fletcher S. et al., J Med Chem 53, 6867 (2010).
McKenna C. E. et al., J Med Chem 53, 3454 (2010).
Vigil D., J. Cherfils, K. L. Rossman, C. J. Der, Nat Rev Cancer 10, 842 (2010).
Nassar N., J. Cancelas, J. Zheng, D. A. Williams, Y. Zheng, Curr Top Med Chem 6, 1109 (2006).
Pelish H. E. et al., Nat Chem Biol 2, 39 (2006).
Shutes A. et al., J Biol Chem 282, 35666 (2007).
Hartmann J. T., M. Heap, H. G. Kopp, H. P. Lipp, Curr Drug Metab 10, 470-481 (2009).
Progida C. et al., J Cell Sci 120, 3729 (2007).
Vanlandingham P. A., B. P. Ceresa, J Biol Chem 284, 12110 (2009).
BasuRay S., S. Mukherjee, E. Romero, M. C. Wilson, A. Wandinger-Ness, PLoS One 5, e15351 (2010).
de Gassart A., C. Geminard, D. Hoekstra, M. Vidal, Traffic 5, 896 (2004).
Croizet-Berger K., C. Daumerie, M. Couvreur, P. J. Courtoy, M. F. van den Hove, Proc Natl Acad Sci U S A 99, 8277 (2002).
Roepstorff K., L. Grovdal, M. Grandal, M. Lerdrup, B. van Deurs, Histochem Cell Biol 129, 563 (2008).
Bains M., V. Zaegel, J. Mize-Berge, K. A. Heidenreich, Neurosci Lett 488, 112 (2011).
Gutierrez M. G., D. B. Munafo, W. Beron, M. I. Colombo, J Cell Sci 117, 2687 (2004).
Liang C. et al., Nat Cell Biol 10, 776 (2008).
Deretic V., Curr Opin Cell Biol 22, 252 (2010).
Wong E., A. M. Cuervo, Nat Neurosci 13, 805 (2010).
Cogli L. et al., Acta Neuropathol 120, 491 (2010).
Schwartz S. L. et al., Anal Biochem 381, 258 (2008).
Tessema M. et al., Cytometry A 69, 326 (2006).
Surviladze Z. et al., J Biomol Screen 15, 10 (2010).
Ramirez S., C. T. Aiken, B. Andrzejewski, L. A. Sklar, B. S. Edwards, Cytometry A 53, 55 (2003).
Simon I., M. Zerial, R. S. Goody, J Biol Chem 271, 20470 (1996).
Giraldo J., J. Serra, D. Roche, X. Rovira, Curr Drug Targets 8, 197 (2007).
Feng Y., B. Press, A. Wandinger-Ness, J Cell Biol 131, 1435 (1995).
Manara M. C. et al., Clin Cancer Res 16, 530 (2010).
Flinn R. J., Y. Yan, S. Goswami, P. J. Parker, J. M. Backer, Mol Biol Cell 21, 833 (2010).
Zhang X. M., B. Walsh, C. A. Mitchell, T. Rowe, Biochem Biophys Res Commun 335, 154 (2005).
Seto S., S. Matsumoto, K. Tsujimura, Y. Koide, Microbiol Immunol 54, 170 (2010).
Johansson M. et al., J Cell Biol 176, 459 (2007).
Rocha N. et al., J Cell Biol 185, 1209 (2009).
Mizuno K., A. Kitamura, T. Sasaki, Mol Biol Cell 14, 3741 (2003).
Dong J., W. Chen, A. Welford, A. Wandinger-Ness, J Biol Chem 279, 21334 (2004).
Mukherjee S. et al., Methods Enzymol 403, 650 (2005).
Colicelli, J., Human RAS superfamily proteins and related GTPases. Sci STKE, 2004. 2004(250): p. RE13.
Vigil, D., et al., Ras superfamily GEFs and GAPs: validated and tractable targets for cancer therapy? Nat Rev Cancer, 2010. 10(12): p. 842-57.
DerMardirossian, C. and G.M. Bokoch, GDIs: central regulatory molecules in Rho GTPase activation. Trends Cell Biol, 2005. 15(7): p. 356-63.
Konstantinopoulos, P.A., M.V. Karamouzis, and A.G. Papavassiliou, Post-translational modifications and regulation of the RAS superfamily of GTPases as anticancer targets. Nat Rev Drug Discov, 2007. 6(7): p. 541-55.
Shaw, R.J. and L.C. Cantley, Ras, PI(3)K and mTOR signalling controls tumour cell growth. Nature, 2006. 441(7092): p. 424-30.
Etienne-Manneville, S. and A. Hall, Rho GTPases in cell biology. Nature, 2002. 420(6916): p. 629-35.
Tybulewicz, V.L. and R.B. Henderson, Rho family GTPases and their regulators in lymphocytes. Nat Rev Immunol, 2009. 9(9): p. 630-44.

Stenmark, H., Rab GTPases as coordinators of vesicle traffic. Nat Rev Mol Cell Biol, 2009. 10(8): p. 513-25.
Agola, J., et al., Rab GTPases as regulators of endocytosis, targets of disease and therapeutic opportunities. Clin Genet, 2011.
Overmeyer, J.H. and W.A. Maltese, Death pathways triggered by activated Ras in cancer cells. Front Biosci, 2011. 16: p. 1693-713.
Sahai, E. and C.J. Marshall, RHO-GTPases and cancer. Nat Rev Cancer, 2002. 2(2): p. 133-42.
Vega, F.M. and A.J. Ridley, Rho GTPases in cancer cell biology. FEBS Lett, 2008. 582(14): p. 2093-101.
Stengel, K. and Y. Zheng, Cdc42 in oncogenic transformation, invasion, and tumorigenesis. Cell Signal, 2011. 23(9): p. 1415-23.
Hooff, G.P., et al., Isoprenoids, small GTPases and Alzheimer's disease. Biochim Biophys Acta, 2010. 1801(8): p. 896-905.
McCray, B.A., E. Skordalakes, and J.P. Taylor, Disease mutations in Rab7 result in unregulated nucleotide exchange and inappropriate activation. Hum Mol Genet, 2010. 19(6): p. 1033-47.
Cogli, L., F. Piro, and C. Bucci, Rab7 and the CMT2B disease. Biochem Soc Trans, 2009. 37(Pt 5): p. 1027-31.
BasuRay, S., et al., Rab7 mutants associated with Charcot-Marie-Tooth disease exhibit enhanced NGF-stimulated signaling. PLoS One, 2010. 5(12): p. e15351.
Schafer, W.R., et al., Genetic and pharmacological suppression of oncogenic mutations in ras genes of yeast and humans. Science, 1989. 245(4916): p. 379-85.
Sebti, S.M. and A.D. Hamilton, Farnesyltransferase and geranylgeranyltransferase I inhibitors and cancer therapy: lessons from mechanism and bench-to-bedside translational studies. Oncogene, 2000. 19(56): p. 6584-93.
Cherfils, J. and P. Melancon, On the action of Brefeldin A on Sec7-stimulated membrane-recruitment and GDP/GTP exchange of Arf proteins. Biochem Soc Trans, 2005. 33(Pt 4): p. 635-8.
Sata, M., et al., Brefeldin A-inhibited guanine nucleotide-exchange activity of Sec7 domain from yeast Sec7 with yeast and mammalian ADP ribosylation factors. Proc Natl Acad Sci U S A, 1998. 95(8): p. 4204-8.
Peyroche, A., et al., Brefeldin a acts to stabilize an abortive ARF-GDP-Sec7 domain protein complex: involvement of specific residues of the Sec7 domain. Mol Cell, 1999. 3(3): p. 275-85.
Sata, M. J. Moss, and M. Vaughan, Structural basis for the inhibitory effect of brefeldin A on guanine nucleotide-exchange proteins for ADP-ribosylation factors. Proc Natl Acad Sci U S A, 1999. 96(6): p. 2752-7.
Renault, L., B. Guibert, and J. Cherfils, Structural snapshots of the mechanism and inhibition of a guanine nucleotide exchange factor. Nature, 2003. 426(6966): p. 525-30.
Viaud, J., et al., Structure-based discovery of an inhibitor of Arf activation by Sec7 domains through targeting of protein-protein complexes. Proc Natl Acad Sci U S A, 2007. 104(25): p. 10370-5.
Nassar, N., et al., Structure-function based design of small molecule inhibitors targeting Rho family GTPases. Curr Top Med Chem, 2006. 6(11): p. 1109-16.
Pelish, H.E., et al., Secramine inhibits Cdc42-dependent functions in cells and Cdc42 activation in vitro. Nat Chem Biol, 2006. 2(1): p. 39-46.
Shutes, A., et al., Specificity and mechanism of action of EHT 1864, a novel small molecule inhibitor of Rac family small GTPases. J Biol Chem, 2007. 282(49): p. 35666-78.
Surviladze, Z., et al., A Potent and Selective Inhibitor of Cdc42 GTPase. 2010 e-pub.
Surviladze, Z., et al., Identification of a small GTPase inhibitor using a high-throughput flow cytometry bead-based multiplex assay. J Biomol Screen, 2010. 15(1): p. 10-20.
Nakano, H. and S. Omura, Chemical biology of natural indolocarbazole products: 30 years since the discovery of staurosporine. J Antibiot (Tokyo), 2009. 62(1): p. 17-26.
Gescher, A., Analogs of staurosporine: potential anticancer drugs? Gen Pharmacol, 1998. 31(5): p. 721-8.
Lapenna, S. and A. Giordano, Cell cycle kinases as therapeutic targets for cancer. Nat Rev Drug Discov, 2009. 8(7): p. 547-66.
Hill, M.M. and B.A. Hemmings, Inhibition of protein kinase B/Akt. implications for cancer therapy. Pharmacol Ther, 2002. 93(2-3): p. 243-51.

(56) References Cited

OTHER PUBLICATIONS

Ustun, C., D.L. DeRemer, and C. Akin, Tyrosine kinase inhibitors in the treatment of systemic mastocytosis. Leuk Res, 2011. 35(9): p. 1143-52.
Chigaev, A., et al., Real time analysis of the affinity regulation of alpha 4-integrin. The physiologically activated receptor is intermediate in affinity between resting and Mn(2+) or antibody activation. J Biol Chem, 2001. 276(52): p. 48670-8.
Chigaev, A. and L.A. Sklar, Overview: assays for studying integrin-dependent cell adhesion. Methods Mol Biol, 2012. 757: p. 3-14.
Chigaev, A., Y. Smagley, and L.A. Sklar, Nitric oxide/cGMP pathway signaling actively down-regulates alpha4beta1-integrin affinity: an unexpected mechanism for inducing cell de-adhesion. BMC Immunol, 2011. 12: p. 28.
Gopinathan, S., Nouraldeen, A., Wilson, A.G.E. Development and application of a highthroughput formulation screening strategy for oral administration in drug discovery. Future Med. Chem. (2010) 2(9), 1391-1398.
Ibrahim F, Ei-Din Mk, Eid Mi, Wahba ME. 2011. Validated stability-indicating spectrofluorimetric methods for the determination of ebastine in pharmaceutical preparations. Chem Cent J. 5(1):11.
Andersen, H. S., Olsen, O. H., Iversen, L. F., Sorensen, A. L. P., Mortensen, S. B., Christensen, M.S., Branner, S., Hansen, T. K., Lau, J. F., Jeppesen, L., Moran, E. J., Su, J., Bakir, F., Judge, L., Shahbaz, M., Collins, T., Vo, T., Newman, M. J., Ripka, W. C., Moller, N. P. H. (2002) Discovery and SAR of a Novel Selective and Orally Bioavailable Nonpeptide Classical Competitive Inhibitor Class of Protein-Tyrosine Phosphatase 1B, J. Med. Chem. 45, 4443-4459.
Copeland, R.A., Evaluation of enzyme inhibitors in drug discovery : a guide for medicinal chemists and pharmacologists. 2005, Hoboken,N.J.: Wiley-Interscience. xvii, 271 p. (title page and final page only).
Zella, D., et al., Interferon-gamma increases expression of chemokine receptors CCR1, CCR3, and CCR5, but not CXCR4 in monocytoid U937 cells. Blood, 1998. 91(12): p. 4444-50.
Hogg, N., I. Patzak, and F. Willenbrock, The insider's guide to leukocyte integrin signalling and function. Nat Rev Immunol, 2011. 11(6): p. 416-26.
Abram, C.L. and C.A. Lowell, The ins and outs of leukocyte integrin signaling. Annu Rev Immunol, 2009. 27: p. 339-62.
Hyun, Y.M., C.T. Lefort, and M. Kim, Leukocyte integrins and their ligand interactions. Immunol Res, 2009.
Yusuf-Makagiansar, H., et al., Inhibition of LFA-1/ICAM-1 and VLA-4/VCAM-1 as a therapeutic approach to inflammation and autoimmune diseases. Med Res Rev, 2002. 22(2): p. 146-67.
Rice, G.P., H.P. Hartung, and P.A. Calabresi, Anti-alpha4 integrin therapy for multiple sclerosis: mechanisms and rationale. Neurology, 2005. 64(8): p. 1336-42.
Chatterjee, M., et al., Individual rac GTPases mediate aspects of prostate cancer cell and bone marrow endothelial cell interactions. J Signal Transduct, 2011.2011: p. 541851.
Laudanna, C., J.J. Campbell, and E.C. Butcher, Role of Rho in chemoattractant-activated leukocyte adhesion through integrins. Science, 1996. 271(5251): p. 981-3.

Arpaia, E., et al., The interaction between caveolin-1 and Rho-GTPases promotes metastasis by controlling the expression of alpha5-integrin and the activation of Src, Ras and Erk. Oncogene, 2011.
Rathinam, R., A. Berrier, and S.K. Alahari, Role of Rho GTPases and their regulators in cancer progression. Front Biosci, 2011. 17: p. 2561-71.
Szczur, K., Y. Zheng, and M.D. Filippi, The small Rho GTPase Cdc42 regulates neutrophil polarity via CD11b integrin signaling. Blood, 2009. 114(20): p. 4527-37.
Langereis, J.D., et al., A 2D-DIGE approach to identify proteins involved in inside-out control of integrins. J Proteome Res, 2009. 8(8): p. 3824-33.
Fernandez-Sauze, S., et al., Regulation of fibronectin matrix assembly and capillary morphogenesis in endothelial cells by Rho family GTPases. Exp Cell Res, 2009. 315(12): p. 2092-104.
Bolomini-Vittori, M., et al., Regulation of conformer-specific activation of the integrin LFA-1 by a chemokine-triggered Rho signaling module. Nat Immunol, 2009. 10(2): p. 185-94.
Ceresa, B.P., Regulation of EGFR endocytic trafficking by rab proteins. Histol Histopathol, 2006. 21(9): p. 987-93.
Barbieri, M.A., et al., Role of rab5 in EGF receptor-mediated signal transduction. Eur J Cell Biol, 2004. 83(6): p. 305-14.
Li, G., Rab GTPases, membrane trafficking and diseases. Curr Drug Targets, 2011. 12(8): p. 1188-93.
Reck, M., et al., Erlotinib in advanced non-small cell lung cancer: efficacy and safety findings of the global phase IV Tarceva Lung Cancer Survival Treatment study. J Thorac Oncol, 2010. 5(10): p. 1616-22.
Gridelli, C., et al., Erlotinib in the treatment of non-small cell lung cancer: current status and future developments. Anticancer Res, 2010. 30(4): p. 1301-10.
Bayraktar, S. and C.M. Rocha-Lima, Advanced or metastatic pancreatic cancer: molecular targeted therapies. Mt Sinai J Med, 2010. 77(6): p. 606-19.
Mountzios, G. and K.N. Syrigos, A benefit-risk assessment of erlotinib in non-small-cell lung cancer and pancreatic cancer. Drug Saf, 2011. 34(3): p. 175-86.
Catellani, S., et al., Imatinib treatment induces CD5+ B lymphocytes and IgM natural antibodies with anti-leukemic reactivity in patients with chronic myelogenous leukemia. PLoS One, 2011. 6(4): p. e18925.
Mazzeo, F., et al., Nonadherence to imatinib treatment in patients with gastrointestinal stromal tumors: the ADAGIO study. Anticancer Res, 2011. 31(4): p. 1407-9.
Jaffe, A.B. and A. Hall, Rho GTPases: biochemistry and biology. Annu Rev Cell Dev Biol, 2005. 21: p. 247-69.
Korlach, J., et al., Spontaneous nucleotide exchange in low molecular weight GTPases by fluorescently labeled gamma-phosphate-linked GTP analogs. Proc Natl Acad Sci U S A, 2004. 101(9): p. 2800-5.
Schwartz, S.L., et al., Flow cytometry for real-time measurement of guanine nucleotide binding and exchange by Ras-like GTPases. Anal Biochem, 2008. 381(2): p. 258-66.
Segel, I.H., Enzyme kinetics : behavior and analysis of rapid equilibrium and steady state enzyme systems. 1975, New York: Wiley. xxii, 957 p. (title page and final page only).

* cited by examiner

Compound Identifiers: ML282; MLS000673908; CID10067700
2-(benzoylcarbamothioylamino)-5,5-dimethyl-4,7-dihydrothieno[4,5-d]pyran-3-carboxylic acid Figure 5
Rab7 GTPase Involvement in Human Disease
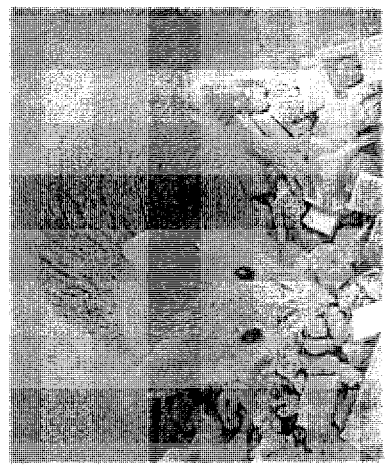
Normal mouse
Mouse with Charcot-Marie-Tooth (CMT) disease mutation
❖ Clinical characteristics of CMT2B:
  ➢ Distal muscle weakness and wasting
  ➢ Foot ulcers and infections
  ➢ Amputations of the toes
www.nigms.nih.gov/biobeat/07-07-18/

Figure 9
Rab7 On rate kinetics
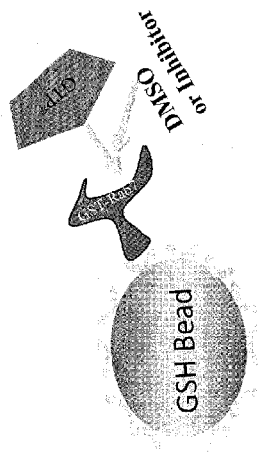
(A) Control (0.1 % DMSO for 2 min)
(B) MLS000673908 (10 µM for 2 min)
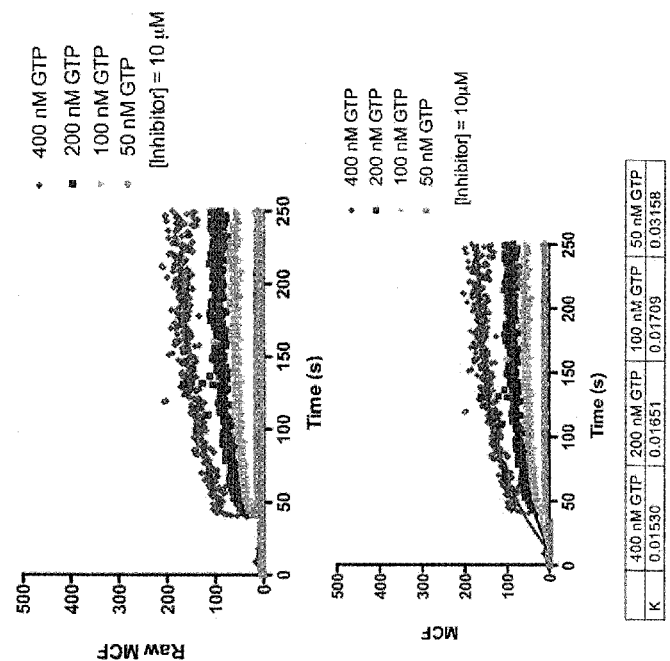
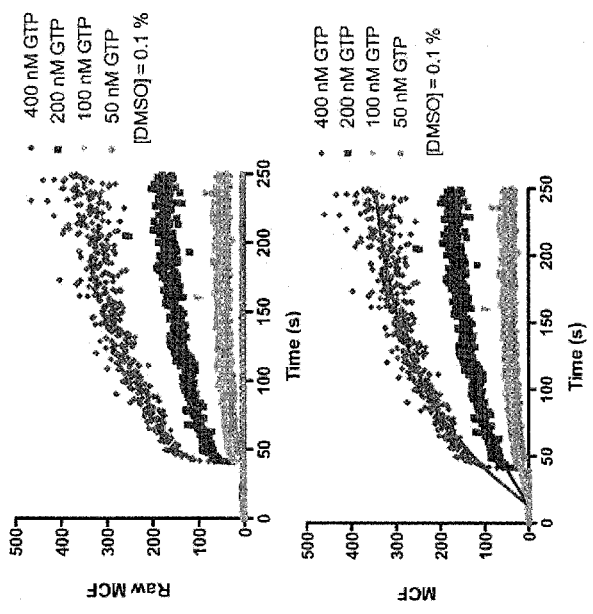

Offrate kinetics of Rab7WT

Effect of inhibitor on onrate and off rate kinetics: Rab7 bound GTP* displaced by 200 μM unlabelled GTP Figure 12
Off rate kinetics of Rab7WT
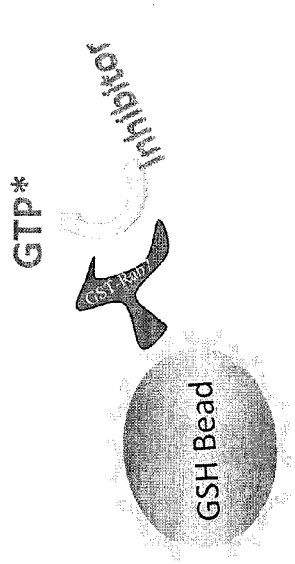
(A) 0.1 % DMSO used to displace bound GTP
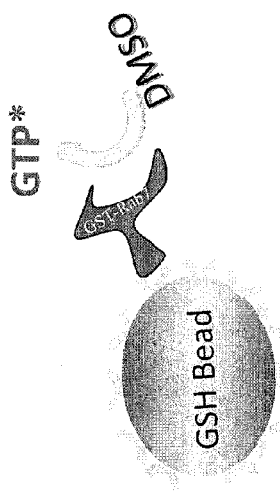
(B) MLS000673908 (10 µM) used to displace bound GTP
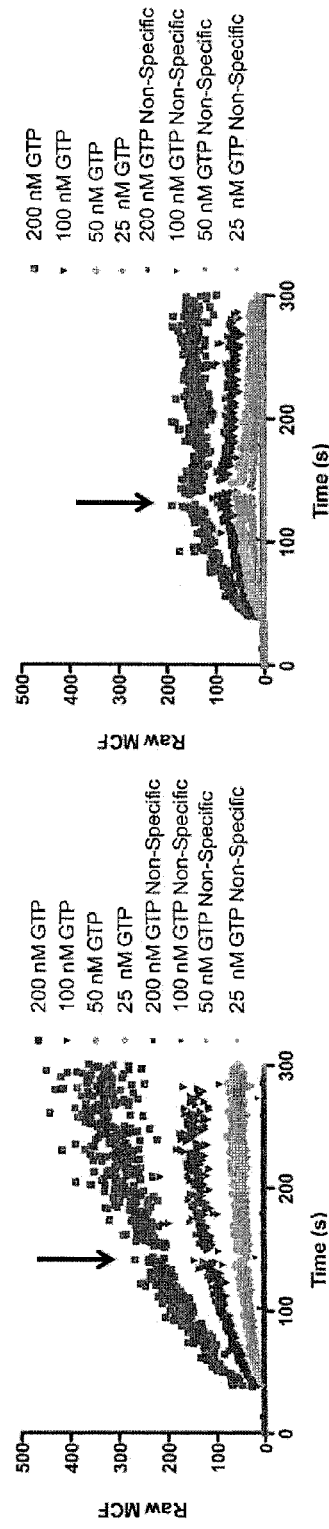

Figure 13
MLS000673908 is a competitive inhibitor of the nucleotide binding site
(A) 200 μM unlabelled GTP used to displace bound GTP*
(B) MLS000673908 used to displace bound GTP*
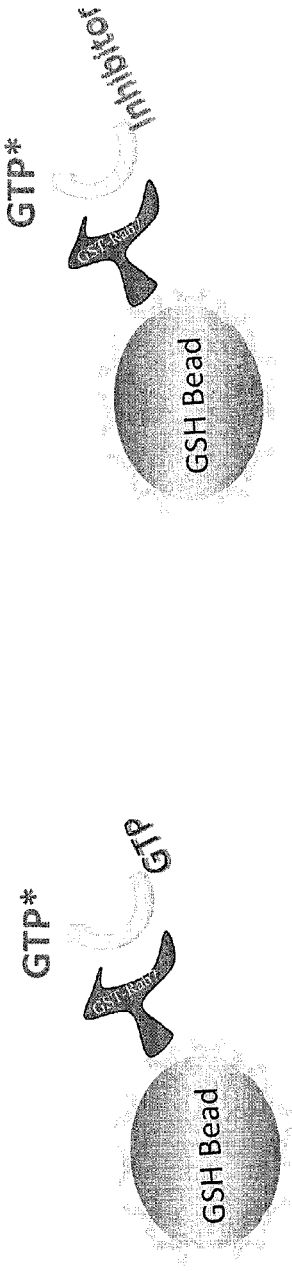
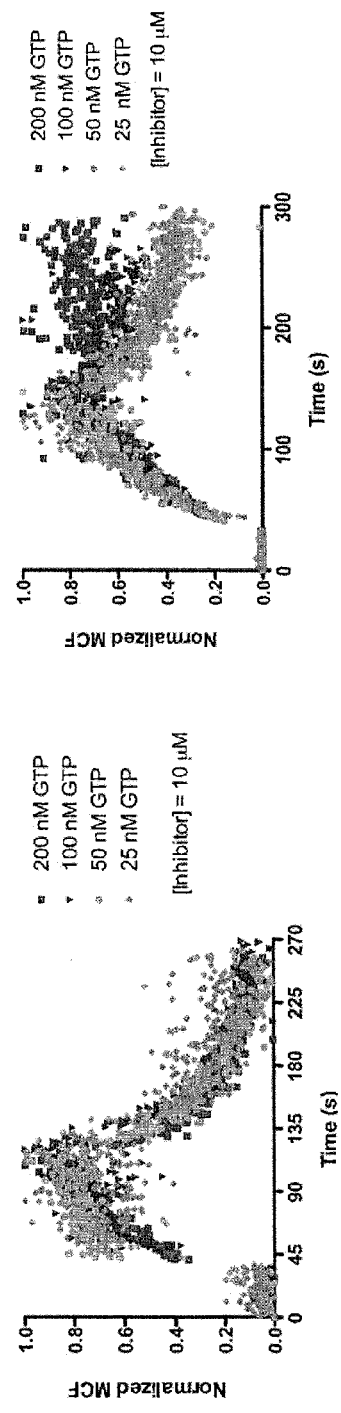

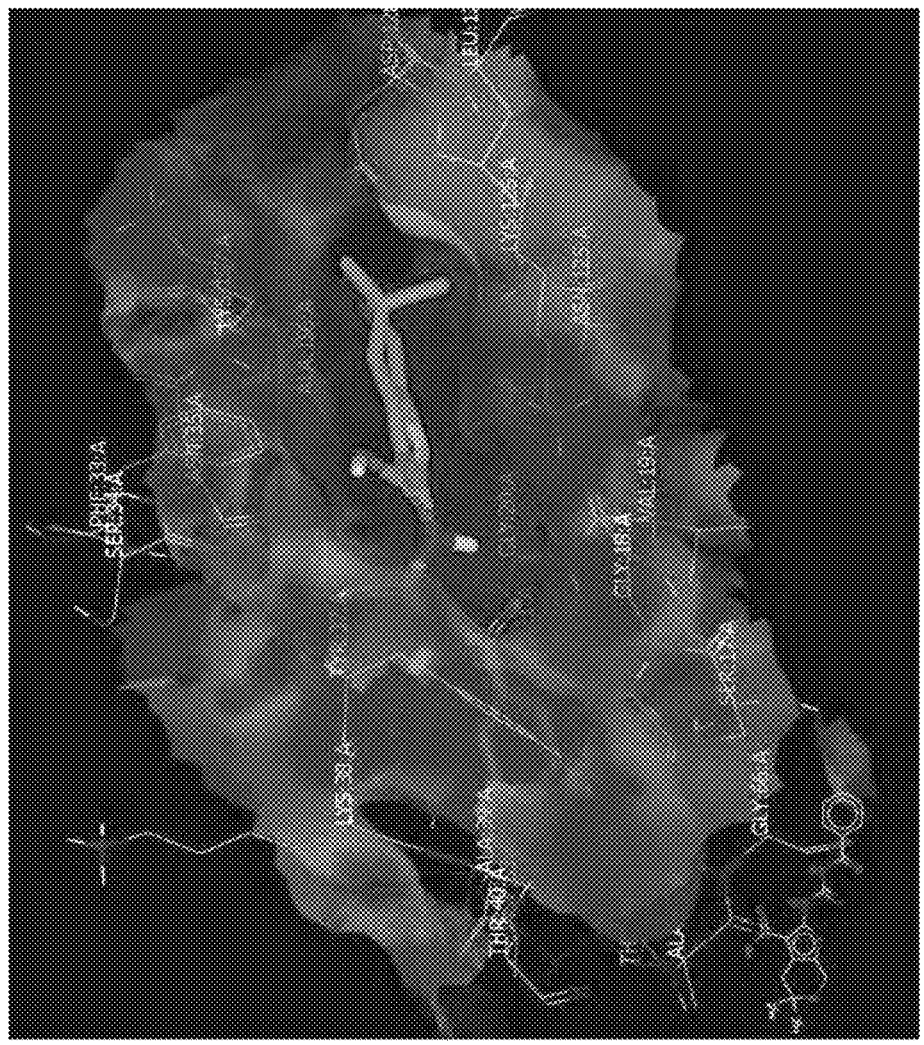
FIGURE 14A MLS000673908 docked on Rab7

FIGURE 14B
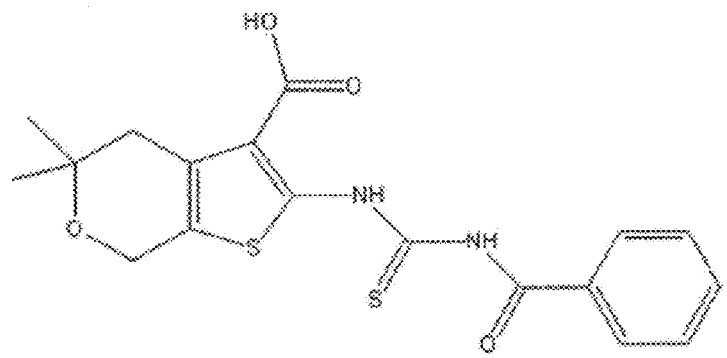
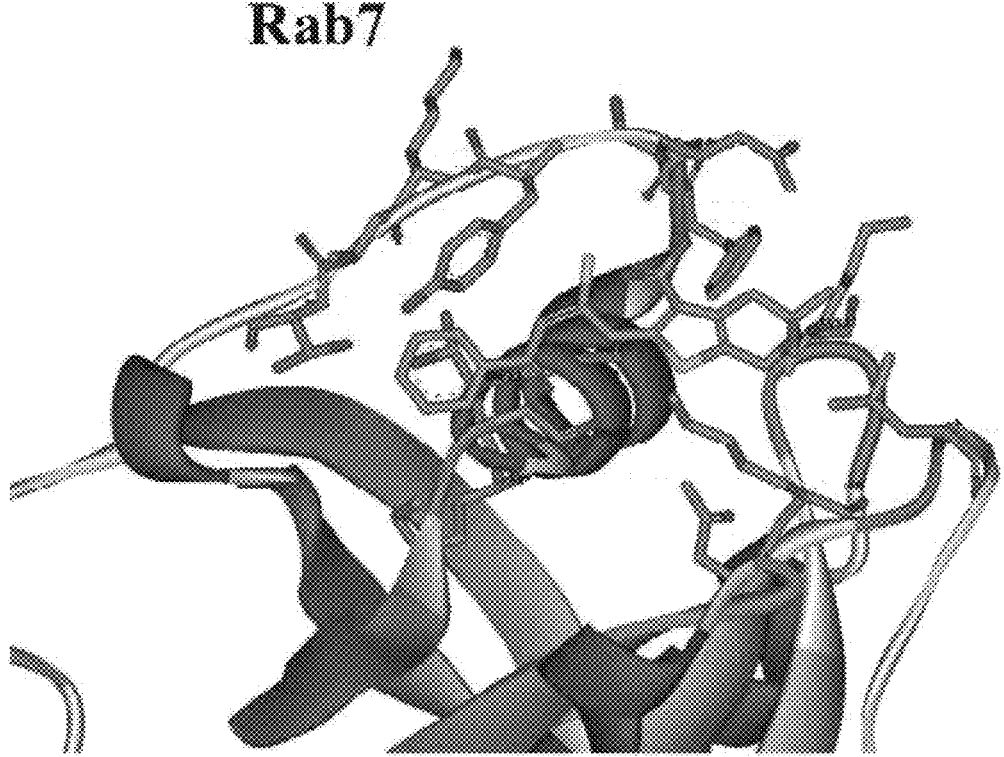

Rab7 Function in Endocytosis Depends on Protein-Protein Interactions

2. To test if the molecule, MLS000673908 modulates Rab7WT protein-protein in vitro

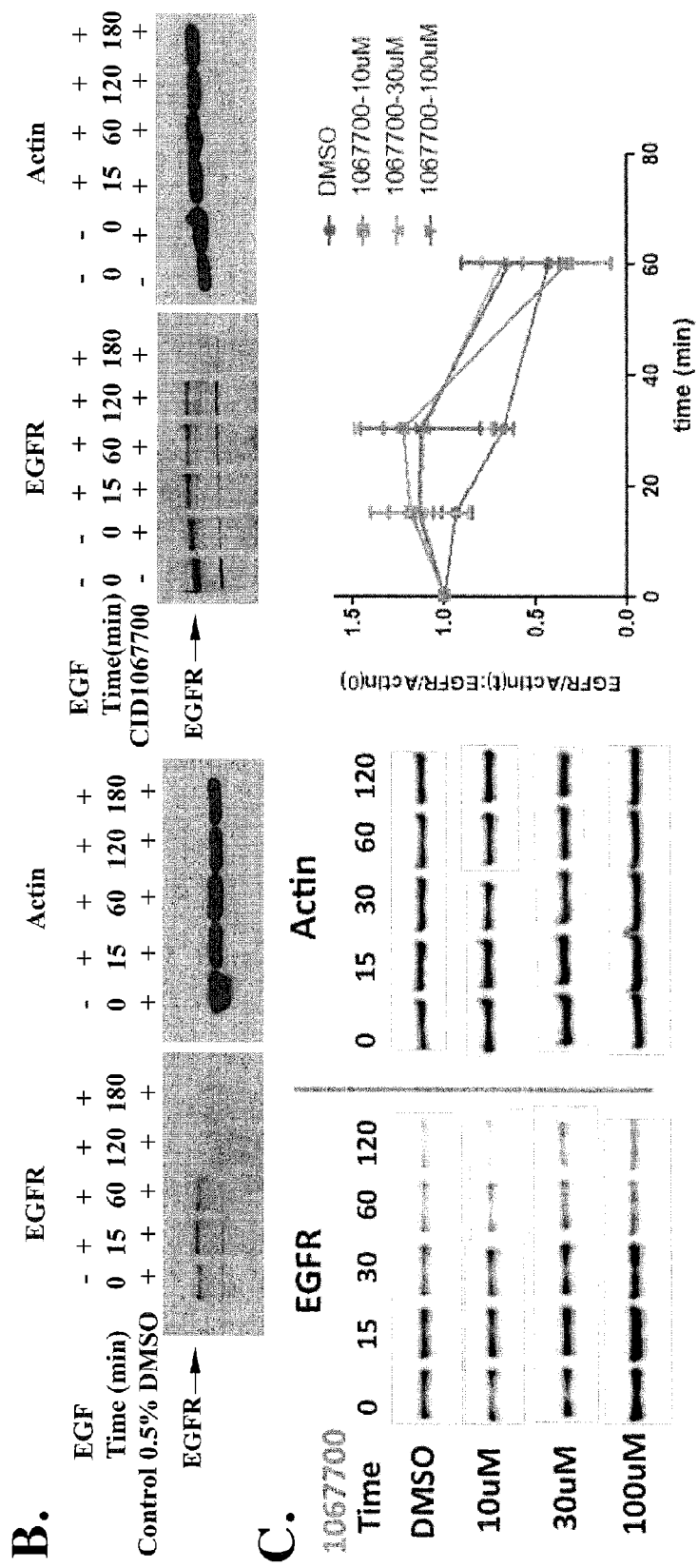
Figure 18 B-C

Rab7 CMT disease associated mutants

❖ Rab7 CMT mutants:
  ➢ L129F and K157N closer to the nucleotide binding pocket
  ➢ N161T and V162M occur on regulatory regions of the protein

GTP binding affinity of Rab7WT and its mutants associated with CMT2B disease compared

GDP binding affinity of Rab7WT and its mutants associated with CMT2B disease compared

Figure 24 ML282 (CID1067700), and shaded regions of SAR optimization

Effect of modifying the thiourea-carbonyl linker (shaded) on potency

Figure 26   ML282 (CID1067700) inhibits VLA4 binding to LDV peptide.

Binding affinity between FITC-LDV and the VLA4 receptor estimated by FITC-LDV dissociation rate constant Dissociation rates and percentage of active integrins in the presence of small molecule inhibitor

Figure 29 A-B
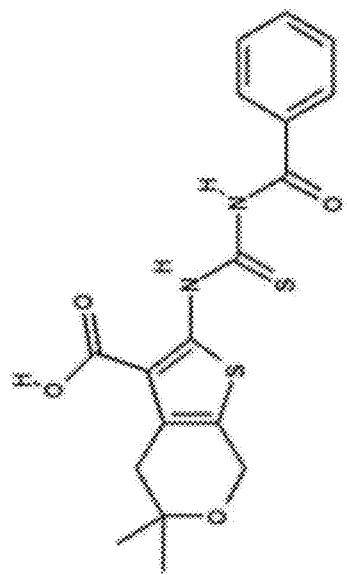
MLS0006739908; CID1067700
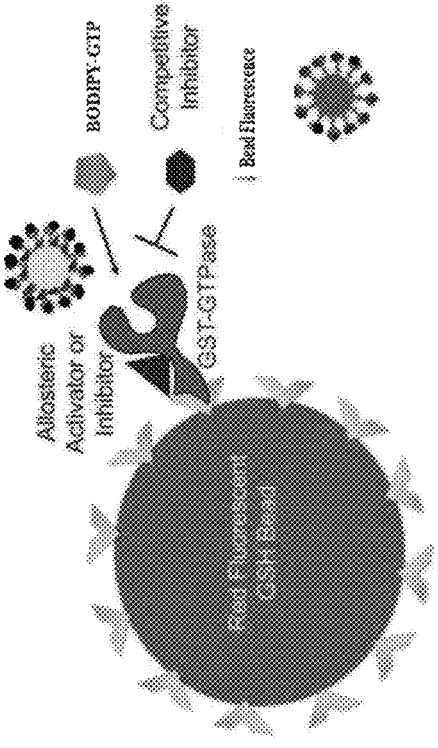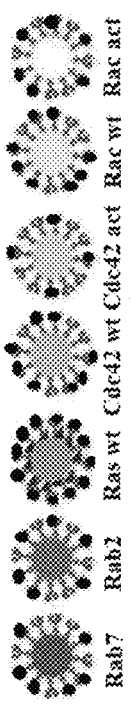
A. HTS Assay for Small Molecule Activators or Inhibitors of GTP-binding
B. Multiplex HTS using Graded Intensity Red Fluorescent Beads bearing Individual GTPases (Rab, Ras and Rho-family) and BODIPY-GTP
Rab7    Rab2    Ras wt    Cdc42 wt    Cdc42 act    Rac wt    Rac act

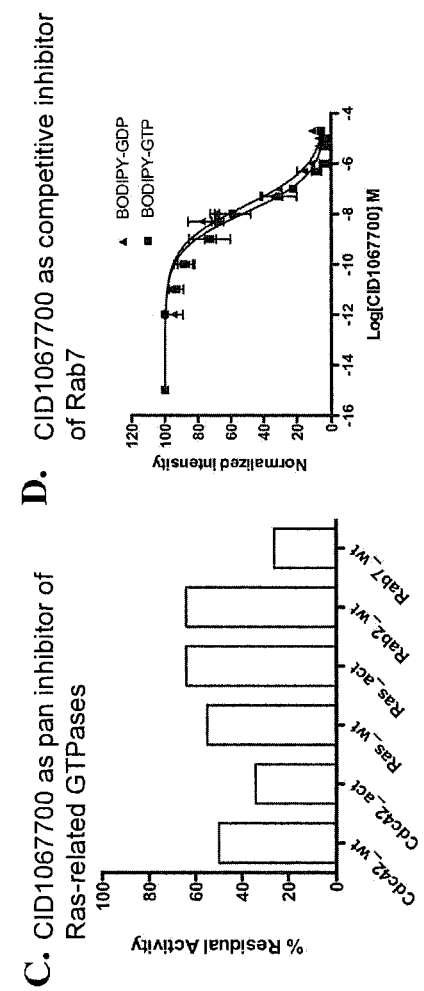
Figure 29C-D

E. Unlabeled nucleotides compete for BODIPY-nucleotide binding to Rab7

Figure 30 a-b
100 nM CID1067700 competitively inhibits BODIPY-linked nucleotide binding by wild-type Rab7
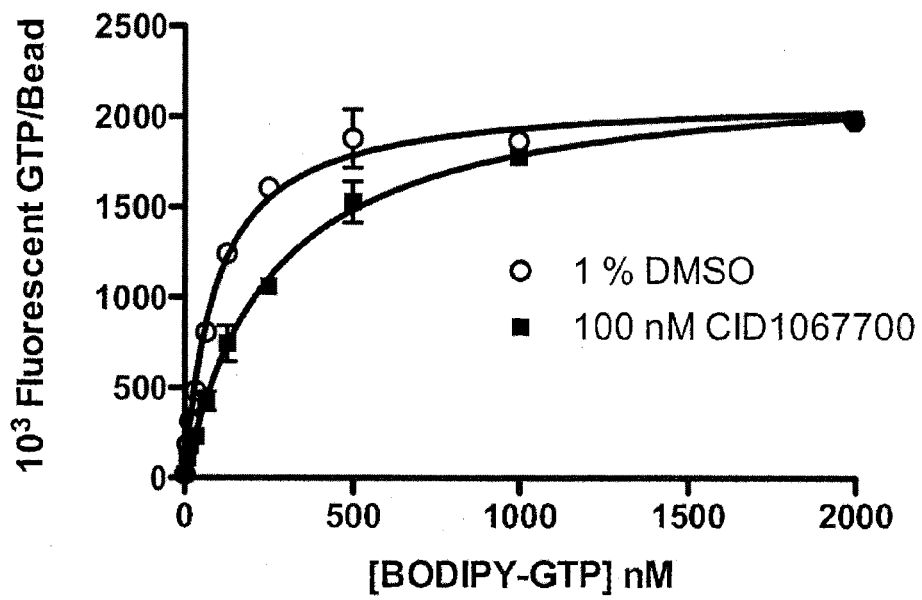
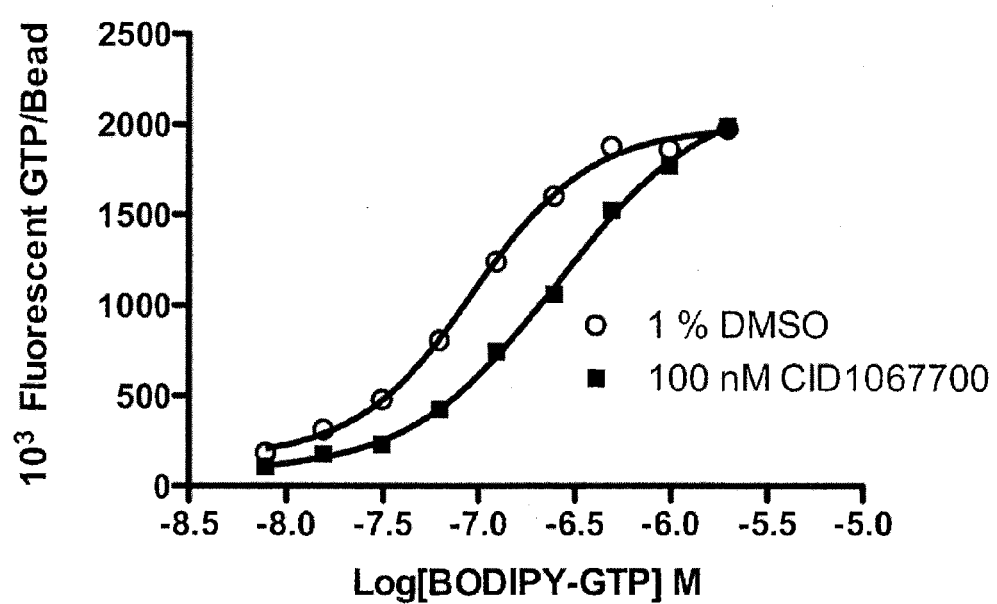

Figure 30 c-d
200 nM CID1067700 competitively inhibits BODIPY-linked nucleotide binding by wild-type Rab7
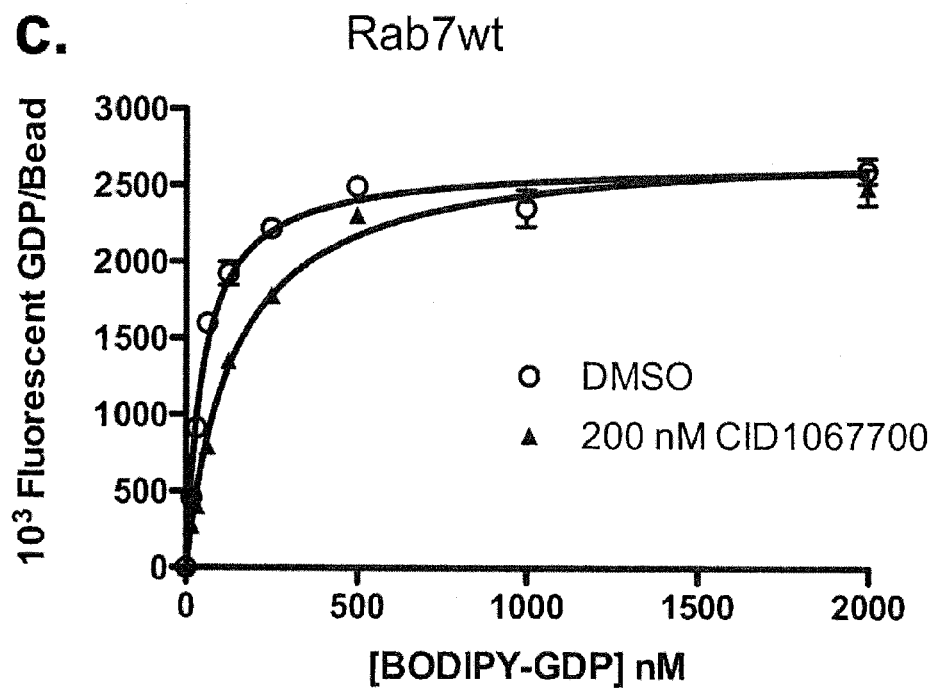
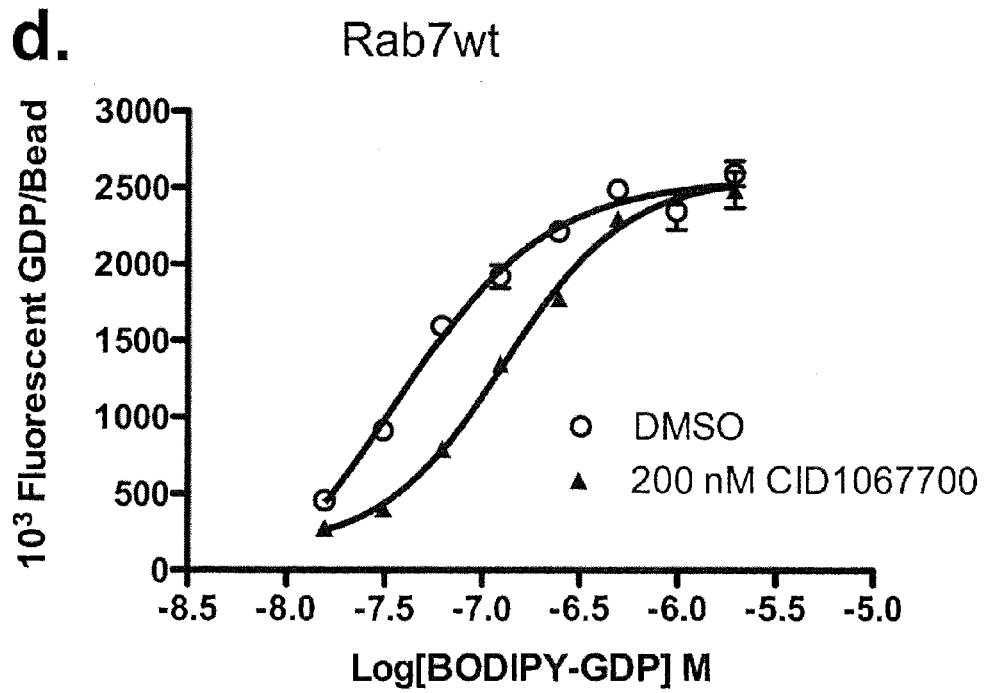

Figure 30 e-f
100 nM CID1067700 competitively inhibits BODIPY-linked nucleotide binding by activated Rab7
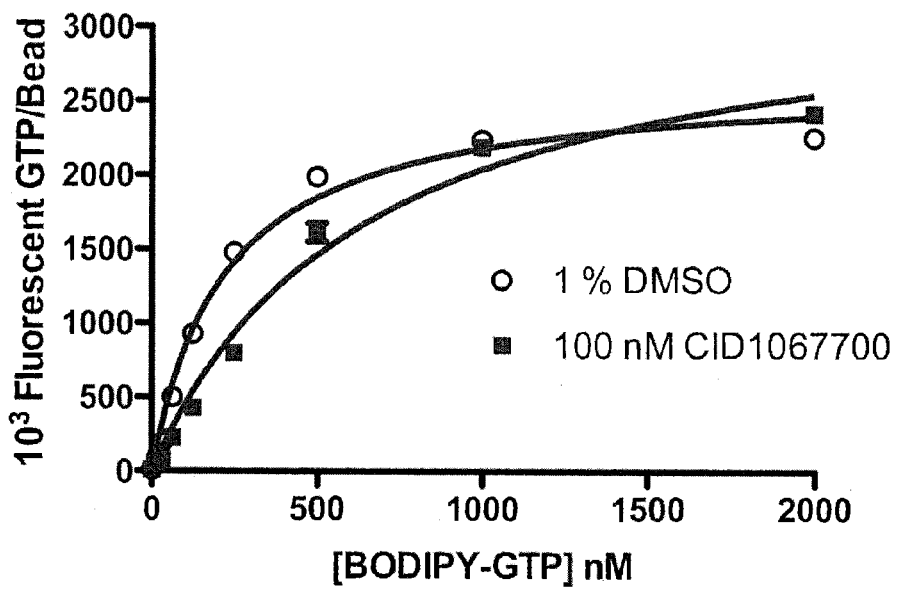
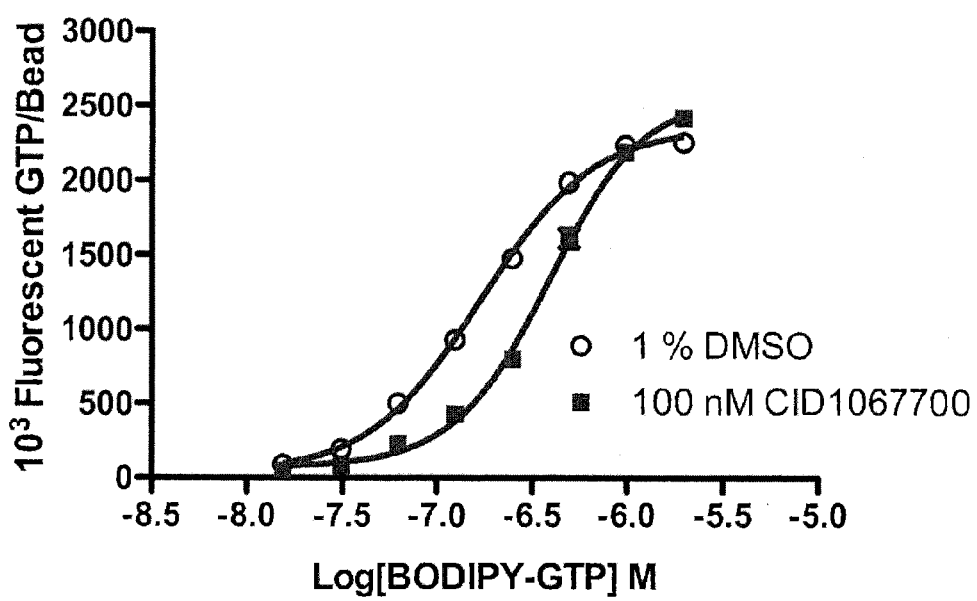

Figure 30 g-h
100 nM CID1067700 competitively inhibits BODIPY-linked nucleotide binding by inactive Rab7
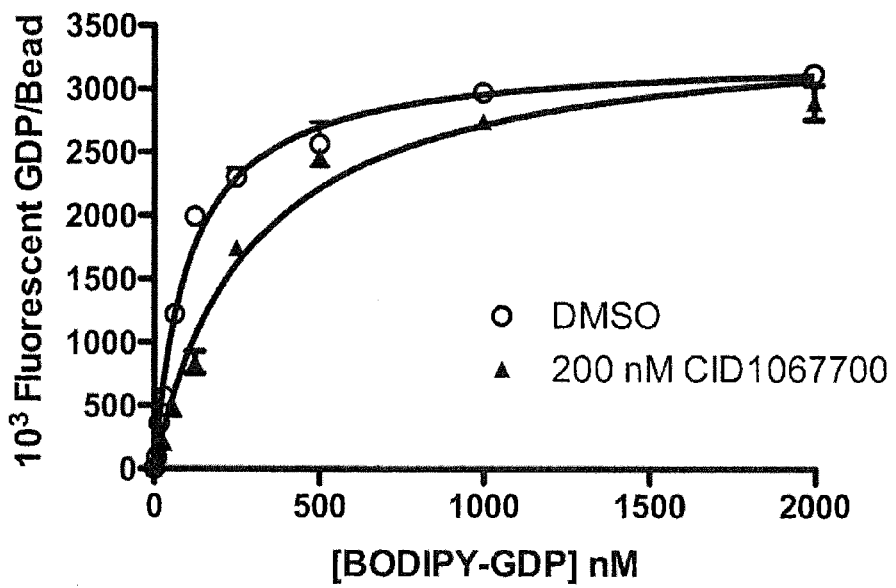
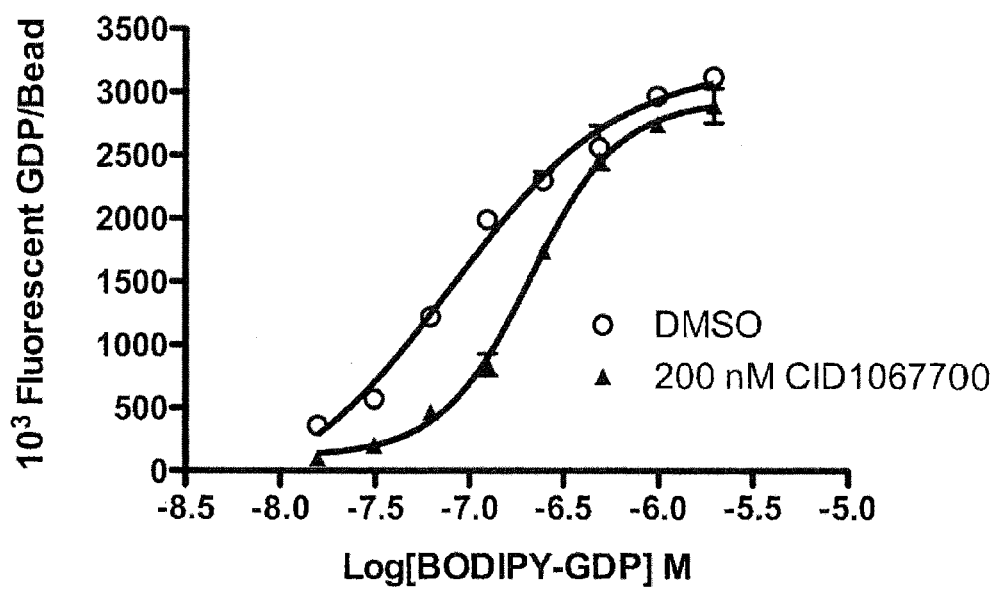

Figure 31 A-B
CID1067700 has no effect on the rate of release of bound BODIPY-GTP by wild type Rab7 under equilibrium binding conditions.
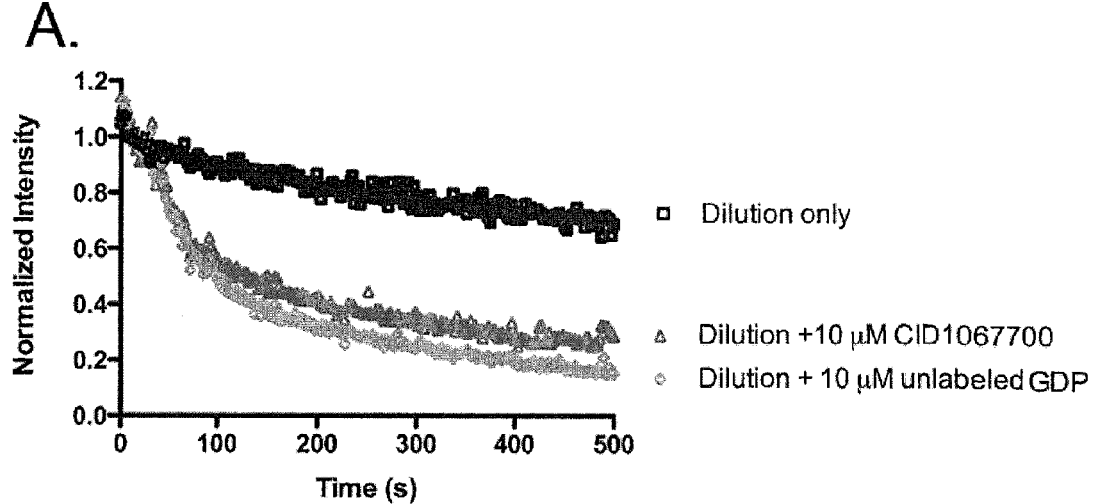
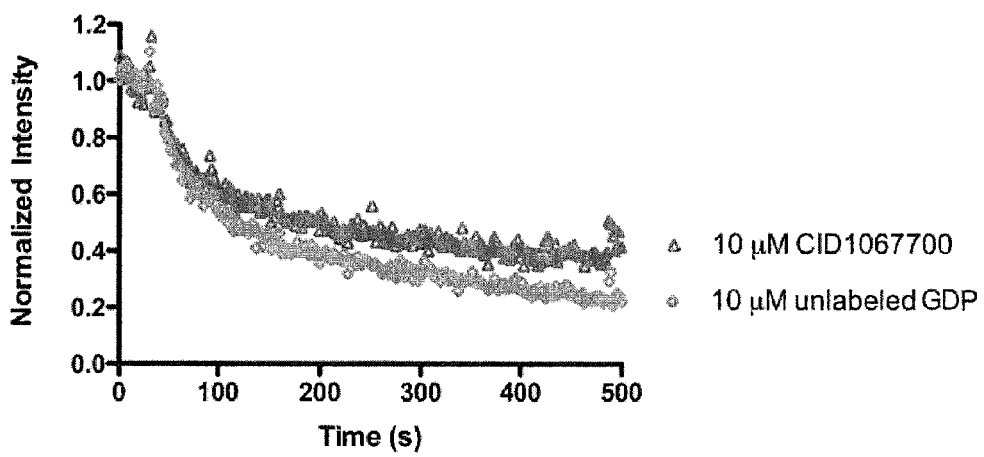

Figure 31 C-D
CID1067700 has no effect on the rate of release of bound BODIPY-GDP by wild type Rab7 under equilibrium binding conditions
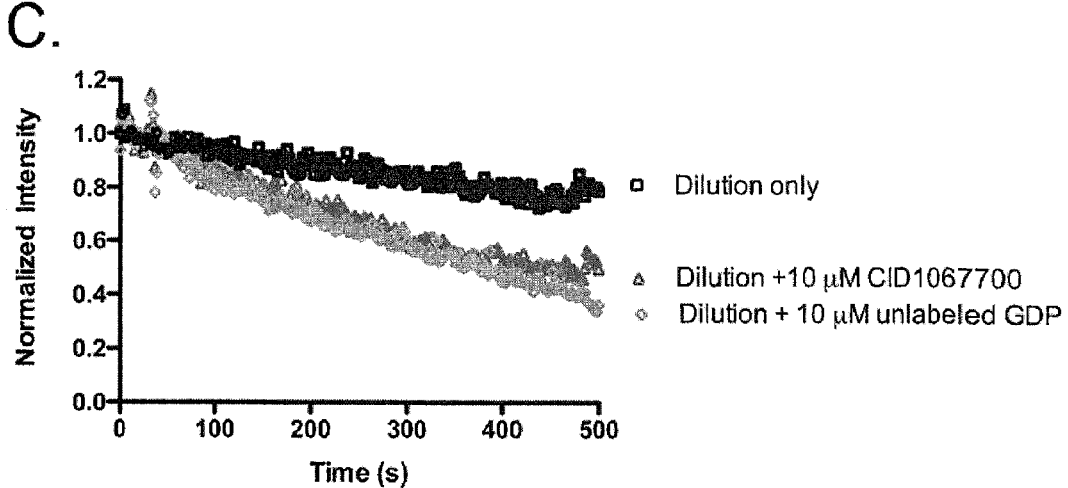
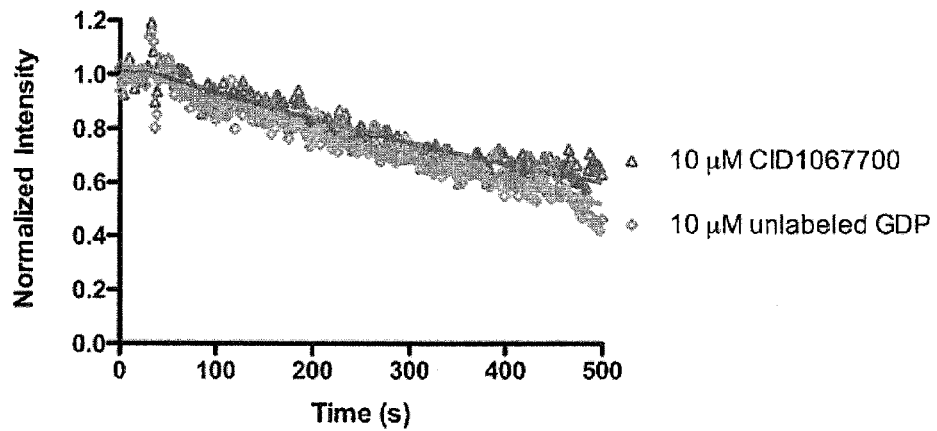

Figure 33 A-C
Structure activity relationships identify importance of linker and R-groups in inhibitory activity of CID1067700.
A.
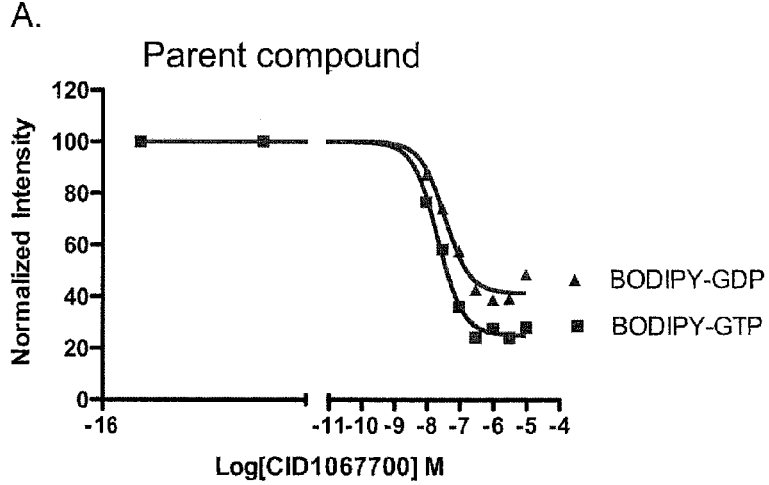
B.
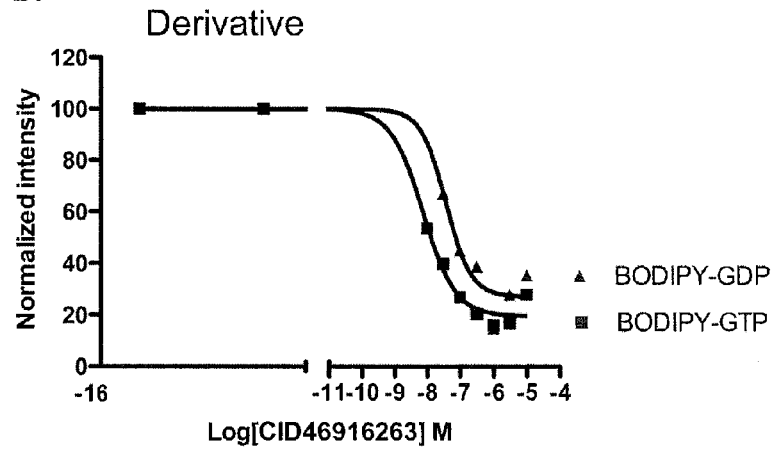
C.
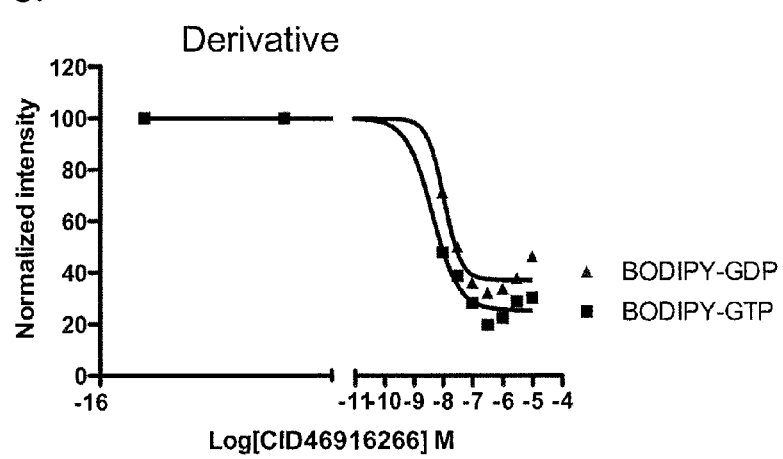

Figure 33 D-E
D.
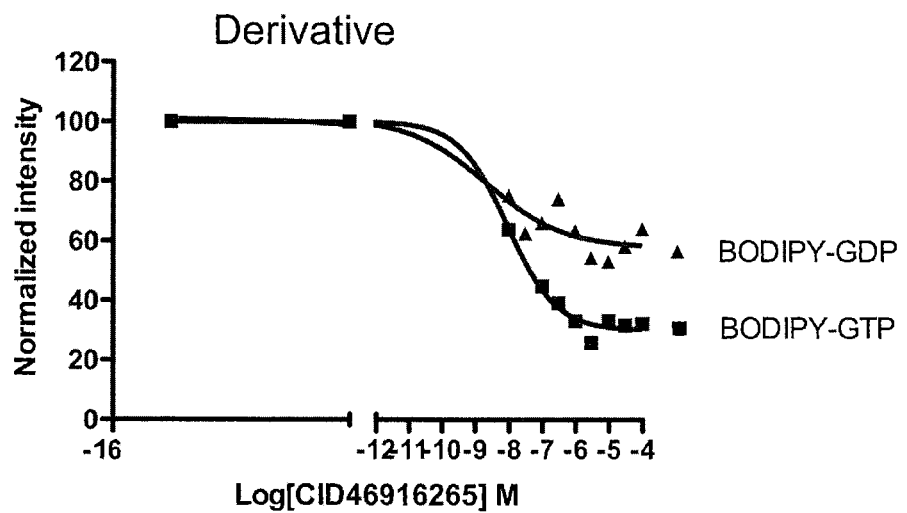
E.
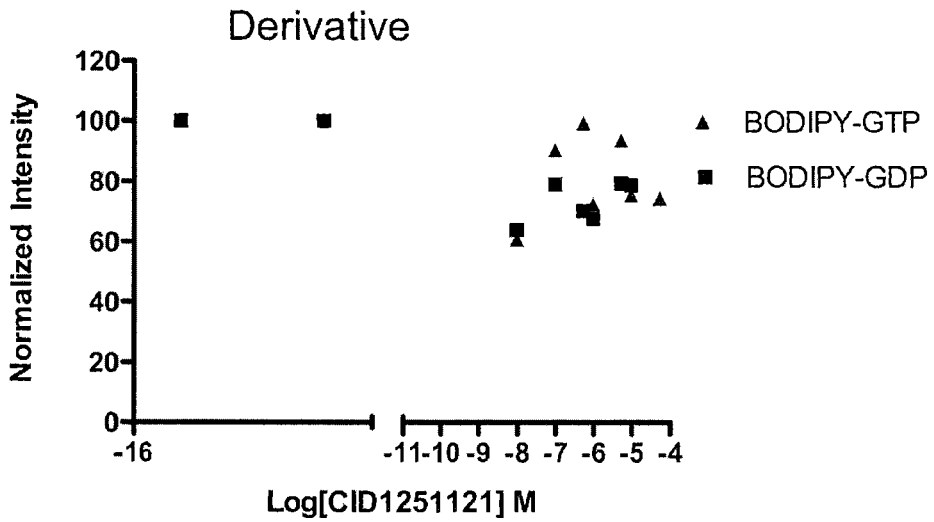

EC$_{50}$ values of CID1067700 and analogs on Rab7 nucleotide binding

| Entry | Pubchem SID | Pubchem CID | R$_1$ | R$_2$ | R$_3$ | L | EC$_{50}$ (μM) |
|---|---|---|---|---|---|---|---|
| 1 | 57578339 | 1067700 | H | Me | Me | C$_2$-NH-C(=S)-NH-C(=O)-* | 0.024 |
| 2 | 99381128 | 46916263 | H | Me | H | C$_2$-NH-C(=S)-NH-C(=O)-* | 0.27 |
| 3 | 99381129 | 46916266 | H | H | H | C$_2$-NH-C(=S)-NH-C(=O)-* | 0.50 |
| 4 | 99361118 | 1251121 | Me | Me | Me | C$_2$-NH-C(=S)-NH-C(=O)-* | > X (limits of assay) |
| 5 | 99381130 | 46916265 | H | Me | Me | C$_2$-NH-C(=O)-NH-C(=O)-* | 0.83 |
| 6 | 99381127 | 1280844 | H | Me | Me | C$_2$-NH-C(=S)-NH-* | > X (limits of assay) |
| 7 | 99381117 | 740871 | H | Me | Me | C$_2$-NH-C(=O)-* | > X (limits of assay) |

RAB7 GTPASE INHIBITORS AND RELATED METHODS OF TREATMENT

RELATED APPLICATIONS

This application claims the benefit of priority of U.S. provisional application No. US61/464,271, entitled "Rab7 GTPase Inhibitors and Related Methods of Treatment", filed Mar. 2, 2011, the entire contents of which application are incorporated by reference herein.

GOVERNMENT INTEREST

This patent application was supported by NIMH Grant No. 1R03MH081231, National Science Foundation Grant Nos. MCB0446179 and MCB0956027, National Institutes of Health Grant Nos. R03MH081231, R21NS7740241, P30CA1181000, U54 MH074425 and U54 MH084690 as well as National Institutes of Health, MLPCN, Grant No. (U54 HG005031). The Government has certain rights in the invention.

FIELD OF THE INVENTION

This invention relates to the use of small molecule inhibitors of Rab7 GTPase to treat or prevent the onset of Rab7 GTPase-associated disorders such as infectious diseases, neuropathies, immune dysfunction, neurodegenerative diseases, cancer and lipid storage diseases. This is due to the critical role Rab7 plays in a host of cellular processes including antigen presentation, autophagy, pathogen degradation and growth factor downregulation that impact intracellular survival of pathogens, immune and neuronal cell function among others. In one aspect, methods of treatment of the invention are used to treat or prevent the onset of hereditary sensory neuropathies such as Charcot-Marie-Tooth type 2B disease. In another aspect, the inhibitor can be used as a scaffold or as a reference for the development of selective inhibitors of related GTPases. Related pharmaceutical compositions, assays, and drug screens are also provided.

BACKGROUND OF THE INVENTION

Ras and related small molecular weight GTPases function in the regulation of signaling and cell growth, and collectively serve to control cell proliferation, differentiation and apoptosis (FIG. 1) [Takai et al. 2001; Wennerberg et al. 2005]. The Ras-related GTPases are divided into four subfamilies with the Rab proteins regulating membrane transport, Rho proteins (including Rac and Cdc 42) regulating cytoskeletal rearrangements and responses to signaling, Arf/Sar proteins regulating membrane and microtubule dynamics as well as protein transport, and Ran proteins controlling nucleocytoplasmic transport.

Ras and Ras-related GTPase functions are tightly regulated (FIG. 2), and dysregulation is causal in a wide variety of human diseases. Ras mutations resulting in impaired GTP hydrolysis and plasma membrane hyperactivation are linked to many human cancers [Farnsworth et al. 1991; Sukumar et al. 1983; Taparowsky et al. 1982; Boylan et al. 1990; Hruban et al. 2004; Abrams et al. 1996]. Point mutations in the Rab and Rho GTPases are also causal in diverse human diseases affecting pigmentation, immune, and neurologic functions [Houlden et al. 2004; Verhoeven et al 2003; Williams et al. 2000; Bahadoran et al. 2003; and preliminary findings]. Rab and Rho mutants identified in human disease act as dominant negatives either due to a failure to bind GTP or due to inappropriate coupling of the active proteins with downstream effectors. To date, inhibition of Ras and Ras-related proteins has relied largely on altering membrane recruitment with various drugs affecting prenylation [Morgillo F Lee H Y, 2006; Russell R G, 2006; Park, et al. 2002]. Generally, Ras proteins must be farnesylated for proper membrane localization, while Rab and Rho proteins are geranylated. Such strategies lack specificity and are problematic because each of these prenylation machineries is required for the proper function of many Ras superfamily members. Rational drug design has only recently been applied to identify the first two small molecule inhibitors of Rho GTPase family members [Gao, et al. 2004; Nassar et al. 2006]. There are currently no nucleotide binding inhibitors or analogs for any member of the GTPase superfamily, prompting us to undertake a high throughput screen resulting in the identification of novel chemical entitites described herein (FIG. 3-4).

The Rab GTPase subfamily is responsible for regulating membrane transport of proteins and lipids shuttling between various intracellular destinations with individual members governing specific transport events and causal in human disease (FIG. 5-6). Rab7 is a regulator of transport from early to late endosomes and as such is critical for growth factor receptor down-regulation, for control of cell fate through autophagy pathways, nutrient uptake, immune cell regulation, to name a few (FIG. 7). Thus, Rab7 is a late endosome-/lysosome-associated small GTPase. Rab7 plays critical roles in the endocytic processes. Through interaction with its partners (including upstream regulators and downstream effectors), Rab7 participates in multiple regulation mechanisms in endosomal sorting, biogenesis of lysosome (or LRO (lysosome-related organelle)) and phagocytosis. These processes are important in substrate degradation, antigen presentation, cell signaling, cell survival and microbial pathogen infection. Consistently, mutations or dysfunctions of Rab7 result in traffic disorders, which cause various diseases, such as neurologic disorders (Alzheimer's, Downs, sensory neuropathies), bone metabolic disorders, cancer and lipid metabolism or storage diseases (FIGS. 6, 19-20). Rab7 inactivation plays important roles in microbial pathogen infection and survival, as well as in participating in the life cycle of viruses {Zhang, M., Cheng, L., Wang, S. and Wang, T. *Biosci Rep* 2009, 29:193-209).

Hereditary sensory neuropathies (HSNs) are a group of genetically determined peripheral neuropathies with prominent disturbance of the peripheral sensory neurons (FIG. 19). They are characterized by sensory loss, insensitivity to pain, a variable degree of muscle weakness and wasting, as well as autonomic features. Frequent complications are foot ulcerations and infections that may lead to osteomyelitis, followed by necrosis and amputations. Consequently, the hereditary sensory neuropathies have also been termed ulceromutilating neuropathies. On the other hand, in the presence of additional motor weakness, they have been sub-classified among the group of Charcot-Marie-Tooth (CMT) disorders, an autosomal dominant inherited disorder (~1:2500) that causes peripheral neuropathy, foot ulcers and frequently requires amputation. Sporadic and familial cases with different modes of inheritance are known to affect both children and adults. The most prevalent forms of the autosomal dominantly inherited hereditary sensory neuropathies are HSN I and CMT2B. HSN1 is associated with mutations in the SPTLC1 gene, whereas mutations in the Rab7 gene have been identified in CMT2B that result in mutant proteins with single amino acid substitutions of highly conserved residues (FIG. 20). The mutants are thought to disrupt critical functions of Rab7 in shuttling cargo between the neuronal synapse and the soma where signaling to the nucleus occurs. The enumerated roles and disease associations of Rab7 thus provides a rationale to identify small molecules that may functionally modulate Rab7 GTPase. Currently, there are no small molecules directed against any member of the Rab GTPase family despite their diverse cellular functions that ensure normal physiology.

OBJECTS OF THE INVENTION

It is an object of the present invention to provide novel methods of treating or preventing the onset of Rab 7 GTPase associated disorders such as infectious diseases, neuropathies, cancer and lipid metabolism and storage diseases.

It is a more particular object of the present invention to provide novel methods of treating or preventing the onset of Rab 7 GTPase associated hereditary sensory neuropathies (HSNs) such as Charcot-Marie-Tooth type 2B disease.

It is yet another object of the present invention to provide pharmaceutical compositions that are useful in the treatment or prevention of Rab 7 GTPase associated disorders either through the inhibition or activation of Rab7 GTPases function.

It is a further object of the invention to provide novel small molecule based assays and screens that are useful in determining Rab GTPase functional inhibition or activation in vitro and in vivo and that may also aid in determining structure activity relationships of the identified small molecule(s).

It is another object of the current invention to use the small molecule guanine nucleotide binding inhibitor as a template/scaffold for the design of selective and specific competitive guanine nucleotide binding inhibitors for other small GTPase super family members such as Rho-family members (Rae, Rho and Cdc42), Ras, Arf, and Ran. The current scaffold does not inhibit G-protein coupled receptor family of GTPases Inhibition of ATP binding has proved effective for inhibiting kinases through various inhibitors (e.g. imatinib, gefitinib, vandetanib, among others) that are now commonly used to treat many different human diseases and especially multiple cancers.

It is still a further object of the invention to modulate the scaffold such that it can either freeze Rab7 in the constitutively active or constitutively inactive states. Inactivation of mutant or hyperactive proteins would be applicable in neurodegenerative disorders, osteoporosis and cancers. Activation would be applicable in diseases where Rab7 function is insufficient or aberrantly inactivated. Examples include, lipid storage diseases where overexpression of wild-type Rab7 has been shown to be beneficial {Choudhury, A et al., 2002; J. Clin Invest. 109:1541}, osteopetrosis and pathogen-mediated infectious diseases where Rab7 inactivatation enables pathogen survival {Zhang et al., Biosci Reports attached}. A currently FDA approved treatment for Niemann-Pick Type C disease entails cholesterol depletion via central nervous system administration of hydroxypropyl beta cyclodextrin. This compound is highly toxic and systemic administration causes lysis of red blood cells and death in animals. Thus, other improved therapies are still urgently needed.

Any one or more of these and/or other objects of the present invention will be apparent from the drawings and descriptions herein.

BRIEF DESCRIPTION OF THE FIGURES

FIG. 5: Depicts Charcot-Marie-Tooth (CMT) disease mutation in a mouse.
FIGS. 9-13: show the results of equilibrium binding and disassociation studies that established CID1067700 or MLS000673908 as a competitive inhibitor of the nucleotide binding site of the Rab7 GTPase.
FIGS. 14A-B: shows the result of a virtual docking study using Fred OpenEye which determined that CID1067700 fits specifically in the Rab7 GTPase nucleotide binding site. (See also FIGS. 32A-D for views of compound bound to Rab7 in GDP and GTP-bound conformations)

FIG. 30 A-H: Shows that CID1067700 competitively inhibits BODIPY-linked nucleotide binding by wild-type and mutant forms of Rab7. (a-b) CID1067700 (100 nM) does not alter Rab7 wt $B_{max}$ for BODIPY-GTP, but does alter apparent $EC_{50}$ for GTP (filled squares); observed as a rightward shift of log plot of BODIPY-GTP binding by Rab7 wt. (c-d) CID1067700 (200 nM) does not alter Rab7 wt $B_{max}$ for BODIPY-GDP; but does alter apparent $EC_{50}$ for GDP (filled triangles); observed as rightward shift of log plot of BODIPY-GDP binding by Rab7 wt. (e-f) CID1067700 CID1067700 (100 nM) does not alter constitutively active Rab7Q67L mutant $B_{max}$ for BODIPY-GTP, but does alter apparent $EC_{50}$ for GTP (filled squares); observed as a rightward shift of log plot of BODIPY-GTP binding by Rab7Q67L. (g-h) CID1067700 (200 nM) does not alter Rab7T22N $B_{max}$ for BODIPY-GDP; but does alter apparent $EC_{50}$ for GDP (filled triangles); observed as rightward shift of log plot of BODIPY-GDP binding by Rab7T22N. In all experiments, equilibrium binding reactions performed in 1% DMSO served as the controls (open circles).

FIG. 31 A-D: Shows that CID1067700 has no effect on the rate of release of bound BODIPY-linked nucleotide by wild type Rab7 under equilibrium binding conditions. (A) Rab7 was pre-incubated with BODIPY-GTP (100 nM) for 2 h 15 min at 4° C., conditions that allow nucleotide binding to equilibrium. Dissociation assays were initiated by dilution +/− the addition of either CID1067700 (10 µM) or unlabeled GDP (10 µM) and decrease in fluorescence due to nucleotide dissociation was measured in real time. (B) Two-phase exponential analysis of a, normalized by subtraction of dilution only values. (C). Rab7 was preincubated with BODIPY-GDP (40 nM) for 2 h 15 min at 4° C. as for (A). Dissociation assays were initiated by dilution+/−CID1067700 (10 µM) or unlabeled GDP (10 µM) and decrease in fluorescence due to nucleotide dissociation was measured in real time. (D) Single phase exponential analysis of c, normalized by subtraction of dilution only values.

FIG. 33 A-C: Shows a structure activity relationship which identifies the importance of linker and R-groups in inhibitory activity of CID1067700. (A). CID1067700 included for comparison with derivatives of CID1067700. (B) Nanomolar concentrations of CID46916263 derivative with only single methyl replacement on the pyran group and intact carbamothioylamino linker inhibit Rab7 wt protein nucleotide binding; BODIPY-GTP (100 nM, filled squares) and BODIPY-GDP (40 nM, filled triangles). (C) Nanomolar concentrations of CID46916266 derivative with only two methyl replacement on the pyran group and intact carbamothioylamino linker inhibit Rab7 wt protein nucleotide binding; BODIPY-GTP (100 nM, filled squares) and BODIPY-GDP (40 nM, filled triangles). (D) Nanomolar concentrations of CID46916265 derivative with only alteration of the thiourea moiety of the carbamothioylamino linker inhibit Rab7 wt protein nucleotide binding; BODIPY-GTP (100 nM, filled squares) and BODIPY-GDP (40 nM, filled triangles). (E) Nanomolar concentrations of CID1251121 derivative with alteration of the carboxylic acid group only do not show any activity towards inhibition of nucleotide binding by Rab7 wt protein.

SUMMARY OF THE INVENTION

Figure 1:
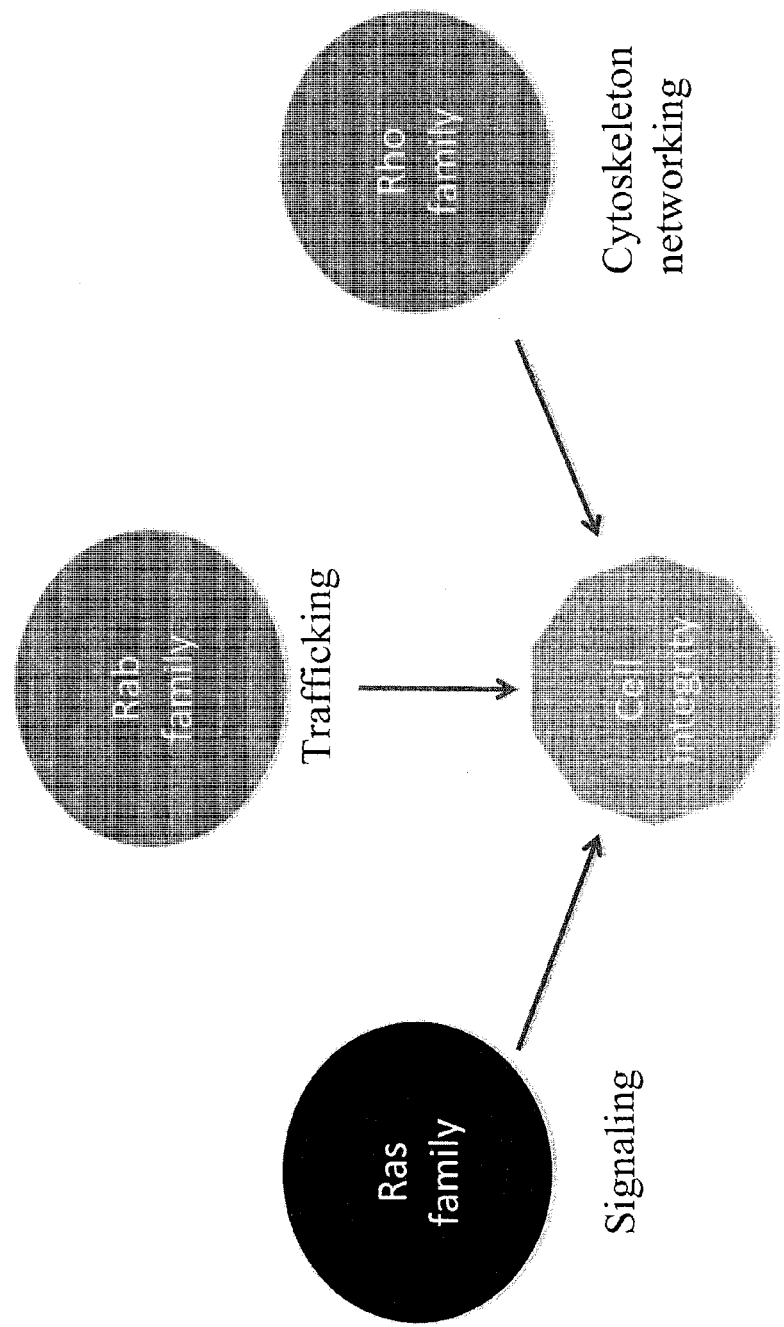
FIG. 1: Illustrates that small GTPase regulate diverse cellular functions.
Figure 2:
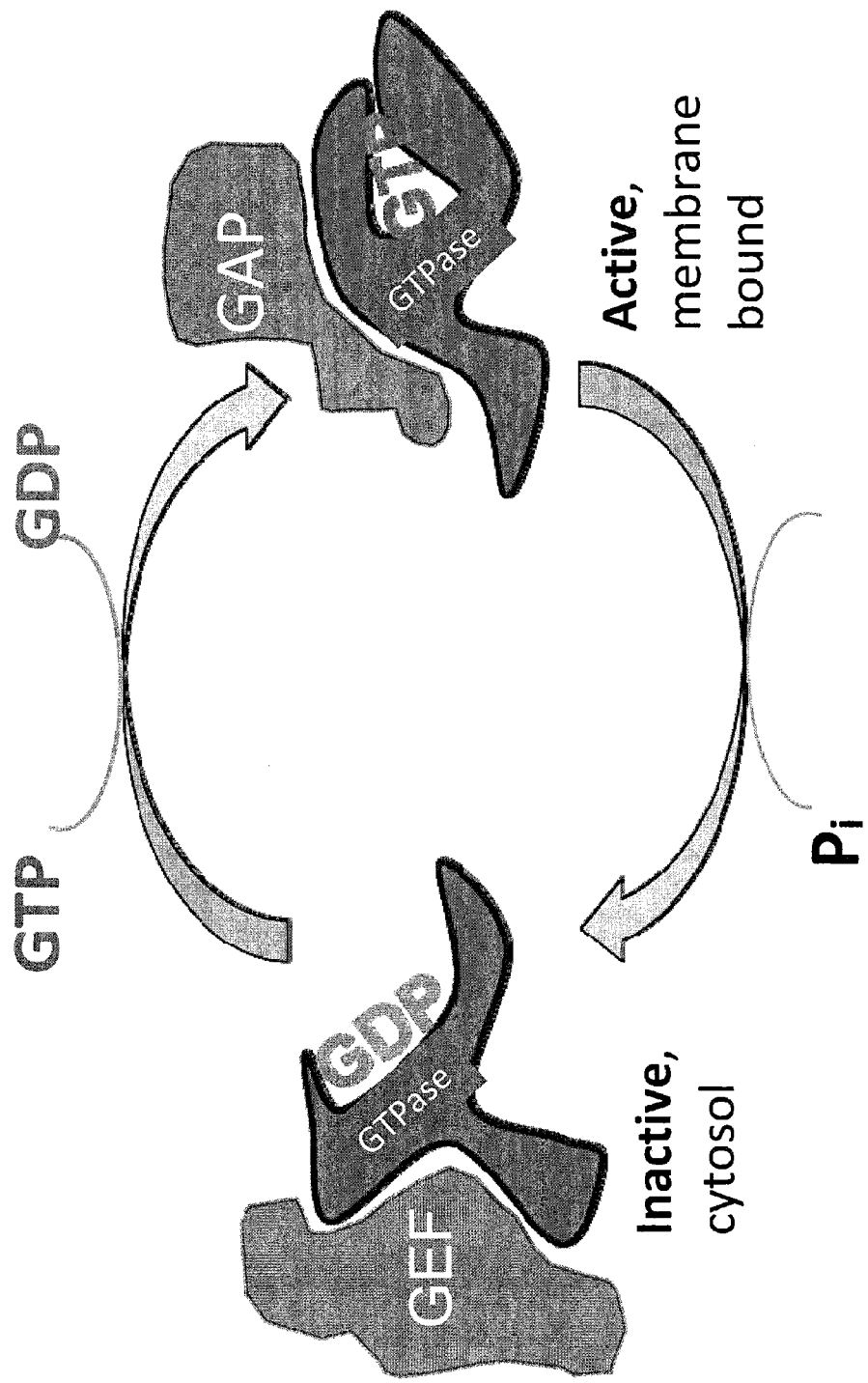
FIG. 2: Illustrates the GTPase activation cycle.

The invention relates to small molecule inhibitors or activators of Rab7 GTPase to treat or prevent the onset of Rab7 GTPase associated disorders such as neuropathies, cancer and lipid metabolism disease. In one aspect, methods of treatment proposed in the invention are used to treat or prevent the onset of hereditary sensory neuropathies such as Charcot-Marie-Tooth type 2B disease. Related pharmaceutical compositions, assays, and drug screens are also provided.

In the first aspect of the present invention, the invention provides a method of treating or preventing the onset of a Rab7 GTPase associated disorder, the method comprising administering to a subject suffering from, or at risk of developing a Rab7 GTPase associated disorder, a compound having the chemical structure (I):

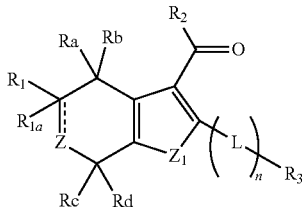

wherein
$R_1$ is H, a $C_1$-$C_6$ hydrocarbon, preferably a linear branched or cyclic alkyl group (even more preferably a methyl) which is optionally substituted, a $(CH_2)_j$—$C_1$-$C_6$ ether or thioether group which is optionally substituted, a $(CH_2)_j$—$C_1$-$C_6$ acyl group which is optionally substituted, a $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, an optionally substituted $(CH_2)_n$-thioamide group, an optionally substituted $(CH_2)_n$-aryl group or an optionally substituted $(CH_2)_n$-heterocyclic group, or together with $R_{1a}$ form a $C_3$-$C_7$ (preferably a $C_5$ or $C_6$) cycloalkyl group;

$R_{1a}$ is absent, H or an optionally substituted $C_1$-$C_6$ preferably a $C_1$-$C_3$ alkyl group, preferably H or methyl or together with $R_1$ form a $C_3$-$C_7$ (preferably a $C_5$ or $C_6$) cycloalkyl group;

j is 1, 3, 4, 5 or 6, preferably 1, 2 or 3;

n is 1, 2, or 3, preferably 1 or 2;

Z is O, S, =C—$R^N$, —$CR^N R^N$, =N— or N—$R^N$, preferably O or S, more preferably O;

$Z_1$ is O, S or N—$R^N$, preferably O or S, more preferably S;

$R^N$ is H or a $C_1$-$C_3$ alkyl group;

$R_a$, $R_b$, $R_c$, and $R_d$ are the same or different and are independently H, halo, or an optionally substituted $C_1$-$C_6$ hydrocarbon, including an alkyl group (preferably $R_a$, $R_b$, $R_c$, and $R_d$ are each H), preferably H, halo (F, Cl, Br or I, preferably F or Cl) or methyl;

$R_2$ is H, —OH, a $C_1$-$C_6$ hydrocarbon, preferably a linear branched or cyclic alkyl group, a $(CH_2)_j$—$C_1$-$C_6$ ether or thioether group which is optionally substituted, a O—$C_1$-$C_{12}$ alkyl group (thus forming a carboxy ester), a $(CH_2)_j$—$C_1$-$C_6$ acyl group which is optionally substituted, a $(CH_2)_j$—$NR^1R^2$ group (wherein $R^1$ and $R^2$ are each independently H or a $C_1$-$C_6$ alkyl group optionally substituted with halo or at least one hydroxyl group), or an optionally substituted $(CH_2)_n$-amide group;

$(L)_n$ is a linker group according to the chemical structure:

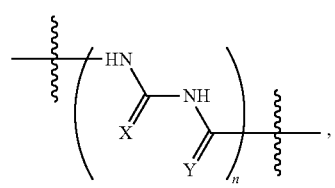

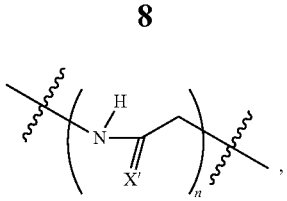

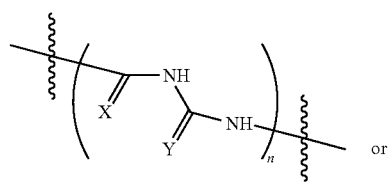

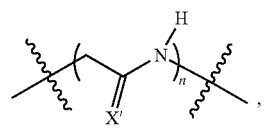

or an (oligo)ethylene glycol group comprising 1, 2 or 3 ethylene glycol units;

X, X' and Y are the same or different and are O or S, preferably O;

$R_3$ is aryl (preferably an optionally substituted phenyl group), a ($C_0$-$C_6$ hydrocarbon)-aryl, preferably a —$C_1$-$C_6$ alkyl-aryl, —O-aryl, or a —$C_0$-$C_6$ alkyl-het, wherein het is a 5- or 6-membered heteroaromatic ring containing from 1 to 4 heteroatoms independently selected from N, O and S, and aryl and het are optionally fused with a benzene ring, and are further each optionally substituted or a pharmaceutically acceptable salt, solvate or polymorph thereof.

In certain preferred embodiments, compounds that are used in the present invention have the following chemical structure (Ia):

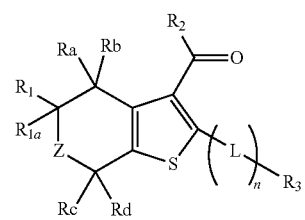

wherein
$R_1$ is H, a $C_1$-$C_6$ hydrocarbon, preferably a linear branched or cyclic alkyl group (even more preferably a methyl) which is optionally substituted, a $(CH_2)_j$—$C_1$-$C_6$ ether or thioether group which is optionally substituted, a $(CH_2)_j$—$C_1$-$C_6$ acyl group which is optionally substituted, $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, an optionally substituted $(CH_2)_n$-thioamide group, an optionally substituted $(CH_2)_n$-aryl group or an optionally substituted $(CH_2)_n$-heterocyclic group;

$R_{1a}$ is H or an optionally substituted $C_1$-$C_3$ alkyl group, preferably H or methyl;

j is 1, 2, 3, 4, 5 or 6, preferably 1, 2 or 3;

n is 1, 2, or 3, preferably 1 or 2;

Z is O, S, $CH_2$, =N— or N—$R^N$, preferably O or S, more preferably O;

$Z_1$ is O, S or N—$R^N$, preferably O or S, more preferably S;

$R^N$ is H or a $C_1$-$C_3$ alkyl group;

$R_a$, $R_b$, $R_c$, and $R_d$ are the same or different and are independently H, halo, or a $C_1$-$C_6$ hydrocarbon (preferably $R_a$, $R_b$, $R_c$, and $R_d$ are each H, methyl or halo);

$R_2$ is H, —OH, a $C_1$-$C_6$ hydrocarbon, preferably a linear branched or cyclic alkyl group, a $(CH_2)_j$—$C_1$-$C_6$ ether or thioether group which is optionally substituted, a O—$C_1$-$C_{12}$ alkyl group, $(CH_2)_j$—$C_1$-$C_6$ acyl group which is optionally substituted, a $(CH_2)_j$—$NR^1R^2$ group (wherein $R^1$ and $R^2$ are each independently H or a $C_1$-$C_6$ alkyl group optionally substituted with halo or at least one hydroxyl group), or an optionally substituted $(CH_2)_n$-amide group, preferably $R_2$ is a O—$C_1$-$C_6$ alkyl;

$(L)_n$ is a linker group according to the chemical structure:

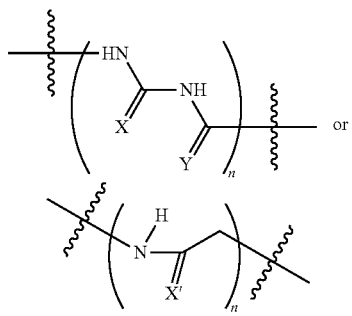

or an (oligo)ethylene glycol group comprising 1, 2 or 3, ethylene glycol groups, preferably 1 or 2 ethylene glycol groups;

X, X' and Y are the same or different and are O or S, X' is preferably O;

$R_3$ is aryl (preferably an optionally substituted phenyl), a ($C_0$-$C_6$ hydrocarbon)-aryl, preferably a —$C_1$-$C_6$ alkyl-aryl, or —O-aryl, or a pharmaceutically acceptable salt, solvate or polymorph thereof.

In one aspect, methods of treatment of the invention use a compound of Formula (I) or (Ia) in which:

$R_1$ is a $C_1$-$C_6$ hydrocarbon, preferably a methyl group;

$R_{1a}$ is H or a methyl group;

n is 1 or 2;

Z is O;

$R_a$, $R_b$, $R_c$ and $R_d$ are the same or different and are independently H, methyl or halo;

X and Y are independently O and S;

$R_2$ is H, —OH, a $C_1$-$C_6$ hydrocarbon, preferably a linear, branched, or cyclic alkyl group, a $(CH_2)_j$—$C_1$-$C_6$ ether, or thioether group which is optionally substituted or a O—$C_1$-$C_6$ alkyl group; and $R_3$ is aryl (preferably an optionally substituted phenyl), a ($C_0$-$C_6$ hydrocarbon)-aryl, preferably a —$C_1$-$C_6$ alkyl-aryl, or —O-aryl.

In another aspect, methods of treatment of the invention use a compound of Formula (I) or (Ia) in which:

$R_1$ is a $C_1$-$C_6$ hydrocarbon, preferably methyl;

$R_{1a}$ is H or methyl;

j is 1, 2, or 3;

n is 1 or 2;

Z is O;

$R_a$, $R_b$, $R_c$, and $R_d$ are the same or different and are independently H, methyl or halo;

X and Y are independently O and S;

$R_2$ is H, —OH, a linear, branched, or cyclic alkyl group, a $(CH_2)_j$—$C_1$-$C_6$ ether, or thioether group which is optionally substituted or a O—$C_1$-$C_6$ alkyl group; and $R_3$ is optionally substituted phenyl, a —$C_1$-$C_6$ alkyl-aryl, or —O-aryl.

In another aspect, methods of treatment of the invention use a compound of Formula (I) or (Ia) in which:

$R_1$ is methyl;

$R_{1a}$ is methyl;

j is 1, 2, or 3;

n is 1;

Z is O;

$R_a$, $R_b$, $R_c$, and $R_d$ are the same or different and are independently H, methyl or halo;

X and Y are independently O and S;

$R_2$ is H, —OH, a linear, branched, or cyclic alkyl group, or a $(CH_2)_j$—$C_1$-$C_6$ ether; and $R_3$ is an optionally substituted aryl.

In another aspect, methods of treatment of the invention use a compound of Formula (I) or (Ia) in which:

$R_1$ is methyl;

$R_{1a}$ is methyl;

n is 1;

Z is O;

$R_a$, $R_b$, $R_c$, and $R_d$ are the same or different and are independently H or halo;

X and Y are independently O and S;

$R_2$ is H, —OH, or a linear, branched, or cyclic alkyl group; and $R_3$ is an optionally substituted phenyl.

In another aspect, methods of treatment of the invention use a compound of Formula (I) or (Ia) in which:

$R_1$ is dimethyl;

n is 1;

Z is O;

$R_a$, $R_b$, $R_c$, and $R_d$ are the same or different and are independently H or halo;

X is S and Y is O;

$R_2$ is H, —OH, O—$C_1$-$C_6$ alkyl, or a linear, branched, or cyclic alkyl group; and $R_3$ is an optionally substituted phenyl.

In another aspect, methods of treatment of the invention use a compound of Formula (I) or (Ia) in which:

$R_1$ is methyl;

$R_{1a}$ is methyl;

n is 1;

Z is O;

$R_a$, $R_b$, $R_c$, and $R_d$ are each H;

X is O and Y is S;

$R_2$ is H, —OH, O, O—$C_1$-$C_6$ alkyl or a linear, branched, or cyclic alkyl group; and $R_3$ is an optionally substituted phenyl.

In another aspect, methods of treatment of the invention use a compound of Formula (I) or (Ia) in which:

$R_1$ is methyl;

$R_{1a}$ is methyl;

n is 1;

Z is O;

$R_a$, $R_b$, $R_c$, and $R_d$ are each H or methyl;

X is S and Y is O;

$R_2$ is H, or —OH; and $R_3$ is an optionally substituted phenyl.

In another aspect, methods of treatment of the invention use a compound of Formula (I) or (Ia) in which:
$R_1$ is dimethyl;
n is 1 or 2;
Z is O;
$R_a$, $R_b$, $R_c$, and $R_d$ are each H;
X is O and Y is S;
$R_2$ is H, or —OH; O—$C_1$-$C_3$ alkyl and
$R_3$ is an optionally substituted phenyl.

In a further aspect of the methods of treatment of the invention, the compound is according to formula II:

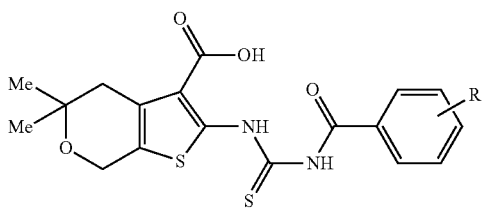

II

Where R is H, a halogen (preferably F or Br), a —O—($C_1$-$C_3$) alkyl (alkoxy group, preferably OMe) or an optionally substituted $C_1$-$C_3$ alkyl (preferably including a trifluoromethyl group or an alkyl group with one or two hydroxyl groups as substituents) or a pharmaceutically acceptable salt thereof. The substituents may be positioned on the phenyl group at ortha, meta or para positions, with the halogens preferably (preferably F) at ortho, meta or para positions and an alkoxy (preferably methoxy) or methyl at ortho-meta- or para positions.

In still a further aspect of the methods of treatment of the invention, the compound is according to formula III:

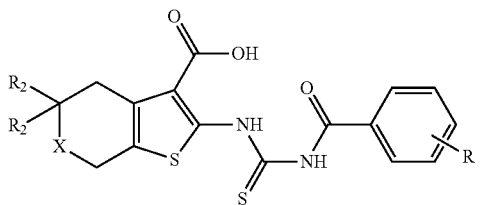

III

Where $R_1$ and $R_2$ are each independently H or a $C_1$-$C_6$ alkyl group (preferably methyl), or together form a $C_3$-$C_7$ cycloalkyl group;
X is O or $CH_2$ (preferably O) and R is H, a halogen (F, Cl, Br, I, preferably F or Br), a —O—($C_1$-$C_3$) alkyl (alkoxy group, preferably OMe) or an optionally substituted $C_1$-$C_3$ alkyl (preferably including a trifluoromethyl group or an alkyl group with one or two hydroxyl groups as substituents) or a pharmaceutically acceptable salt thereof. The substituents may be positioned on the phenyl group at ortho, meta or para positions, with the halogens preferably at ortho, meta or para positions (preferably meta or para) and the alkoxy and alkyl groups at ortho, meta or para (preferably, meta or para) positions.

In a further preferred aspect of the methods of treatment of the invention, the compound of formula (I) is PubChem. No. CID1067700 (2-(benzoylcarbamothioylamino)-5,5-dimethyl-4, 7-dihydrothieno[2,3-c]pyran-3-carboxylic acid):

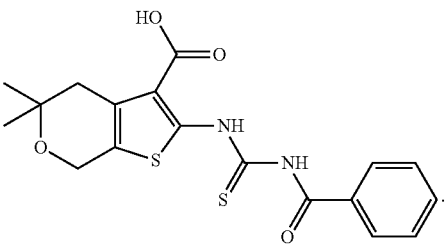

PubChem No. CID 1067700

Or a $C_1$-$C_3$ carboxyl ester, preferably a methyl ester.

Figure 28:
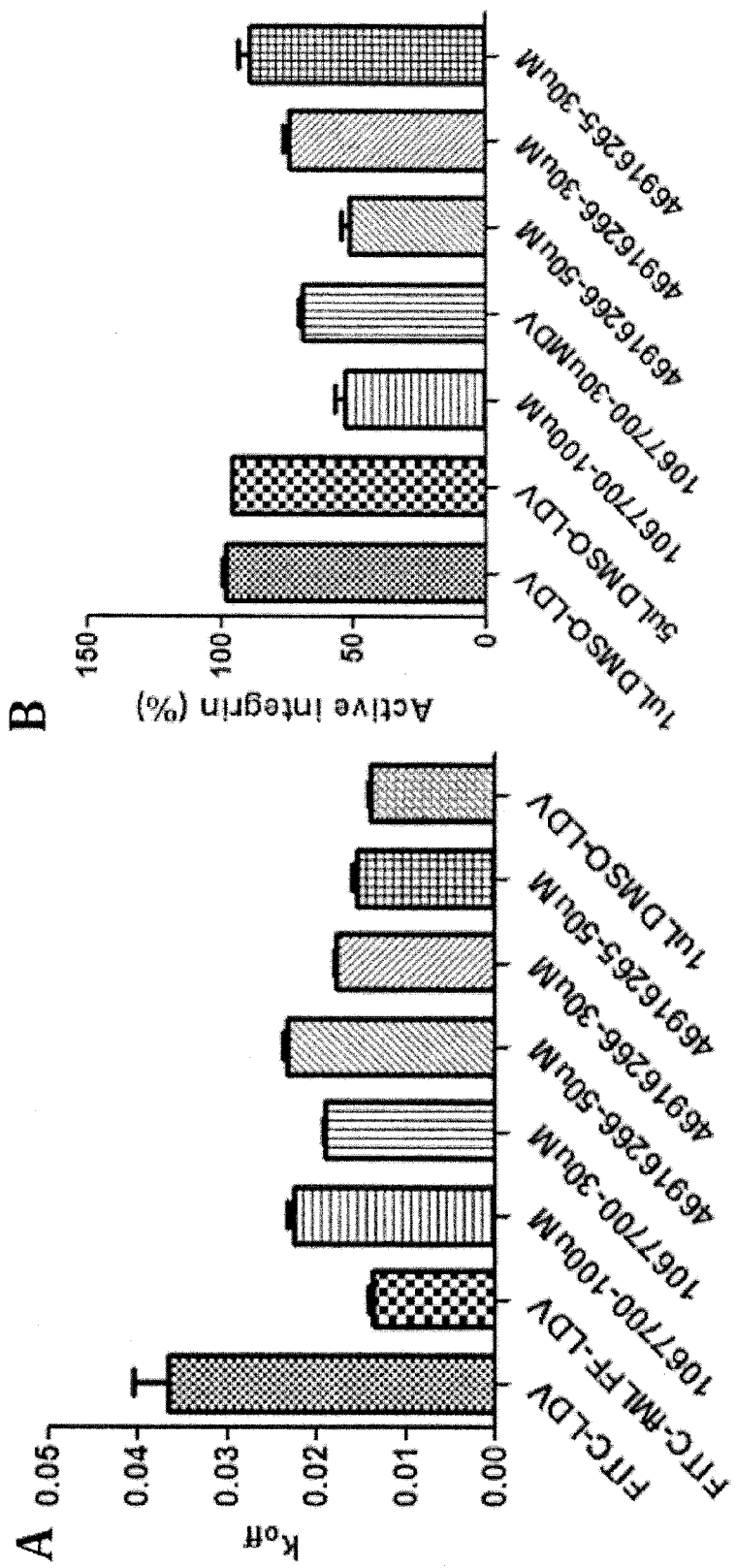
FIG. 28: Shows the dissociation rates and percentage of active integrins A. The dissociation curve was fitted with a single phase exponential (Equation 2) to obtain $k_{off}$. B. The dissociation curve was fitted with two phase exponential, Equation 3, to obtain the percentage of active VLA-4 according to equation 4. $k_h$ and $k_1$ are fixed at $0.014\,s^{-1}$ and $0.036\,s^{-1}$, respectively, as determined in separate experiments.
Figure 29:
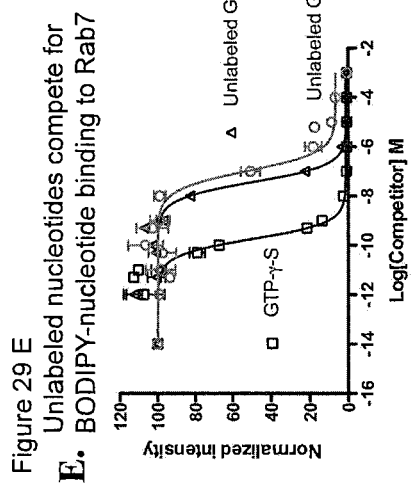
FIG. 29 A-E: Identifies CID1067700 or ML000673908 as a pan GTPase inhibitor using highthroughput screening on small GTPases. (A) Schematic diagram of the bead based assay used to measure fluorescent guanosine triphosphate (GTP) binding by flow cytometry to glutathione-S-transferase (GST)—GTPase chimeras immobilized on GSH-beads. For HTS beads of varying red fluorescence intensities were used as identifiers for individual protein-conjugated bead sets. The assay is sensitive to both increases and decreases in bead associated fluorescence and was used to identify both activators and inhibitors in a single screen. (B) Chemical structure of CID1067700 an inhibitor of nucleotide binding with (C) activity against multiple GTPases measured as residual nucleotide binding activity (BODIPY-GTP, 100 nM) in the presence of increasing concentrations of compound. (D) Nanomolar concentrations of CID1067700 inhibit Rab7 wt protein nucleotide binding; BODIPY-GTP (100 nM, filled squares) and BODIPY-GDP (40 nM, filled triangles). (E) Unlabeled GTP, GDP and GTP-γ-S effectively compete BODIPY-GTP binding.

CID1067700 (FIG. 24) is a pan inhibitor of small molecular weight GTPases and the first molecule with any in vitro effect on Rab GTPases. The compound has nanomolar potency and 90% efficacy against the Rab7 GTPase (FIGS. 8, 26-29), as measured using in vitro assays, as well as in cell-based assays, and as described further below. The compound also showed some efficacy against other small GTPases of the Rho-family, Ras and Rab family (FIG. 29C). The compound was identified by screening the NIH Roadmap of more than three hundred thousand unique chemical compounds using an in vitro BODIPY-GTP binding assay, as explained hereinafter. Active small molecules were identified by scoring for a greater than 20% increase or decrease in fluorescent GTP-binding relative to untreated controls. Hence the scaffold in conjunction with known GTPase structures and rationale drug design may serve as a template for generating selective derivatives with greater efficacy and potency on individual small GTPase subfamilies such as Arf, Rho-family, Ras, and Ran all of which are associated with human diseases from cancers to ciliopathies affecting kidney, pancreas, liver and vision.

Figure 18A:
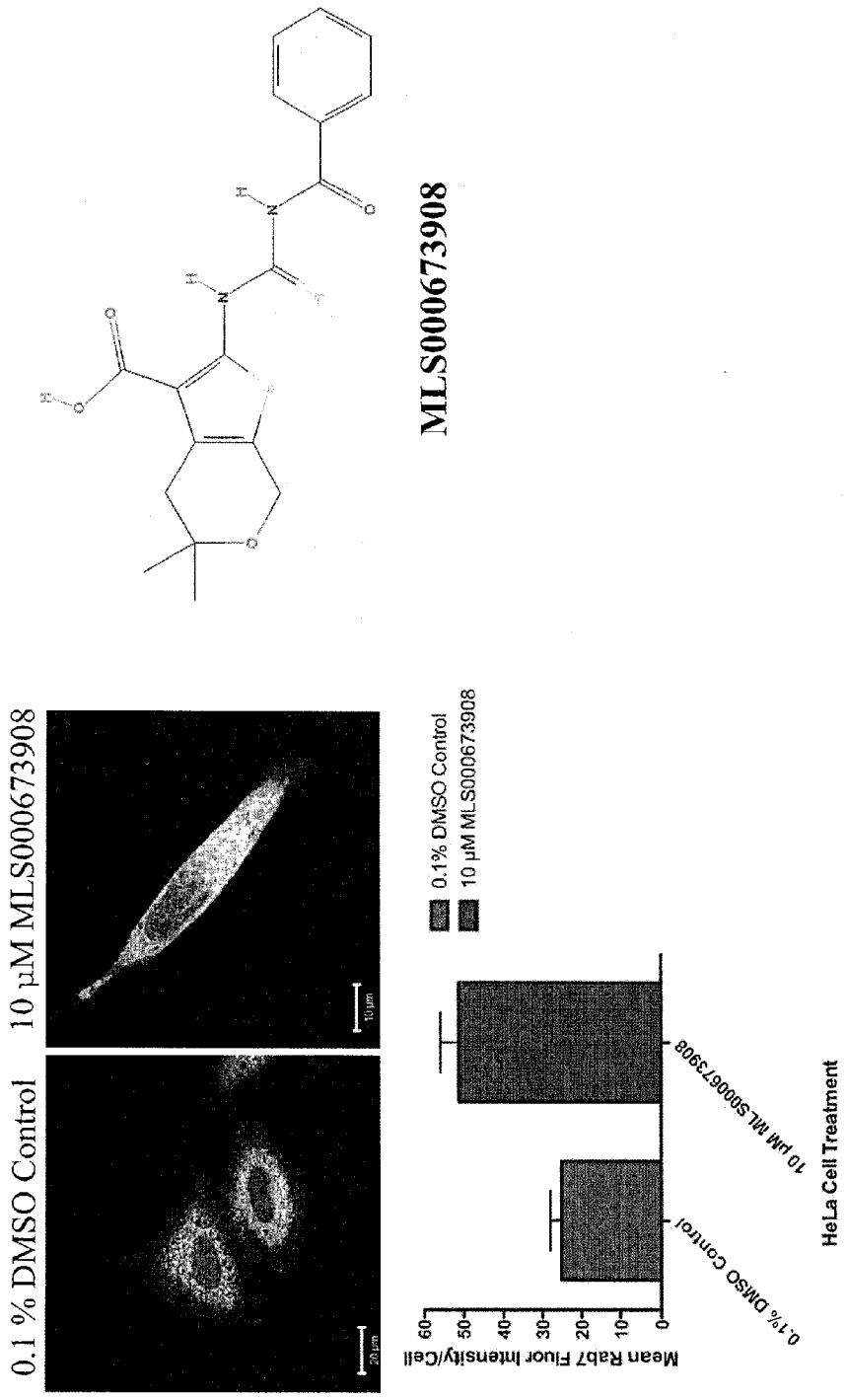
FIG. 18 A-C: Illustrates that CID1067700 changes Rab7 activity in cell based assays. (A) increased endosomal membrane localization of Rab7 in HeLa cells implies activation of Rab7, which can occur if bound compound forces the protein to adopt the active GTP-bound state. (B-C) decreased growth factor receptor (EGFR) degradation in human cervical carcinoma cells overexpressing (B) Rab7 (HeLa-Rab7 wt) treated with 100 μM CID1067700 and (C) human keratinocytes (SCC-12F) treated with 10-100 μM CID1067700 implies inactivation of Rab7 activity in lysosomal transport.

Based on in vitro analyses described below, CID1067700 behaves like a competitive inhibitor (FIGS. 8, 29D, 30a-e) and docking studies show the compound can be accommodated in the nucleotide binding pocket of Rab7 in both the GTP-bound and GDP-bound conformations (FIGS. 14, 32a-h). In some cell based assays, CID1067700 may mimic the activated state of Rab7 and increase membrane bound Rab7 (FIG. 18A). This can occur by CID1067700 binding to the nucleotide pocket and promoting the transition of the Rab7 GTPase into the GTP-bound conformation. In other cell-based assays the compound was found to act as an inhibitor of epidermal growth factor receptor degradation, a process dependent on active Rab7 for transport to lysosomes and implying Rab7 inactivation (FIG. 18B-C). Hence, the scaffold through further development of structure activity relationships can serve as a template for inhibition of function by favoring Rab7 in the inactive GDP-bound conformation or activation of function by favoring the Rab7 in the active GTP-bound conformation.

Figure 20:
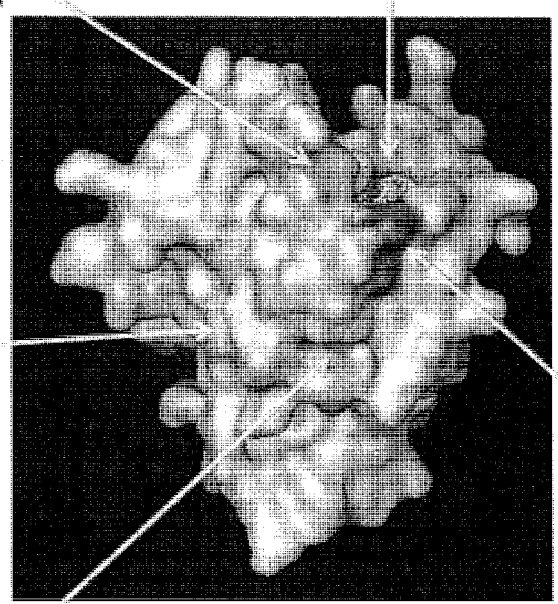
FIG. 20: Illustrates the four Rab7 point mutants associated with CMT2B.
Figure 21:
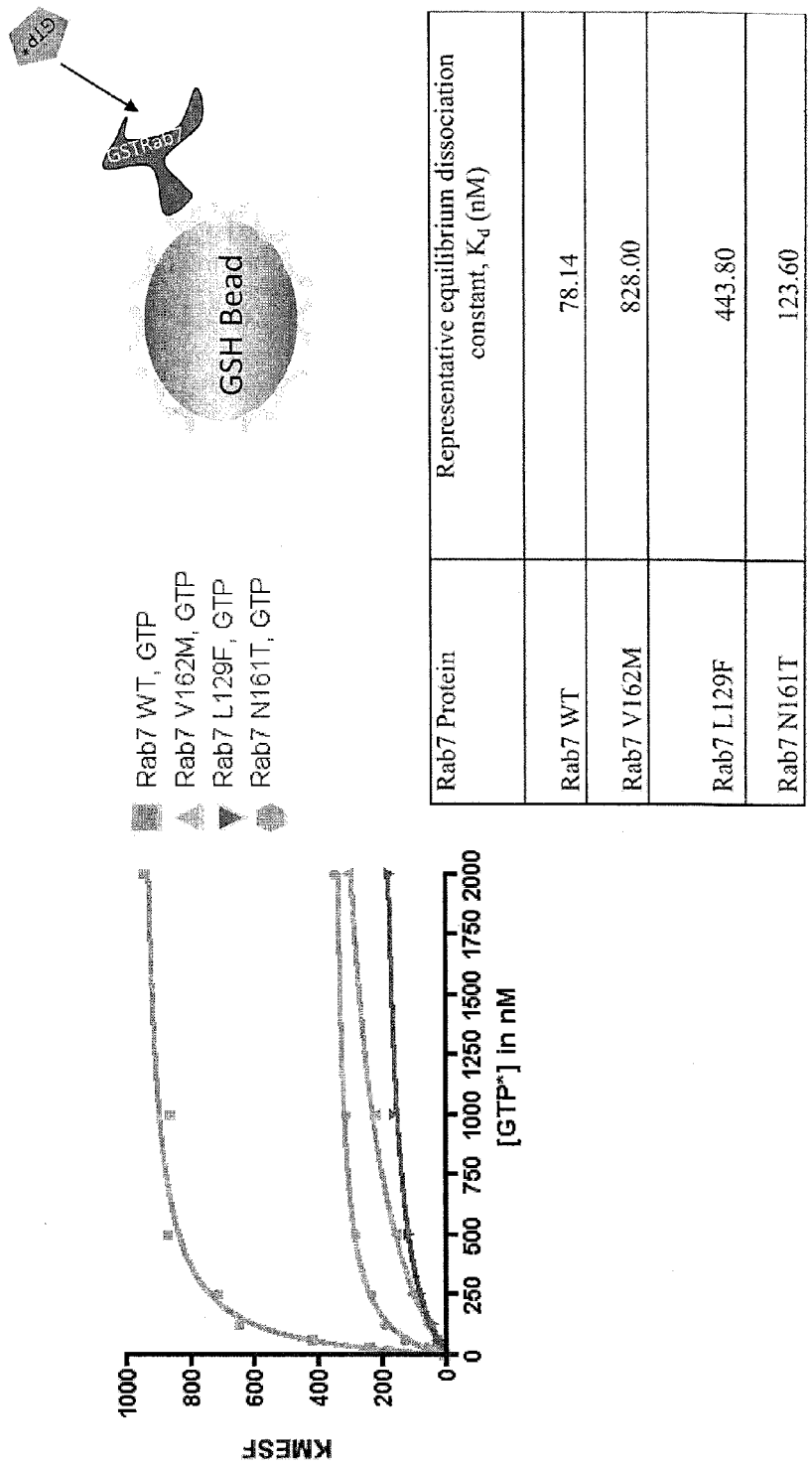
FIG. 21: Compares GTP binding affinity of Rab7WT and three of the Rab7 mutants associated with CMT2B disease.
Figure 22:
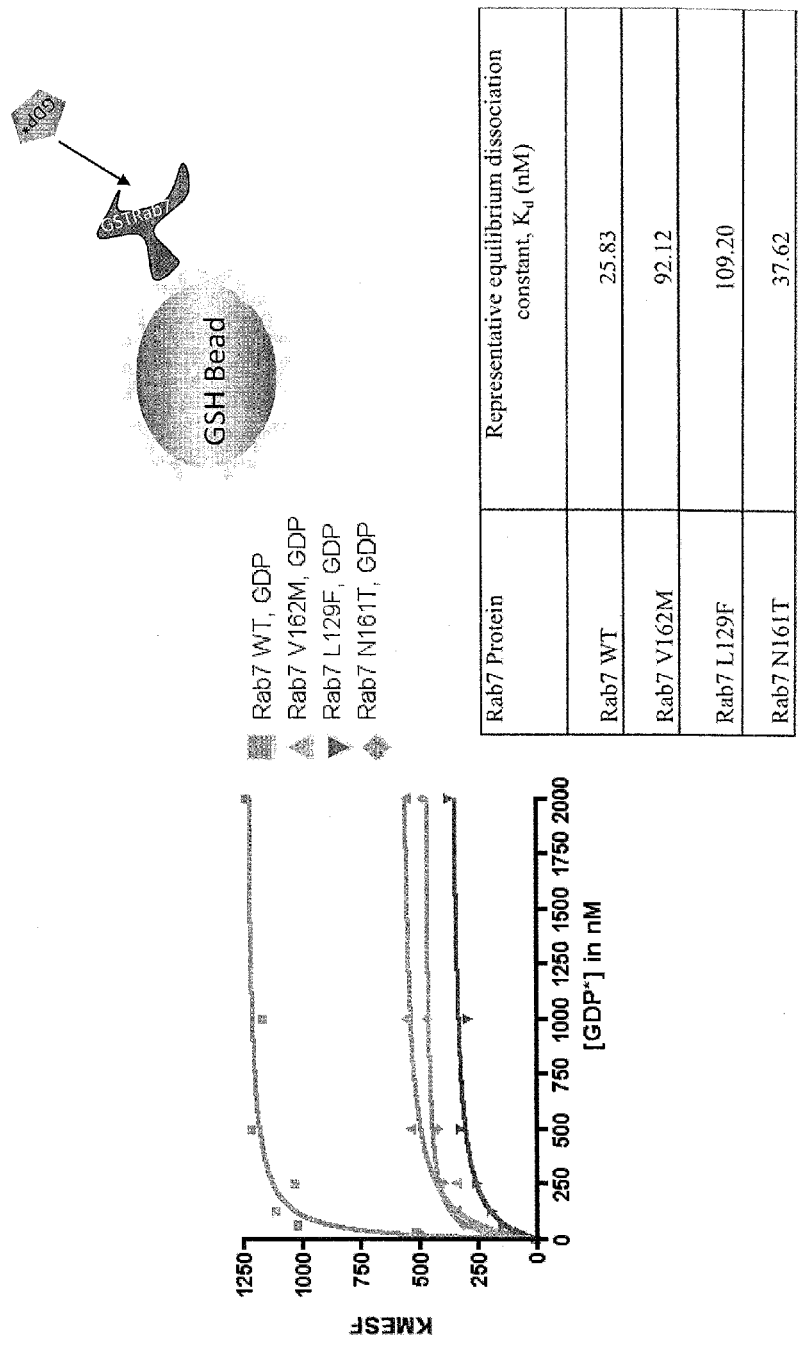
FIG. 22: Compares GDP binding affinity of Rab7WT and three of the Rab7 mutants associated with CMT2B disease.

Charcot-Marie-Tooth type 2B disease patients retain a wild type protein (FIGS. 20-22). The small molecules used in the methods of treatment of the invention would be effective either by increasing the activity of the haplo insufficient wild-type protein or by inactivating the mutant protein (which may act as a dominant negative) and prove particularly useful in treating Charcot-Marie-Tooth type 2B disease.

Figure 7:
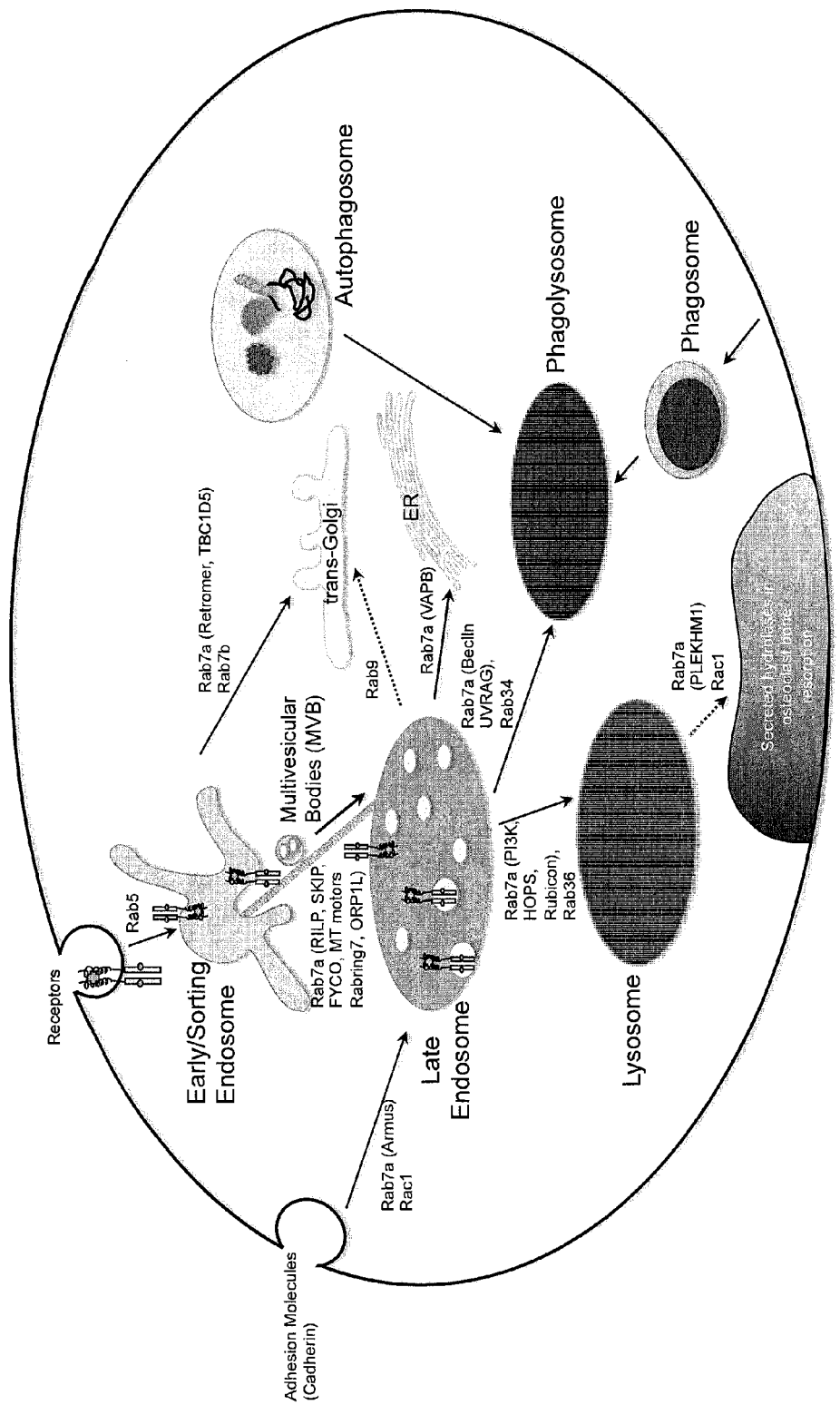
FIG. 7: Illustrates the role of Rab7 in the regulation of endocytic pathway.

In other aspects, the present invention relates to the treatment of other diseases where proper Rab7 function is crucial as otherwise described herein (FIG. 7). Rab7 is required for proper lipid metabolism defects in which lead to lipid storage disorders. Rab7 is also important in bone resorption defects in which lead to osteoporosis or osteopetrosis. Rab7 is modulated by intracellular pathogens that underlie infectious diseases.

Figure 15:
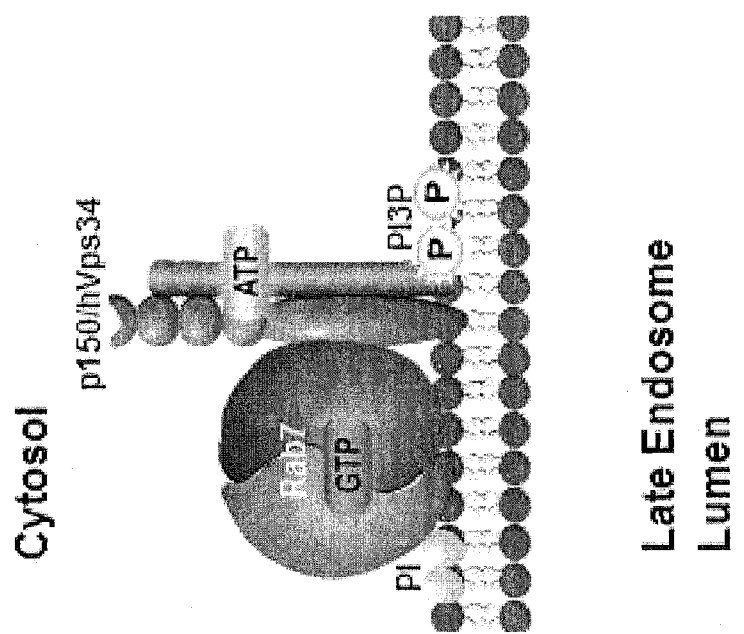
FIG. 15: Illustrates that Rab7 function in endocytosis depends on protein-protein interactions.
Figure 16:
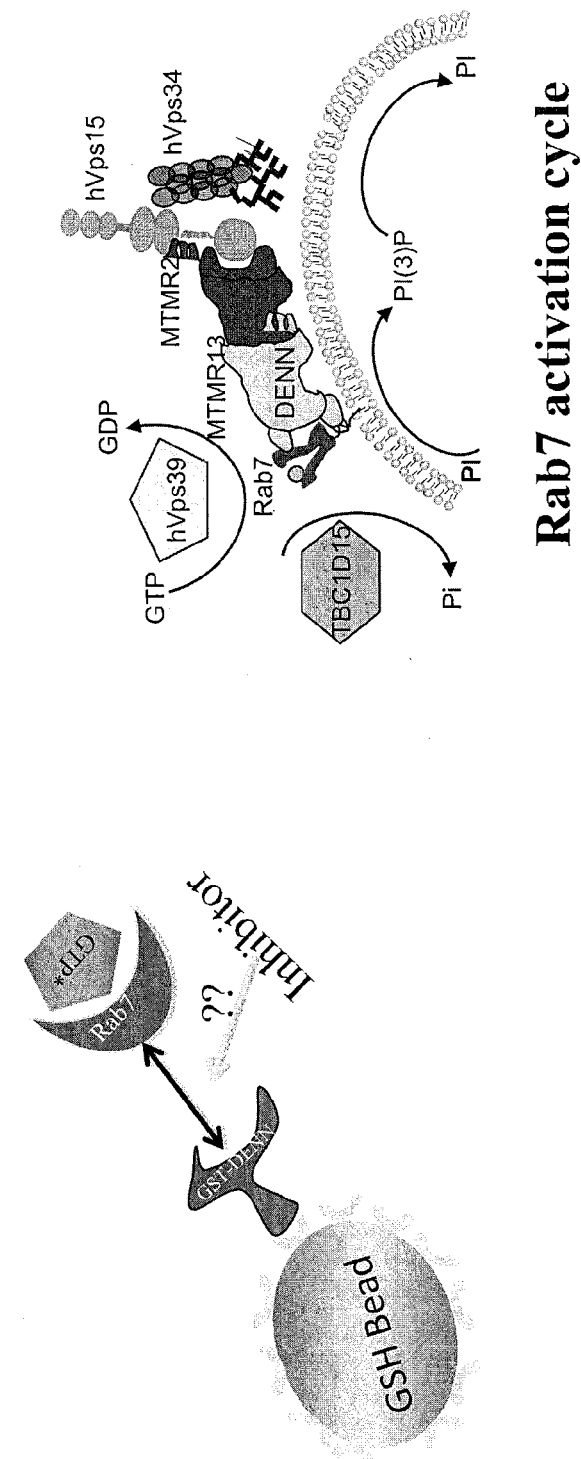
FIG. 16: Illustrates how CID1067700 or MLS000673908 could modulate Rab7WT protein-protein interactions in vivo.
Figure 17A:
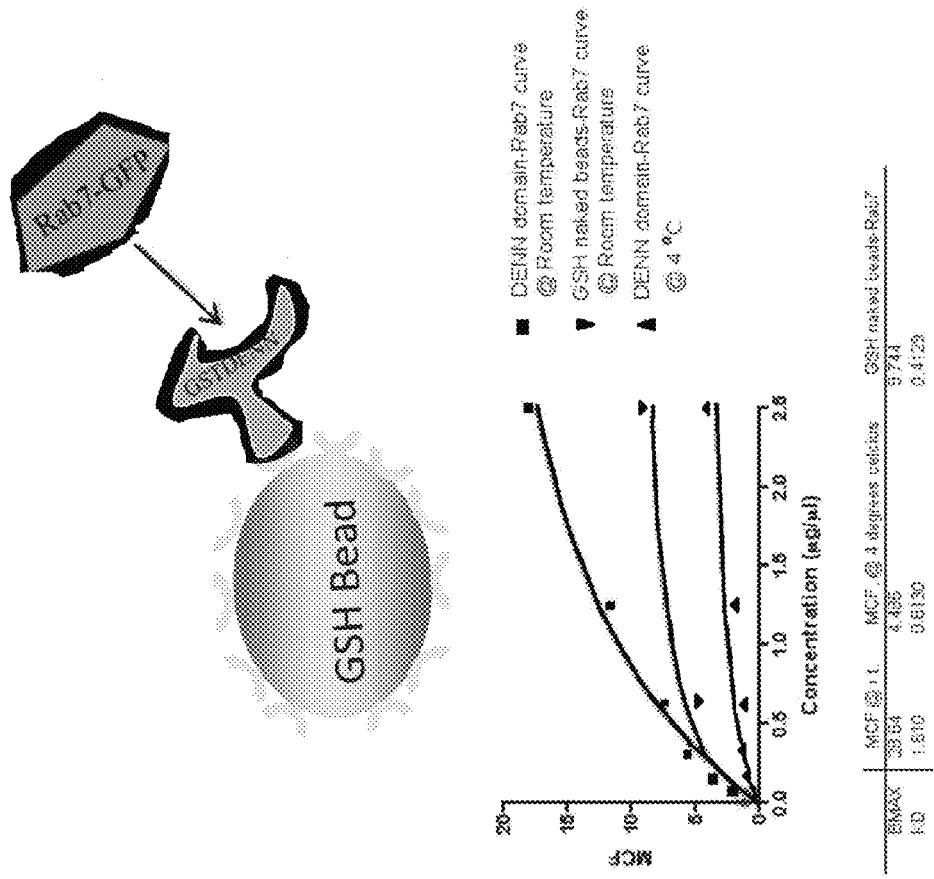
FIGS. 17A-D: Illustrates how Rab7 nucleotide interaction and hydrolysis and Rab7 protein-protein interactions (with MTMR13 and RILP) can be measured by flow cytometry based assays and can be used to test small molecule activity in vitro. (A) Rab7-GFP interaction with MTMR13 GST-DENN domain. (B) BODIPY-GTP binding to His-Rab7 immobilized on nickel (Ni) beads. (C) His-Rab7 binding to effector Rab7-interacting lysosomal protein (RILP) is GTP-dependent and inhibited by CID1067700. (D) His-Rab7-GFP binding to GST-RILP detects GTP-hydrolysis due to dissociation of Rab7-GFP upon hydrolysis and conversion to GDP-bound conformation, which can not bind RILP.
Figure 17B:
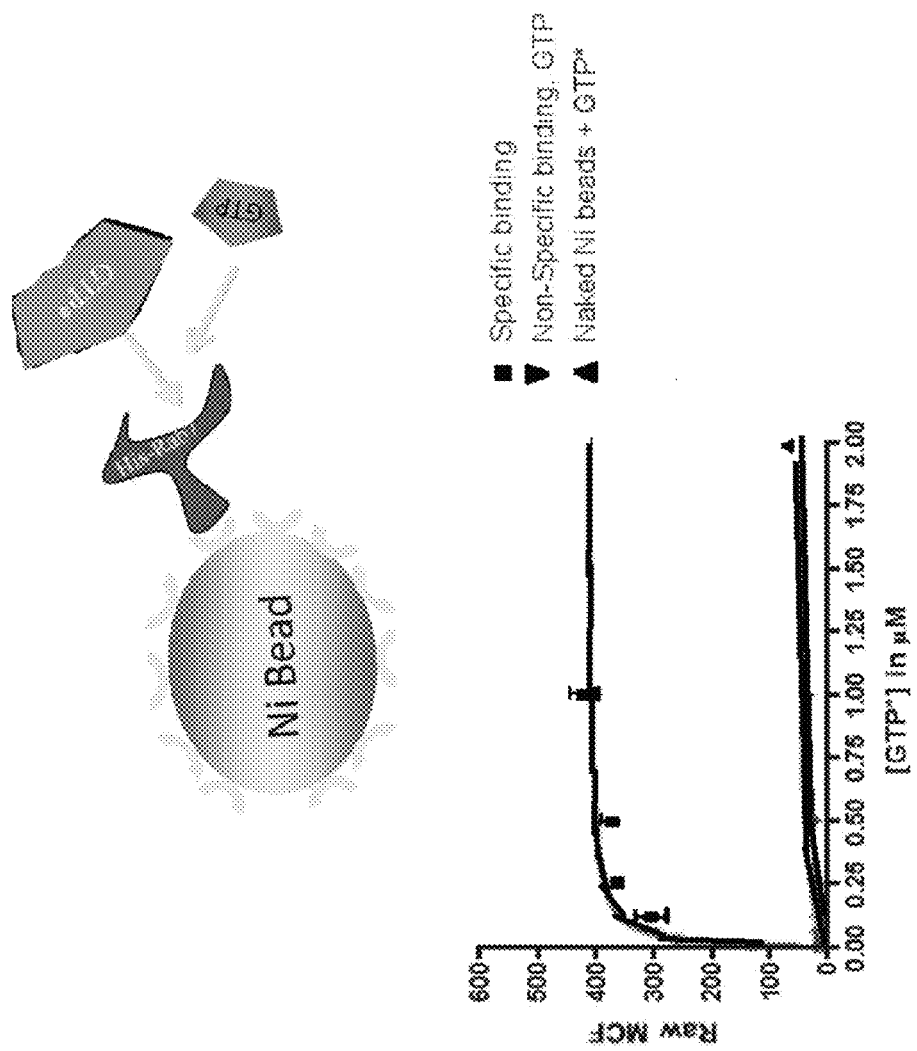
Figure 17C:
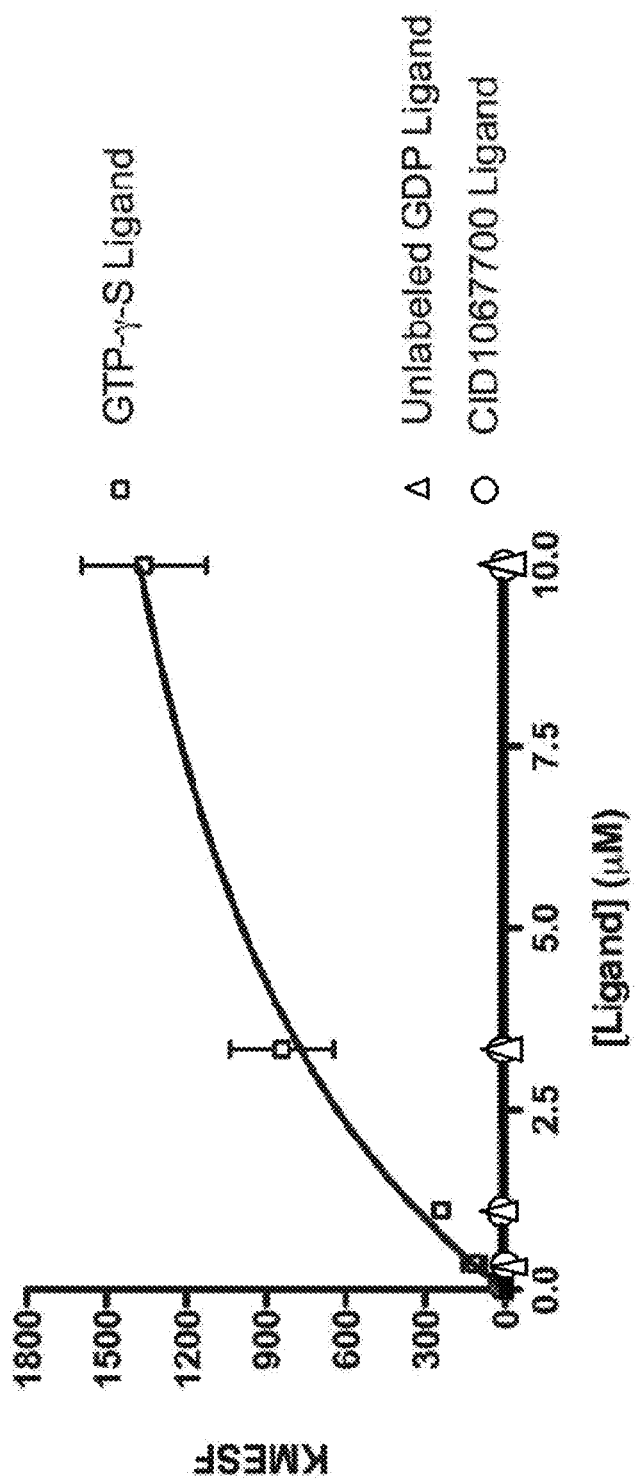
Figure 17D:
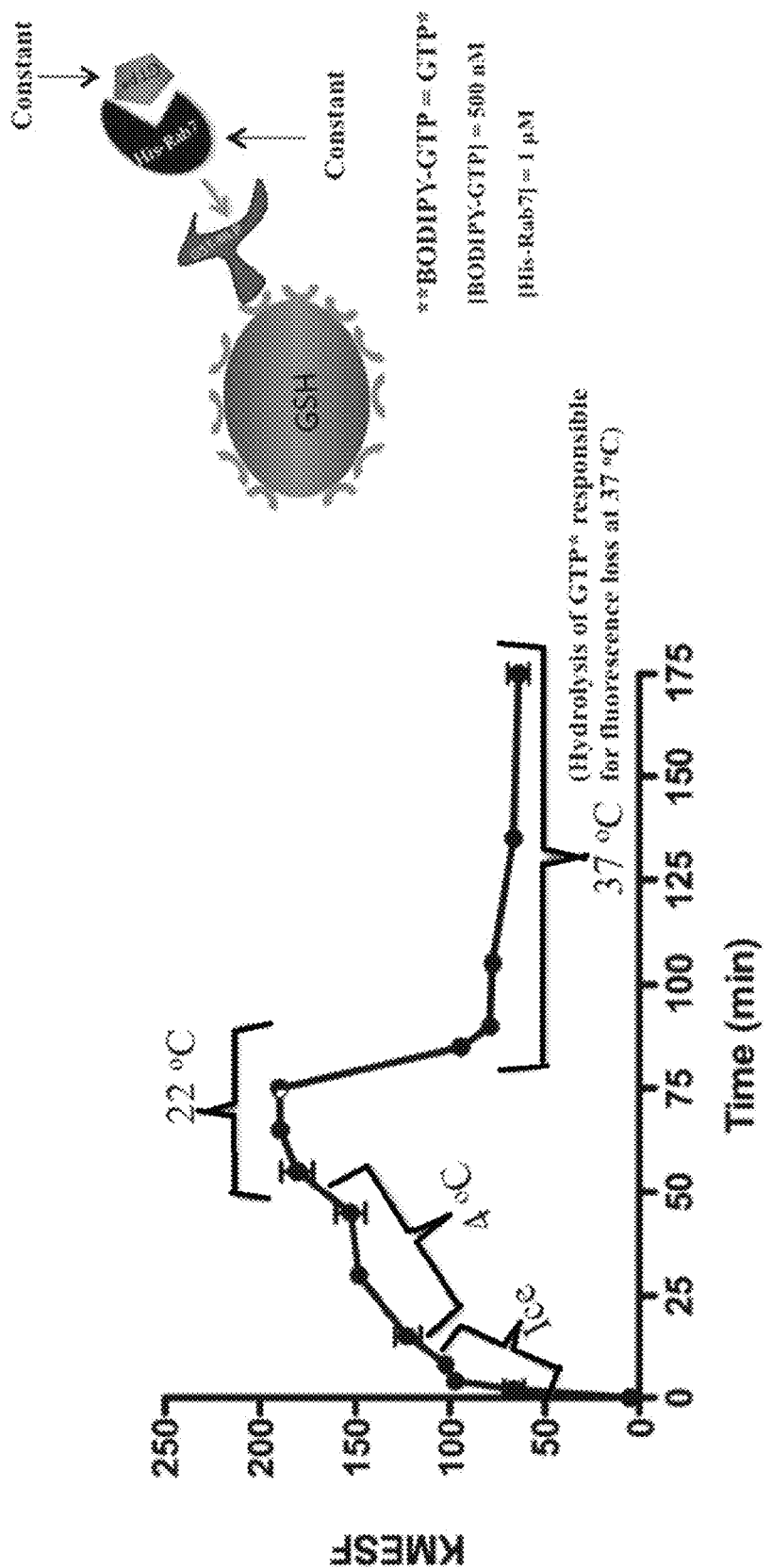

In other aspects, compounds of Formula (I) are used to elucidate protein function through protein-protein interaction assays, serve as lead compound for increasing target specificity through structure activity relationship determinations, and identifying protein contact sites critical for small molecule binding through crystallography (FIGS. 15-17). In still other aspects, compounds of Formula (I) serve as membrane-permeant small molecules that target all cells in a cell-based assay simultaneously and enable resulting consequences and phenotypes to be measured within about one hour or less (FIG. 18A-C).

The present invention relates to any one or more of the compounds disclosed above and/or pharmaceutical compositions that comprise an effective amount of one or more compounds described above, in combination with a pharmaceutically acceptable carrier, additive or excipient.

DETAILED DESCRIPTION OF THE INVENTION

The following terms, among others, are used to describe the present invention. It is to be understood that a term which is not specifically defined is to be given a meaning consistent with the use of that term within the context of the present invention as understood by those of ordinary skill set.

The term "compound", as used herein, unless otherwise indicated, refers to any specific chemical compound disclosed herein and includes tautomers, regioisomers, geometric isomers, and where applicable, optical isomers (e.g. enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds that have been modified to facilitate the administration and delivery of compounds to a site of activity.

The term "patient" or "subject" is used throughout the specification within the context of an animal, generally a mammal and preferably a human, to whom treatment, including prophylactic treatment (prophylaxis), with the compositions according to the present invention is provided. For treatment of those infections, conditions or disease states that are specific for a specific animal such as a human patient, the term patient refers to that specific animal.

"Rab7 GTPase associated disorders" include, but are not limited to, a neurologic disease including hereditary sensory neuropathies (or "hereditary sensory and autonomic neuropathies", "HSAN") such as Charcot-Marie-Tooth type 2B disease, or neurodegerative diseases such as Alzheimers disease and the symptoms associated therewith; cancer (e.g. cancer of the prostate, liver, or breast); lipid metabolism disorders (particularly Niemann-Pick type C), bleeding and pigmentation disorders (e.g. Griscelli syndrome), mental retardation associated with Downs syndrome, ciliopathies that cause kidney, pancreas, liver and retinal disorders (e.g. tuberous sclerosis, autosomal dominant polycystic disease, among others), choroideremia, and symptoms associated with microbial pathogen or viral infections.

"Hereditary sensory neuropathies" (or "hereditary sensory and autonomic neuropathies") include, but are not limited to, Type I HSAN, Type 2 HSAN (congenital sensory neuropathy), Type 3 HSAN (familial dysautonomia familial dysautonomia), Type 4 HSAN (congenital insensitivity to pain with anhidrosis (CIPA)), and Type 5 HSAN (congenital insensitivity to pain with partial anhidrosis).

The term "cancer" is used throughout the present invention to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers for example, include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas, among others, that may be treated by the methods of treatment of the invention.

Although all cancers may be treated with the methods of the invention, either alone or in combination with one or more anticancer agents or in combination with radiation therapy, in certain particular aspects of the present invention, the cancers potentially treatable include thyroid, ovarian, and diffuse peritoneal malignant mesothelioma where Rab7 is known to be upregulated. Other cancers may also benefit from Rab7 mediated activation of autophagy or inhibition of growth factor activation including pancreatic cancer, lung cancer, breast cancer, leukemia or prostate cancer, including metastatic prostate cancer, especially where radiation therapy is used to treat the prostate cancer. Thus, the present invention is generally applicable and may be used to treat any cancer in any tissue, regardless of etiology. (see Zhang review, supra).

The term "traditional anti-cancer agent" is used to describe a compound other than those of the present invention which may be combined with a GTPase inhibitor as otherwise described herein for the treatment of cancer. Exemplary anticancer agents which may be used in the present invention include, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d ]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl]-quinolone, vatalanib, AG-013736, AVE-0005, the acetate salt of [D-Ser(But)6, Azgly 10] (pyro-Glu-His-Trp-Ser-Tyr-D-Ser(But)-Leu-Arg-Pro-Azgly-NH$_2$ acetate $[C_{59}H_{84}N_{18}Oi_4-(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

"Lipid metabolism disorders" include, but are not limited to, Gaucher's disease, Tay-Sachs disease, Niemann-Pick type C disease, Fabry's disease, fatty acid oxidation disorders, obesity-related metabolic diseases such as hyperlipidemia, insulin resistance, and coronary artery disease, and metabolic syndrome.

"Bleeding and pigmentation disorders" include, but are not limited to, pigmentation disorders such as involving hypopigmentation, depigmentation, or hyperpigmentation such as Griscelli syndrome, as well as bleeding disorders such as disseminated intravascular coagulation (DIC), hemophilia, Henoch-Schönlein purpura, Hereditary hemorrhagic telangiectasia (Rendu-Osler-Weber disease), thrombocytopenia, thrombophilia, and von Willebrand's disease.

"Bone disorders" including osteoporosis and osteopetrosis.

"Kidney diseases" include, but are not limited to, a glomerular disease, glomerulonephritis, nephrotic syndrome, as well as tuberous sclerosis and ciliopathies, as described by Li et al., Protein Cell 2011 2:13-25.

"Choroideremia" is a rare inherited disorder that causes progressive loss of vision due to degeneration of the choroid and retina. It occurs almost exclusively in males. Choroideremia is caused by the deletion of the Rab escort protein 1 (REP1), which all Rab proteins depend on for membrane delivery following synthesis. Therefore, increased activation of a particular Rab protein could enable function by bypassing REP 1 requirement.

"Symptoms associated with microbial pathogen or viral infections" include, but are not limited to, symptoms associated with disorders associated with infections by pathogenic bacteria (e.g. plague, *Helicobacter pylori, Coxiella burnetti, Salmonella, Chlamydia, mycobacterium tuberculosis* and anthrax), protozoa (e.g. malaria, sleeping sickness and toxoplasmosis), fungi (e.g. ringworm, candidiasis or histoplasmosis), and pathogenic viruses (e g influenza, yellow fever or AIDS). (see Zhang reference Table 3 for specifics re pathogens targeting Rab7)

The term "effective" is used herein, unless otherwise indicated, to describe an amount of a compound or composition which, in context, is used to produce or effect an intended result, whether that result relates to the inhibition of the effects of Rab7 GTPase, activation of the effects of the Rab7 GTPases, to potentiate the effects of a supplementary treatment used in treating a Rab7 GTPase-associated disorder (e.g. an anticancer agent or radiation therapy in cancer or as otherwise described herein). This term subsumes all other effective amount or effective concentration terms (including the term "therapeutically effective") that are otherwise described in the present application.

The terms "treat", "treating", and "treatment", etc., as used herein, refer to any action providing a benefit to a patient at risk for or afflicted by a Rab7 GTPase-associated disorder, including lessening or suppression of at least one symptom of a Rab7 GTPase associated disorder (whether through activation or inhibition of the GTPases), delay in progression of a Rab7 GTPase associated disorder or the reduction in likelihood of the onset of a Rab7 GTPase associated disorder. Treatment, as used herein, encompasses both prophylactic and therapeutic treatment.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "co-administration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time.

The terms "antagonist" and "inhibitor" are used interchangeably to refer to an agent, especially including chemical agents that are specifically disclosed herein that decreases or suppresses a biological activity, such as to repress an activity of Rab7 GTPase. An agonist of Rab7-activation may be important for modulation of some of the diseases described above. "Modulators of Rab7 GTPase activity" either repress or enhance an activity of Rab7.

The term "acyl" is art-recognized and refers to a group represented by the general formula hydrocarbylC(O)—, preferably alkylC(O)—.

The term "acylamino" is art-recognized and refers to a moiety having an amino group and an acyl group and may include substitutents on same as otherwise disclosed herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed herein, except where stability of the moiety is prohibitive. For example, substitution of alkenyl groups by one or more alkyl, carbocyclyl, aryl, heterocyclyl, or heteroaryl groups is contemplated.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$-substituent, where m is 0 to 6 and the substituent is an aryl or substituted aryl group, a cycloalkyl group, a cycloalkenyl, a heterocycle or a polycycle (two or three ringed), each of which may be optionally substituted.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 10 or fewer carbon atoms in its backbone (e.g., $C_1$-$C_{10}$ for straight chains, $C_1$-$C_{10}$ for branched chains), and more preferably 8 or fewer, and most preferably 6 or fewer. Likewise, preferred cycloalkyls have from 3-10 carbon atoms in their ring structure, and more preferably have 5, 6, 7 or 8 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety or as otherwise described herein. It will be understood by those skilled in the art that the individual substituent chemical moieties can themselves be substituted. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary, non-limiting substituted alkyls are described herein. Cycloalkyls can be further substituted with alkyls, alkenyls, alkynyls, alkoxys, alkylthios, aminoalkyls, carbonyl-substituted alkyls, —$CF_3$, —CN, and the like.

Analogous substitutions can be made to alkenyl and alkynyl groups to produce, for example, without limitation, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to eight carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$-substituent, wherein m is 0 or an integer from 1 to 8 and substituent is the same as defined herein and as otherwise below (R9 and R10 for amine/amino). Representative alkylthio groups include methylthio, ethylthio, and the like.

The terms "amine" and "amino" are art-recognized and refer to both unsubstituted and substituted amines, e.g., a moiety that can be represented, without limitation, by the general formula:

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally, $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group. Each of the groups which is bonded to the amine group, where applicable, may be optionally substituted.

The term "amido" is art-recognized as an amino-substituted carbonyl and includes a moiety that can be represented by the general formula:

wherein $R_9$, $R_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring or aromatic groups containing from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl groups". The aromatic ring can be substituted at one or more ring positions with such substituents as otherwise described herein, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

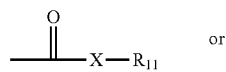 or

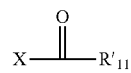

wherein X is a bond or represents an oxygen or a sulfur, and $R_{11}$ represents, for example without limitation, a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as otherwise described herein without limitation. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron withdrawing group" refers to chemical groups that withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups.

The term "ester", as used herein, refers to a group —C(O)O-substituent wherein the substituent represents, for example, a hydrocarbyl or other substitutent as is otherwise described herein.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, without limitation, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above without limitation, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like, and as otherwise described herein.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include up to 20-membered polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures (which can be cyclic, bicyclic or a fused ring system), preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "5- to 20-membered heterocyclic group" or "5- to 14-membered heterocyclic group" as used throughout the present specification refers to an aromatic or non-aromatic cyclic group having 5 to 20 atoms, preferably 5 to 14 atoms forming the cyclic ring(s) and including at least one hetero atom such as nitrogen, sulfur or oxygen among the atoms forming the cyclic ring, which is a "5 to 20-membered, preferably 5- to 14-membered aromatic heterocyclic group" (also, "heteroaryl" or "heteroaromatic") in the former case and a "5 to 20-membered", preferably a "5- to 14-membered non-aromatic heterocyclic group" in the latter case. Among the heterocyclic groups which may be mentioned include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 20-membered heterocyclic groups, preferably 3 to 14-membered heterocyclic groups and all subsets of heterocyclic groups (including non-heteroaromatic or heteroaromatic) subsumed under the definition of heterocyclic group are 3 to 20-membered heterocyclic groups, preferably 3 to 14-membered heterocyclic groups.

The term "8 to 20-membered heterocyclic group", or "8 to 14-membered heterocyclic group" refers to an aromatic or non-aromatic fused bicyclic or tricyclic group having 8 to 20, preferably 8 to 14 atoms forming the cyclic rings (two or three rings) and include at least one hetero atom such as nitrogen, sulfur or oxygen among the atoms forming the cyclic rings, which is a "8 to 20-membered", preferably a "8- to 14-membered aromatic heterocyclic group" (also, "heteroaryl" or "heteroaromatic") in the former case and a "8 to 20-membered", preferably a "8- to 14-membered non-aromatic heterocyclic group" in the latter case. "8 to 20-membered heterocyclic groups" and "8 to 14 membered heterocyclic groups" are represented by fused bicyclic, tricyclic and tetracyclic ring structures containing nitrogen atoms such as indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "5- to 14-membered non-aromatic heterocyclic group" as used throughout the present specification refers to a non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimideandsuccinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "8- to 14-membered non-aromatic heterocyclic group" as used throughout the present specification refers to a non-aromatic fused cyclic ring system (generally with two or three rings) having 8 to 14 atoms forming the cyclic rings (bicyclic or tricyclic) and including at least one hetero atom such as nitrogen, sulfur or oxygen among the atoms forming the cyclic rings.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 14-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl, among others.

The term "6- to 14-membered aromatic heterocyclic group" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine*. "8 to 14-membered aromatic heterocyclic groups" refer to those substituents or radicals having 8 to 14 atoms forming fused two or three cyclic ring systems. Specific examples include indole, quinoline, isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among numerous others.

The term "6- to 14-membered heterocyclic group" as used throughout the present specification refers to those substituents defined by "5- to 14-membered heterocyclic group" which have 6 to 14 atoms forming the cyclic ring(s). As specific examples there may be mentioned piperidinyl, piperazinyl, N-methylpiperazinyl, morpholinyl, tetrahydropyranyl, 1,4-dioxane and phthalimide.

The term "3 to 7-membered heterocyclic group" as used throughout the present specification refers to those heterocyclic substituents that have 3 to 7 atoms forming the cyclic ring, preferably 5 to 6 atoms forming the cyclic ring.

The term "8 to 14-membered heterocyclic group" as used throughout the present specification refers to those substituents defined "8- to 14-membered heterocyclic groups that have 8 to 14 atoms forming the fused cyclic ring system.

The term "heterocyclylalkyl", as used herein, refers to an alkyl group substituted with a heterocycle group.

The term "hydrocarbyl", as used herein, refers to an optionally substituted group that is bonded through a carbon atom and typically has at least one carbon-hydrogen bond and a primarily carbon backbone, but may optionally include heteroatoms. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with, without limitation, such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The phrase "protecting group" as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic, non-aromatic and inorganic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents (groups) as otherwise described herein, for example, a halogen, a hydroxyl, a carbonyl (such as a carboxyl, an alkoxycarbonyl, a formyl, or an acyl), an ether, a thioether, a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on a moiety or chemical group can themselves be substituted.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. It is acknowledged that the term "unsubstituted" simply refers to a hydrogen substituent or no substituent within the context of the use of the term.

Preferred substituents for use in the present invention include, for example, within context, hydroxyl, carboxyl, cyano (C≡N), nitro (NO$_2$), halogen (preferably, 1, 2 or 3 halogens, especially on an alkyl, especially a methyl group such as a trifluoromethyl), thiol, alkyl group (preferably, $C_1$-$C_6$, more preferably, $C_1$-$C_3$), alkoxy group (preferably, $C_1$-$C_6$ alkyl or aryl, including phenyl), ether (preferably, $C_1$-$C_6$ alkyl or aryl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl) (preferably, $C_1$-$C_6$ alkyl or aryl), thioester (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). More preferably, the term "substituted" shall mean within its context of use alkyl, alkoxy, halogen, hydroxyl, carboxylic acid, nitro and amine (including mono- or di-alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms.

The term "sulfamoyl" is art-recognized and includes a moiety represented by the general formula:

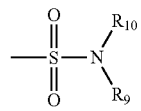

where $R_9$ and $R_{10}$ are substituents as described above.

The term "sulfate" is art-recognized and includes a moiety represented by the general formula:

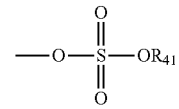

Where $R_{41}$ is an electron pair, hydrogen, alkyl, cycloalkyl or aryl.

The term "sulfonamido" is art-recognized and includes a moiety represented by the general formula:

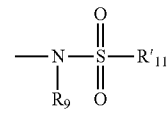

Where $R_9$ and $R'_{11}$ are as described above.

The term "sulfonate" is art-recognized and includes a moiety represented by the general formula:

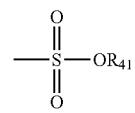

Where $R_{41}$ is an electron pair, hydrogen, alkyl, cycloalkyl or aryl.

The term "sulfoxido" or "sulfinyl" is art-recognized and includes a moiety represented by the general formula:

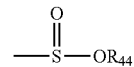

where $R_{44}$ is selected from the group consisting of hydrogen, alkyl, alkenyl, alkynyl, cycloalkyl, heterocyclyl, aralkyl or aryl., which groups may be optionally substituted.

The term "thioester" is art-recognized and is used to describe a group —C(O)SR⁹ or —SC(O)R⁹ wherein R⁹ represents an optionally substituted hydrocarbyl group as otherwise described herein.

As used herein, the definition of each expression of alkyl, m, n, etc. when it occurs more than once in any structure, is intended to reflect the independence of the definition of the same expression in the structure.

Figure 24:
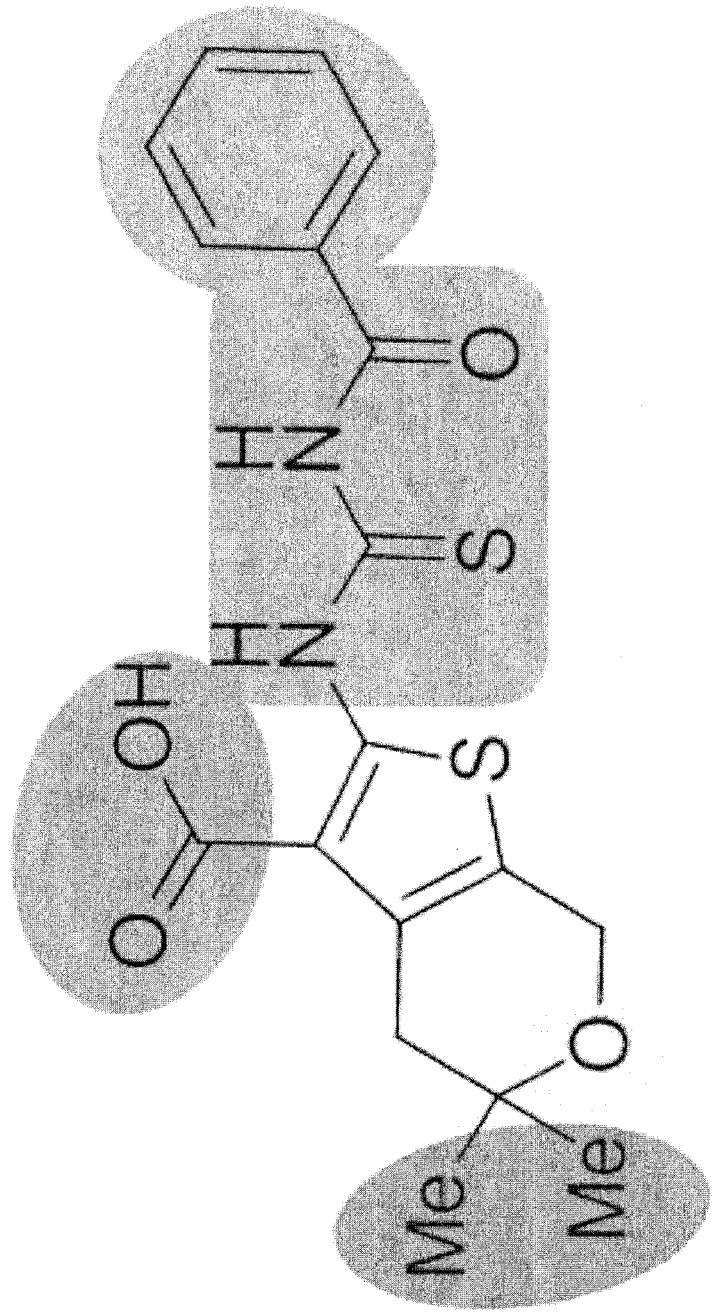
FIG. 24: Shows compound structure, ML282 or CID1067700, and shaded regions of SAR optimization.
Figure 34:
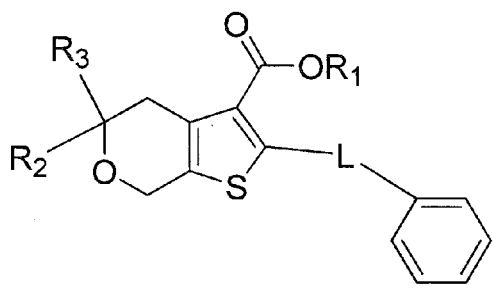
FIG. 34: Structure activity relationship of representative and preferred compounds according to the present invention which is directed to inhibition of Rab7 wt protein nucleotide binding.

By way of example, certain preferred aromatic and aliphatic rings and their derivatives and substituents which may be used as pharmacophores or substituents in compounds according to the present invention include, but are not limited to, phenyl, benzyl, pyridine, cyclohexadiene, dihydropyridine, tetrahydropyridine, piperidine, pyrazine, tetrahydropyrazine, dihydro-pyrazine, piperazine, pyrimidine, dihydropyrimidine tetrahydro-pyrimidine, hexahydro-pyrimidine, pyrimidinone, triazine, dihydro-triazine, tetrahydro-triazine, triazinane, tetrazine, dihydro-tetrazine, tetrahydro-tetrazine, tetrazinane, pyrrol, dihydro-pyrrole, pyrrolidine, imidazolidine, dihydro-imidazolidine, imidazole, dihydro-imidazole, azetidine, triazole, dihydro-triazole, triazolidine, tetrazole, dihydro-tetrazole, tetrazolidine, diazepane, tetrahydro-diazepine, dihydro-diazepine, diazepine, oxazole, dihydrooxazole, oxazolidine, isoxazole, dihydroisoxazole, isoxazolidine, thiazole, dihydrothiazole, thiazolidine, isothiazole, dihydroisothiazole, isothiazolidine, oxadiazole, dihydrooxadiazole, oxadiazolidine, thiadiazole, dihydro-thidiazole, thidiazolidine, oxazinane, dihydro-oxazinane, dihydro-oxazine, oxazine (including morpholine), thiazinane, dihydrothiazinane, dihydro-thiazine, thiazine (including thiomorpholine), thiazine, furan, dihydrofuran, tetrahydrofuran, thiophene, pyridazine-3,6-dione, tetrahydrothiophene, dihydrothiophene, tetrahydrothiophene, dithiolane, dithiole, dithiolone, dioxolane, dioxole, oxathiole, oxathiolane, pyridinone, dioxane, dioxanedione, benzoquinone, dihydro-dioxine, dioxine, pyran, 3,4-dihydro-2H-pyran, pyranone, 2H-pyran-2,3(4H)-dione, oxathiane, dihydro-oxathiine, oxathiine, oxetane, thietane, thiazeto, cyclohexadienone, lactam, lactone, piperazinone, pyrroledione, cyclopentenone, oxazete, oxazinanone, dioxolane, 3,4-dihydro-2H-thiopyran 1,1-dioxide, dioxolanone, oxazolidinone, oxazolone, thiane 1-oxide, thiazinane 1-oxide, tetrahydro-thiopyran, thiane 1,1-dioxide, dioxazinane, pyrazolone, 1,3-thiazete, thiazinane 1,1-dioxide, 6,7-dihydro-5H-1,4-dioxepine, 1,2-dihydropyridazin-3(4H)-one, pyridine-2,6(1H,3H)-dione, sugar (glucose, mannose, galactose, fucose, fructose, ribose) and derivatives from the compounds, with reference to FIG. 24 and those which are set forth in attached FIG. 34.

Bicyclic and fused rings include, for example, naphthyl, quinone, quinolinone, dihydroquinoline, tetrahydroquinoline, naphthyridine, quinazoline, dihydroquinazoline, tetrahydroquinazoline, quinoxaline, dihydroquinazoline, tetrahydroquinazoline, pyrazine, quinazoline-2,4(1H,3H)-dione, isoindoline-1,3-dione, octahydro-pyrrolo-pyridine, indoline, isoindoline, hexahydro-indolone, tetrahydropyrrolo oxazolone, hexahydro-2H-pyrrolo[3,4-d]isoxazole, tetrahydro-1,6-naphthyridine, 2,3,4,5,6,7-hexahydro-1H-pyrrolo[3,4-c]pyridine, 1H-benzo[d]imidazole, octahydropyrrolo[3,4-c]pyrrole, 3-azabicyclo[3.1.0]hexane, 7-azabicyclo[2.2.1]hept-2-ene, diazabicyclo-heptane, benzoxazole, indole, 1,4-diazabicyclo[3.3.1]nonane, azabicyclo-octane, naphthalene-1,4-dione, indene, dihydroindene, 2,3,3a,7a-tetrahydro-1H-isoindole, 2,3,3a,4,7,7a-hexahydro-1H-isoindole, 1,3-dihydroisobenzofuran, 1-methyl-3a,4,5,6,7,7a-hexahydro-1H-indole, 3-azabicyclo[4.2.0]octane, 5,6-dihydrobenzo[b]thiophene, 5,6-dihydro-4H-thieno[2,3-b]thiopyran, 3,4-dihydropyrazin-2(1H)-one, 2H-benzo[b][1,4]thiazine, naphthyridin-4(1H)-one, octahydropyrrolo[1,2-a]pyrazine, imidazo-pyridazine, tetrahydroimidazo-pyridazine, tetrahydropyridazine, thiazinone, 5-thia-1-azabicyclo[4.2.0]oct-2-en-8-one, 4-thia-1-azabicyclo[3.2.0]heptan-7-one, 1,6,7,8-tetrahydroimidazo[4,5-d][1,3]diazepine, 8H-thiazolo[4,3-c][1,4]oxazin-4-ium, 8H-thiazolo[4,3-c][1,4]thiazin-4-ium, pteridine, thiazolo[3,4-a]pyrazin-4-ium, 7-(methylimino)-7H-pyrrolo[1,2-c]thiazol-4-ium, thiazolo-pyrazine, 3,7-dioxabicyclo[4.1.0]hept-4-ene, 6,7-dihydro-5H-pyrrolo[1,2-a]imidazole, 3,3a-dihydrofuro[3,2-b]furan-2(6aH)-one, tetrahydro-3aH-[1,3]dioxolo[4,5-c]pyrrole, 7-ethylidene-7H-pyrrolo[1,2-c]thiazol-4-ium, hexahydro-1H-pyrrolo[2,1-c][1,4]oxazine, 6,7,8,8a-tetrahydro-1H-pyrrolo[2,1-c][1,4]oxazine, 2-azabicyclo[2.2.2]oct-2-ene, 6,6a-dihydrothieno[3,2-b]furan-5(3aH)-one, 4,5-dihydropyridin-3(2H)-one, 4,7a-dihydro-3aH-[1,3]dioxolo[4,5-c]pyran, 6,7-dihydro-1H-furo[3,4-c]pyran-1,3(4H)-dione, 3,3a,4,7a-tetrahydro-2H-furo[2,3-b]pyran, 2,4a,7,7a-tetrahydro-1H-cyclopenta[c]pyridine, 4H-pyrano[3,2-b]pyridine-4,8(5H)-dione, 1,2,3,3a,4,7a-hexahydropyrano[4,3-b]pyrrole, 2,3,8,8a-tetrahydroindolizin-7(1H)-one, octahydro-1H-pyrido[1,2-a]pyrazin-1-one, 2,6,7,8,9,9a-hexahydro-1H-pyrido[1,2-a]pyrazin-1-one, 6,7,8,8a-tetrahydropyrrolo[1,2-a]pyrazin-1(2H)-one, hexahydropyrrolo[1,2-a]pyrazin-1(2H)-one, bicyclo[2.2.1]hepta-2,5-diene.

Spiro moieties: 1,5-dioxaspiro[5.5]undecane, 1,4-dioxaspiro[4.5]decane, 1,4-diazabicyclo[3.2.1]octane, 5-azaspiro[2.5]octane, 5-azaspiro[2.4]heptane, 3,9-diaza-6-azoniaspiro[5.5]undecane, 3,4-dihydrospiro[benzo[b][1,4]oxazine-2,1'-cyclohexane], 7-oxa-4-azaspiro[2.5]oct-5-ene.

Pharmaceutical compositions comprising combinations of an effective amount of at least one Rab7 GTPase-inhibiting or -activating compound according to the present invention, and one or more of the compounds otherwise described herein, all in effective amounts, in combination with a pharmaceutically effective amount of a carrier, additive or excipient, represents a further aspect of the present invention.

The compositions used in methods of treatment of the present invention, and pharmaceutical compositions of the invention, may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in methods of treatment of the present invention, and pharmaceutical compositions of the invention, may be administered orally, parenterally, by inhalation spray, topically, rectally, nasally, buccally, vaginally or via an implanted reservoir. The term "parenteral" as used herein includes subcutaneous, intravenous, intramuscular, ultra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions used in methods of treatment of the present invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject suffering from or at risk of developing a Rab7 GTPase associated disorder can be treated by administering to the patient (subject) an effective amount of a compound of Formula (I) according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating Rab7 GTPase-associated disorders or ameliorate the secondary effects and conditions associated with Rab7 GTPase-associated disorders. This treatment can also be administered in conjunction with other conventional therapies, such as radiation treatment or surgery in the case of cancer.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent, as are topically administered compositions.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The compounds used according to the present invention may be prepared using techniques which are well-known in the art. Chemical synthetic approaches are well known as exemplified, e.g. in Oganisyan, et al., "Condensed Thienopyrimidines. 19. Study of the Heterocyclization of 2-Hydrazino-6,6-dimethyl-5,6-dihydro-8H-pyranothieno[2,3-d]pyrimidin-4-one", *Chemistry of Heterocyclic Compounds*, Vol. 40, No. 1 (January 2004), pp. 79-83, and PCT WO2009009550, each of which is incorporated by reference in its entirety herein. The approach uses standard functional group chemistry according to well known reaction schemes and examples, or modifications thereof, using readily available starting materials, reagents and conventional synthesis procedures. In these reactions, it is also possible to make use of variants that are themselves known to those of ordinary skill in this art, but are not mentioned in greater detail. Furthermore, other methods for preparing compounds used in methods of the invention will be readily apparent to the person of ordinary skill in the art in light of the known reaction schemes in the art.

EXAMPLES

The invention may be better understood by reference to the following non-limiting examples that are provided as exemplary of the invention. The following examples are presented in order to more fully illustrate the preferred embodiments of the invention and should in no way be construed, however, as limiting the broad scope of the invention.

Experimental Overview

Multiplex, flow cytometry bead-based assays were used to identify or characterize inhibitors or activators of Rab7 GTPases. Glutathione-S-transferase (GST)-tagged Rab7 GTPase was bound to glutathione beads, labeled with a red fluorescence intensity. Beads were mixed dispensed into 384-well plates with test compounds, and fluorescent-guanosine triphosphate (GTP) binding was used as the readout. This novel multiplex assay allowed the authors to screen a library of almost 200,000 compounds and identify positive compounds, which were further verified by dose-response analyses, using 6- to 8-plex assays. After the elimination of false-positive and false-negative compounds, PubChem No. CID1067700 was identified and characterized. CID1067700 was shown to be a general inhibitor of small molecular weight GTPases. It is the first small molecule to prevent guanine nucleotide binding and to inhibit a Rab subfamily member. As detailed in this invention, CID1067700 inhibits the Rab7 GTPase in a dose-dependent manner with high potency and efficacy and is active in biochemical and cell-based secondary assays.

Example 1

PubChem No. CID1067700 Inhibits Guanine Nucleotide binding by Rab7 GTPase

Figure 3:
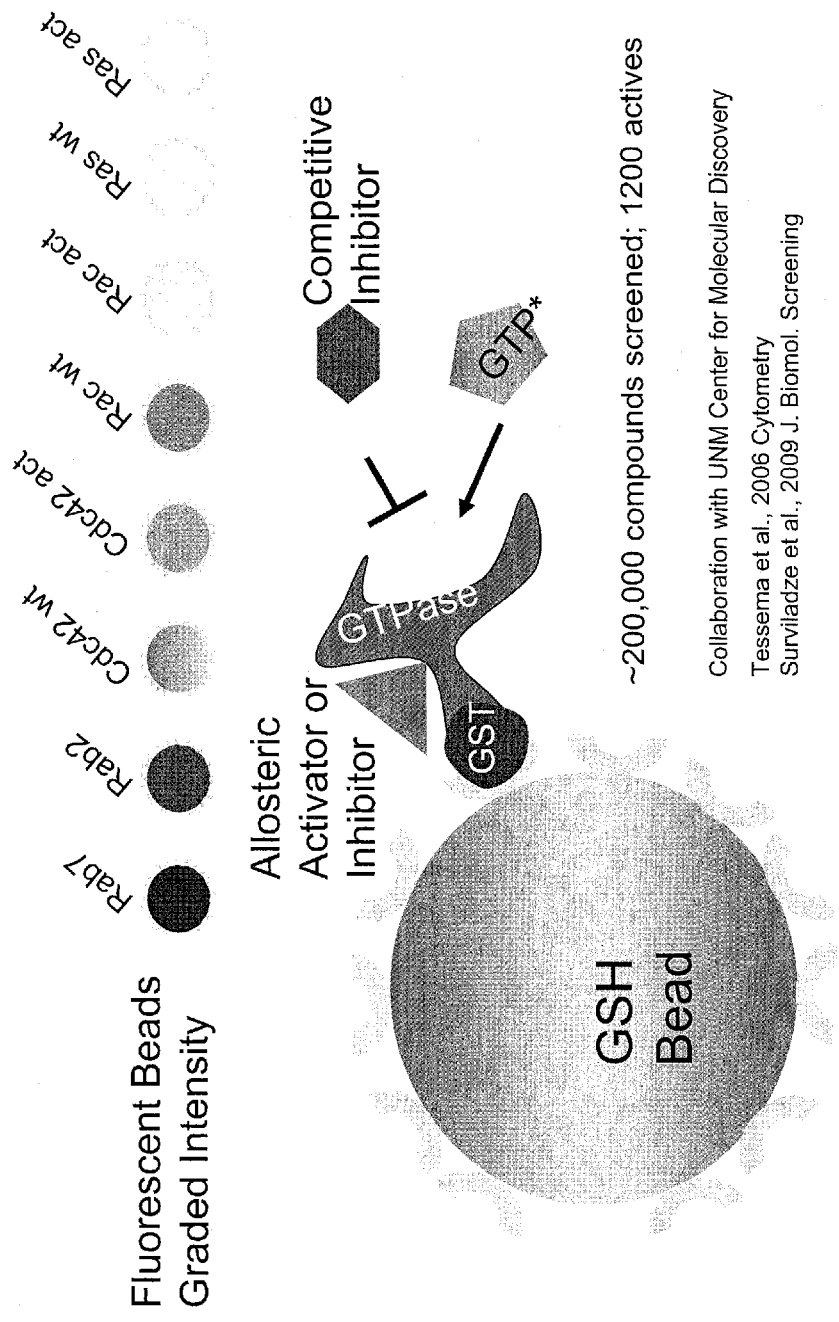
FIG. 3: Illustrates HTS used to identify GTPase activators and inhibitors.
Figure 4:
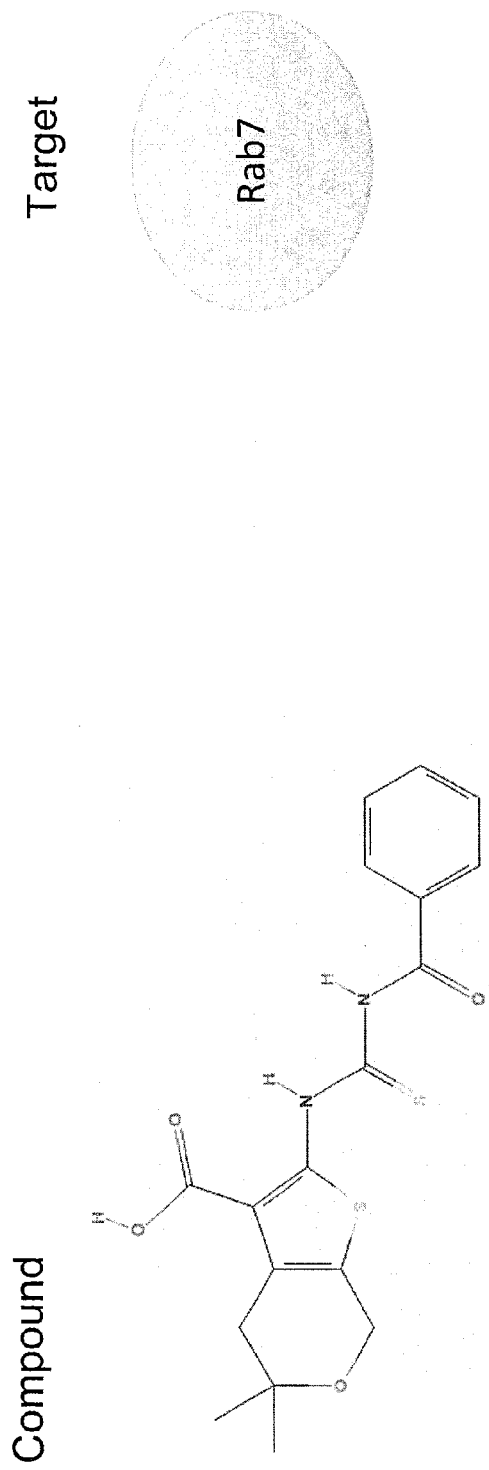
FIG. 4: Shows the chemical structure of PubChem #: CID1067700 or MLS000673908 (see also FIG. 24).

As depicted in FIG. 3, over 300,000 unique chemical compounds in the NIH Roadmap small molecule library were screened for Rab7 GTPase-inhibition using an in vitro BODIPY-GTP binding assay in accordance with the protocols described herein. Active small molecules were identified by scoring for a greater than 20% increase or decrease in fluorescent GTP-binding relative to untreated controls. PubChem No. CID1067700 (aka ML282 and MLS000673908) (2-(benzoylcarbamothioylamino)-5,5-dimethyl-4,7-dihydrothieno[2,3-c]pyran-3-carboxylic acid) (FIGS. 4, 24) was determined to be the most active inhibitor of Rab7 GTPase. Subsequent chemical synthesis and structure activity analyses identified several additional compounds with high efficacy and potency (FIGS. 24, 25, 33a-e, 34).
High Throughput Flow Cytometry Protocol
Bead sets were coated with individual GST-small G proteins, blocked with Buffer (0.01% NP-40; 30 mM HEPES pH 7.5; 100 mM KCl; 20 mM NaCl; 1 mM EDTA; 0.1% BSA and 1 mM DTT), incubated overnight at 4° C., and finally washed in buffer. The different bead sets, acquired from Duke Scientific, had similar size (~4 microm diameter) however they were distinguished by varied magnitude of emission at 665+/−10 nm with excitation at 635 nm.

The assay was conducted in 384-well microplates in a total well volume of 10.1 microliters (5 microliters of bead mixture, 0.1 microliters of test compound, and 5 microliters of 200 nM Bodipy-FL-GTP in buffer containing BSA and DTT for a final concentration of BODIPY-GTP of 100 nM). Positive Controls, which contain bead mixture and BODIPY-GTP but no test compound, are located in columns 1 and 2 on plate. Negative Controls containing bead mixture with BODIPY-GTP and 0.5 mM unlabeled GTP, were collected from a separate test tube. Plates were placed on rotators and incubated for 40-45 minutes at 4 degrees C.

Test compounds were cherry-picked from compound storage plates at 10 mM in neat DMSO, then serially diluted 1:3 eight times for a total of nine different test compound concentrations in DMSO. Final compound dilutions in DMSO ranged from 1 microM to 10 mM. These dilutions were then diluted 1 to 100 to give an assay concentration range of 10 nM to 100 µM.

Beads were coated with proteins as described in the primary screening procedure. Dose response experiments reported here include one multiplex format for Rab7 wt and GST-GFP.

Sample acquisition and preliminary analysis was conducted with the HyperCyt® high throughput flow cytometry platform. The HyperCyt system interfaces a flow cytometer and autosampler for high-throughput microliter volume sampling from 384-well microtiter plates [Kuckuck, et al., 2001; Ramirez, et al., 2003]. The stream of particles is excited at 488 nm and 635 nm, and flow cytometric data of light scatter and fluorescence emission at 530+/−20 nm (FL1) and emission at 665+/−10 nm (FL8) are collected on a Cyan Flow Cytometer (Dako). Analysis of the time-resolved acquisition data file uses IDLE Query software to merge the flow cytometry data files with compound worklist files generated by HyperSip software. The raw data were parsed in IDLe Query software to produce annotated fluorescence summary data for each well. The parsed data were then processed through an Excel template file constructed specifically for the assay to segregate data for each target and the fluorescence scavenger in the multiplex. Gating based on forward scatter (FS) and side scatter (SS) parameters was used to identify singlet bead populations. Gating based on FL8 emission distinguishes the beads coated with different proteins, and the green median fluorescence intensity (MFI) per bead population (well) was calculated.
Calculations In dose response experiments, the assay was performed without compound (DMSO control) and with nine different concentrations of compound, from 10 nM to 100 µM, to produce a series of 9 data points. IDLe Query software calculates the median channel fluorescence (MCF) for each of these ligand concentrations, generating competition curves.

Ligand competition curves were fitted by Prism® software (GraphPad Software, Inc., San Diego, Calif.) using nonlinear least-squares regression in a sigmoidal dose response model with variable slope, also known as the four parameter logistic equation. Curve fit statistics were used to determine the following parameters of the model: EC50, microM—concentration of added test compound competitor that inhibited fluorescent ligand binding by 50 percent; LOGEC50—the logarithm of EC50; TOP—the response value at the top plateau; BOTTOM—the response value at the bottom plateau; HILLSLOPE—the slope factor, or the Hill coefficient; STD_LOGEC50, STD_TOP, STD_BOTTOM, STD_HILLSLOPE—standard errors of LOGEC50, TOP, BOTTOM, and HILLSLOPE; EC50_95CI_LOW, EC50_95CI_HIGH—the low and high boundaries of the 95% confidence interval of the EC50 estimate, RSQR—the correlation coefficient (r squared) indicative of goodness-of-fit.

In order to be considered active and get a score >0, the compounds have to pass the following criteria:

8<LOGEC50<−4 (the computed EC50 value should be in the interval of tested concentrations)

0.5<|HILLSLOPE|<2 (the absolute value of HILLSLOPE should be higher than 0.5 and lower than 2)

[TOP−STD_TOP]>[BOTTOM+STD_BOTTOM] (the amplitude of the biological signal should be statistically significant)

|LOGEC50|>STD_LOGEC50 (the standard error of LOGEC50 should be lower than the absolute value of LOGEC50)

|HILLSLOPE|>STD_HILL SLOPE (idem for the HILLSLOPE)

[TOP−BOTTOM] scavenger<0.5*[TOP−BOTTOM] target (the inherent fluorescence of the test compound should be lower than 50% of the biological signal)

[TOP−BOTTOM]/TOP for GST-GFP<0.5*[TOP−BOTTOM]/TOP for the target (the interference of the compound with the GST/GSH interaction should be lower than 50% of the biological signal).

The PUBCHEM_ACTIVITY_SCORE was based on the following equation;

PUBCHEM_ACTIVITY_SCORE=1000*(−4−LOG $EC50$)/4*[(TOP−STD_TOP)−(BOTTOM+STD_BOTTOM)]/TOP*(1−||HILLSLOPE|−1|)*(1−STD_LOG$EC50$/|LOGEC50|).

In this assay active compounds have the activity score higher or equal than 1, and for inactive compounds the activity score is 0.

Example 2

CID1067700 Affects Rab7 Function In Vitro and In Vivo

In the experiments of this example, it was determined: (1) that CID1067700 modulates Rab7 wild-type, Rab7T22N and Rab7Q67L guanine nucleotide interaction in vitro and Rab7 wild-type membrane association in cell based assays; and (2) that Rab7WT protein-protein interactions can be assayed in vitro enabling testing of CID1067700 modulation of specific protein-protein interactions.

Assessment of Binding and Kinetics of Binding and Disassociation (FIGS. 8-13, 30-31) Protocol Rab7WT (4 microM) was bound to glutathione beads overnight at 4° C. Rab7WT on GSH-beads was depleted of nucleotide by incubating with 10 mM EDTA containing buffer for 20 min at 30° C., washing twice with 0.01% NP-40 containing HPS buffer, then re-suspending in the same buffer containing 1 milliM EDTA, 1 milliM DTT and 0.1% BSA. Kinetic assays were performed by incubating 50 microliter of GST-Rab7WT-GSH-bead suspension for 2 min with either DMSO, or 10 µM CID1067700 and subsequently adding 50 µl of various concentration ice cold BODIPY-GTP. Association of the fluorescent nucleotide was measured using a FacSCAN flow cytometer in the kinetic mode. Data were converted to ASCII format using IDLE Query software.

Measured values of bead-bound BODIPY-GTP after 3 minutes of binding were converted to molecular equivalent soluble fluoresceine (MESF) with the aid of calibration beads (Bangs Lab) by the following equation;

$$kMESF = Slope*MCF + Intercept$$

where MCF is the Median Channel Fluorescence measurement of bead-bound BODIPY-GTP, kMESF are kiloMESF (1000*MESF), and Slope and Intercept are the from the linear regression fit of the 5 different levels of calibration beads.

The resulting values of kMESF were graphed versus the different concentrations of BODIPY-GTP in GraphPad Prism and fitted by non-linear regression to one site binding pre the following equation;

$$kMESF = Bmax*ConcBODIPY\text{-}GTP/(Kd + ConcBODIPY\text{-}GTP)$$

where ConcBODIPY-GTP is the concentration of BODIPY-GTP, Bmax is the maximum binding of BODIPY-GTP per bead and Kd is the equilibrium binding constant of BODIPY-GTP to protein on bead.

Figure 8:
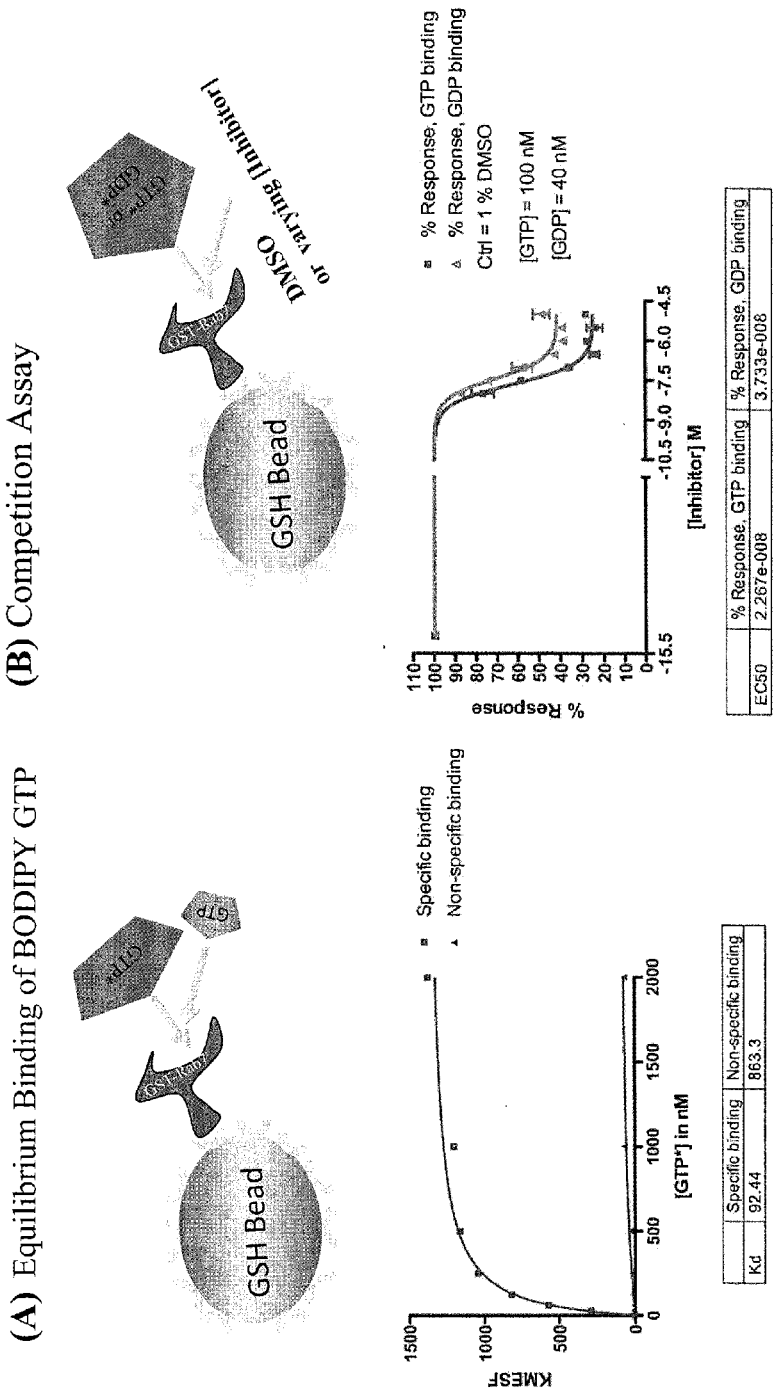
FIG. 8: Shows the results of an equilibrium binding study that determined that CID1067700 or MLS000673908 binds to the Rab7 GTPase nucleotide binding pocket.
Figure 10:
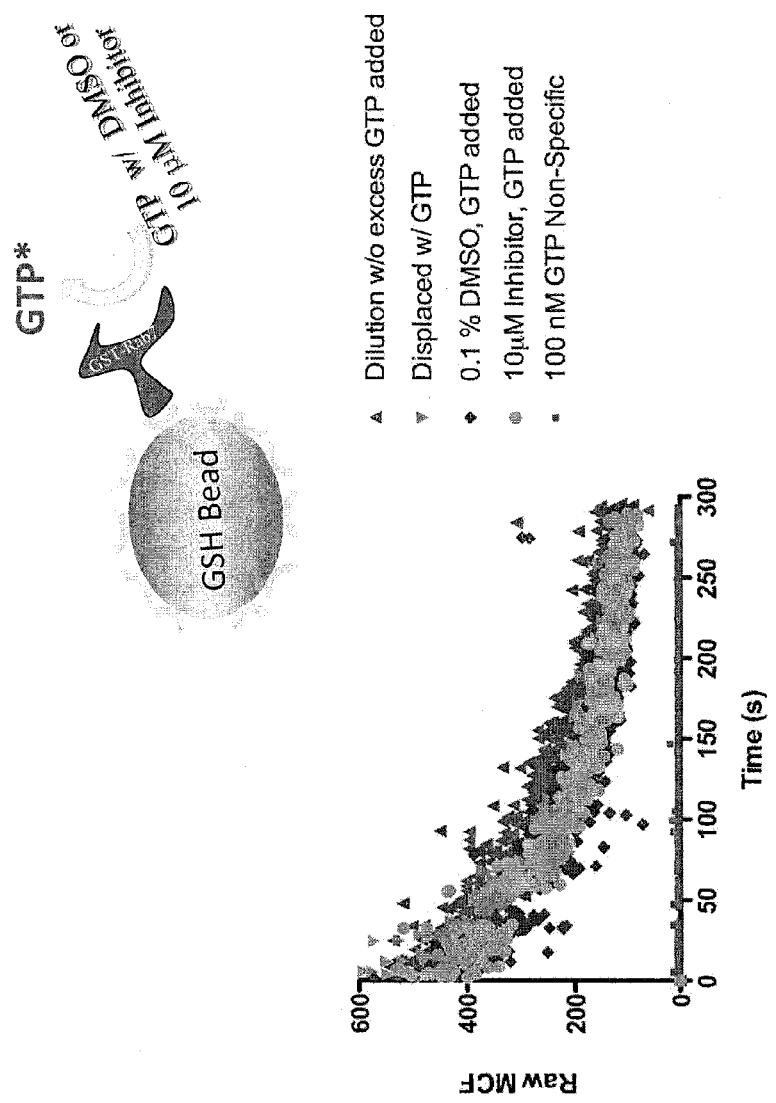
Figure 11:
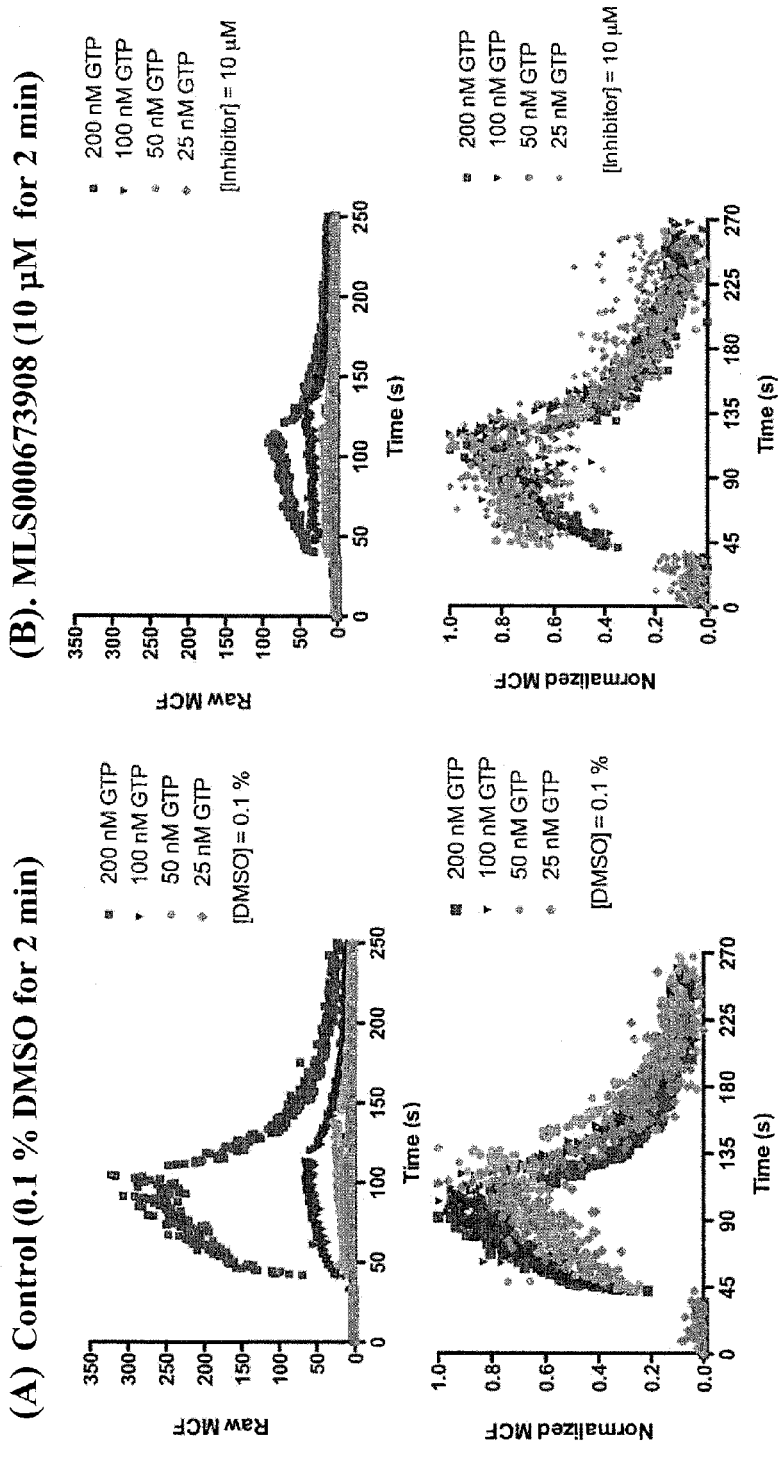

Based on the equilibrium binding results shown in FIG. 8 (left panel) and the competition curve results shown FIG. 8 (right panel), as well as FIG. 29 it was concluded that CID1067700 bound to the nucleotide binding pocket of Rab7 GTPase.

Referring to FIGS. 9-13, binding and disassociation experiments were conducted in which increasing amounts of DMSO or another inhibitor were added in accordance with a dilution protocol as described above and mean channel fluorescence (MCF) values were determined. Based on the results shown in FIGS. 9-13, it was concluded that CID1067700 is a competitive inhibitor of the nucleotide binding site of Rab7 GTPase.

Virtual Docking Studies

Virtual docking studies were conducted and it was determined that CID1067700 docked to the Rab7 nucleotide binding pocket in both the GDP and GTP conformations (FIGS. 14, 32).

Figure 19:
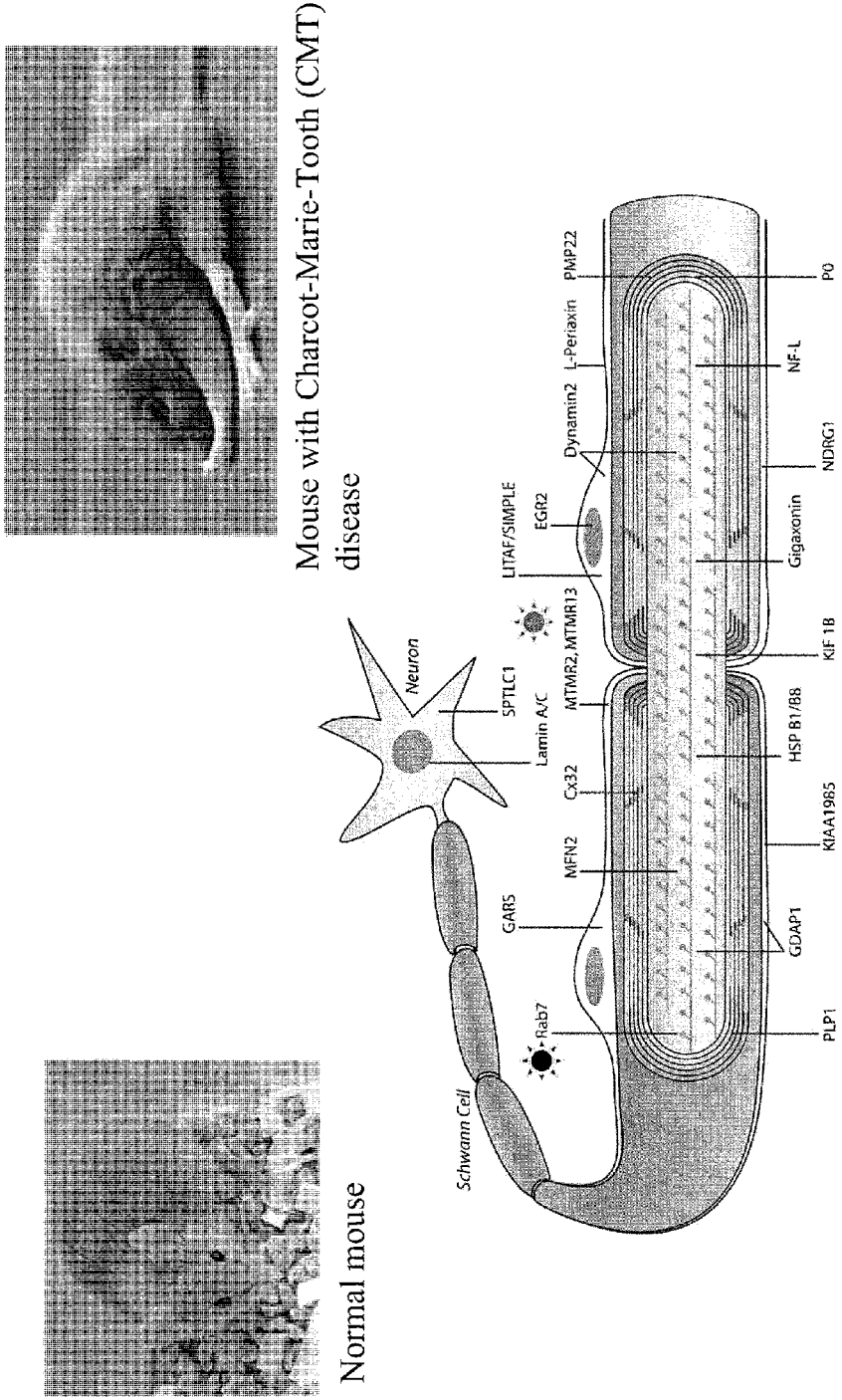
FIG. 19: Illustrates a schematic overview of proteins mutated in CMT disease: Schwann cells and neurons, including Rab7 and potential interacting protein MTMR13.

CID1067700 as a Potential Modulator of Rab7WT Protein-Protein Interaction In Vitro The putative functions and malfunctions of proteins encoded by genes mutated in Charcot-Marie-Tooth disease (CMT) in normal and affected peripheral nerves may be investigated. Some proteins implicated in demyelinating CMT, peripheral myelin protein 22, protein zero (P0), and connexin32 (Cx32/GJB1) are crucial components of myelin. Periaxin is involved in connecting myelin to the surrounding basal lamina. Early growth response 2 (EGR2) and Sox10 are transcriptional regulators of myelin genes. Mutations in proteins associated with endosomes and lysosomes are central players in CMT (FIGS. 19-20). The late endosomal GTPase Rab7 controls phospholipid synthesis and signaling, while the lipid phosphatases myotubularin-related protein 2 (MTMR2), and MTMR13/set-binding factor 2 are involved lipid dephosphorylation and signal termination. Together these proteins regulate membrane trafficking that is critical for myelin homeostasis and nerve growth factor mediated signaling and receptor degradation. Pathomechanisms related to alterations of endocytic processes are a widespread phenomenon in demyelinating neuropathies because of their essential nature in myelin homeostasis. Due to the close interaction between myelinating Schwann cells and neurons, related disease mechanisms are also involved in axonal neuropathies although there is considerably more functional heterogeneity. Some mutations, most notably in P0, GJB1, ganglioside-induced differentiation-associated protein 1 (GDAP1), neurofilament light chain (NF-L), and dynamin 2 (DNM2), can result in demyelinating or axonal neuropathies introducing additional complexity in the pathogenesis. Often, this relates to the intimate connection between Schwann cells and neurons/axons leading to axonal damage even if the mutation-caused defect is Schwann-cell-autonomous. See FIG. 19. This mechanism is likely for P0 and Cx32 mutations and provides the basis for the unifying hypothesis that also demyelinating neuropathies develop into functional axonopathies. In GDAP1 and DNM2 mutants, both Schwann cells and axons/neurons might be directly affected. NF-L mutants have a primary neuronal defect but also cause demyelination.

As shown in FIG. 15-16, Rab7 function in endocytosis depends on protein-protein interactions. FIG. 16 illustrates how CID1067700 could be used to test and modulate Rab7WT protein-protein in vivo.

Results of an in vitro binding study using Rab7-GFP and GST-DENN fusion proteins pre-coupled to GSH beads (FIG. 17 panel A) confirmed that Rab7 interacts with MTMR13 via a DENN domain. As shown in FIG. 17 (panel B), another in vitro binding assay using His-tagged Rab7 immobilized on Ni beads and GTP confirmed GTP binding by His-Rab7. RILP is an effector of Rab7 and only binds to the GTP-conformer (FIG. 17 panel C-D). Inlcusion of the inhibitor blocked RILP binding (FIG. 17 panel C). Thus, the combination of these assays can be used to discern nucleotide binding and hydrolysis, as well as protein-protein interactions. The assays can also measure if a small molecule binds the guanine nucleotide binding pocket, interferes with protein-protein interaction or causes the protein to adopt the GTP- or GDP-bound conformations.

Example 3

CID1067700 Alters Rab7 Activity in Cells

Results of an immunofluorescence study indicate that CID1067700 increased membrane localization of Rab7 in a HeLa cell line. See FIG. 18A. Measurement of growth factor receptor (EGFR) degradation in response to growth factor stimulation, showed CID1067700 inhibited lysosomal degradation, in human keratinocytes (SCC-12F) and cervical carcinoma cells overexpressing Rab7 (HeLa-Rab7 wt), a process that depends on Rab7 activity (FIG. 18B-C). These data confirm that small molecule is capable of crossing the cell membrane and altering Rab7 activity in situ. It also illustrates that small molecules can modulate activation status through binding to the guanine nucleotide binding pocket. Thus, depending on the fit in the pocket, the molecule could give rise to a protein that is constitutively active or inactive. Such compounds have utility for treatment of human diseases including genetic and acquired diseases where Rab7 is defective or hyperactivated (lipid storage disorders, bone metabolic diseases, cancers, neuropathies, among others) and infectious diseases.

Example 4

Rab7 Mutants (K157N, L129F, N161T and V162M) Associated with CMT2B Disease Interact with the Nucleotides Differently Relative to Rab7WT FIG. 20 illustrates Rab7 CMT disease associated mutants K157N, L129F, N161T and V162M. FIG. 21 and FIG. 22 show the results of GDP and GTP binding studies which established that Rab7 mutants (K157N, L129F, N161T and V162M) associated with CMT2B disease interact with the nucleotides differently relative to Rab7WT. These data support the idea that small molecules could be generated through rationale design to differentially interfere with nucleotide binding by wild-type and mutant Rab7 proteins.

Example 5

CID1067700 Acts as a Pan Inhibitor of Small Molecular Weight GTPases

Figure 26:
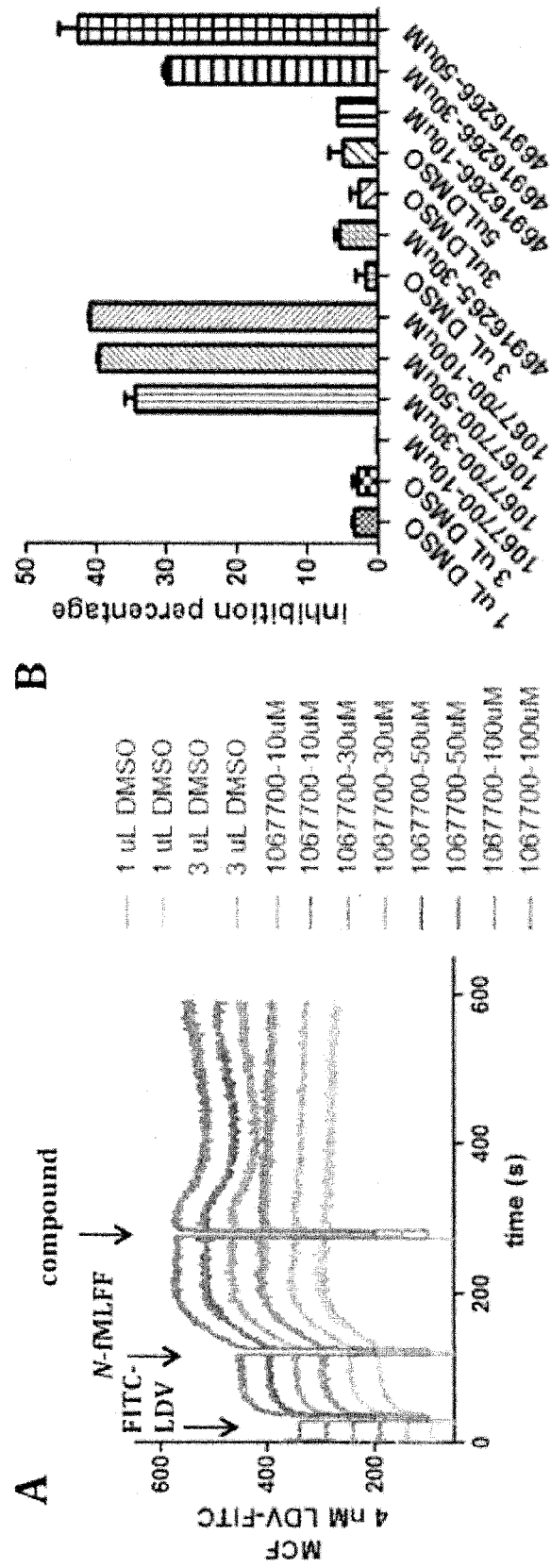
FIG. 26: Shows that ML282 (CID1067700) inhibits VLA4 binding with LDV peptide. A. FITC-LDV binds resting state of VLA4, then N-fMLFF addition leads to high-affinity state binding which is inhibited by ML282 (CID1067700). Note, time line of fluorescence readings are graphed in a staggered manner for ease of viewing (25 MCF has arbitrary been added for each run) B. Inhibition percentage for ML282 (CID1067700), CID46916265 and CID46916266. The inhibition percentage was calculated according to Equation 1.
Figure 27:
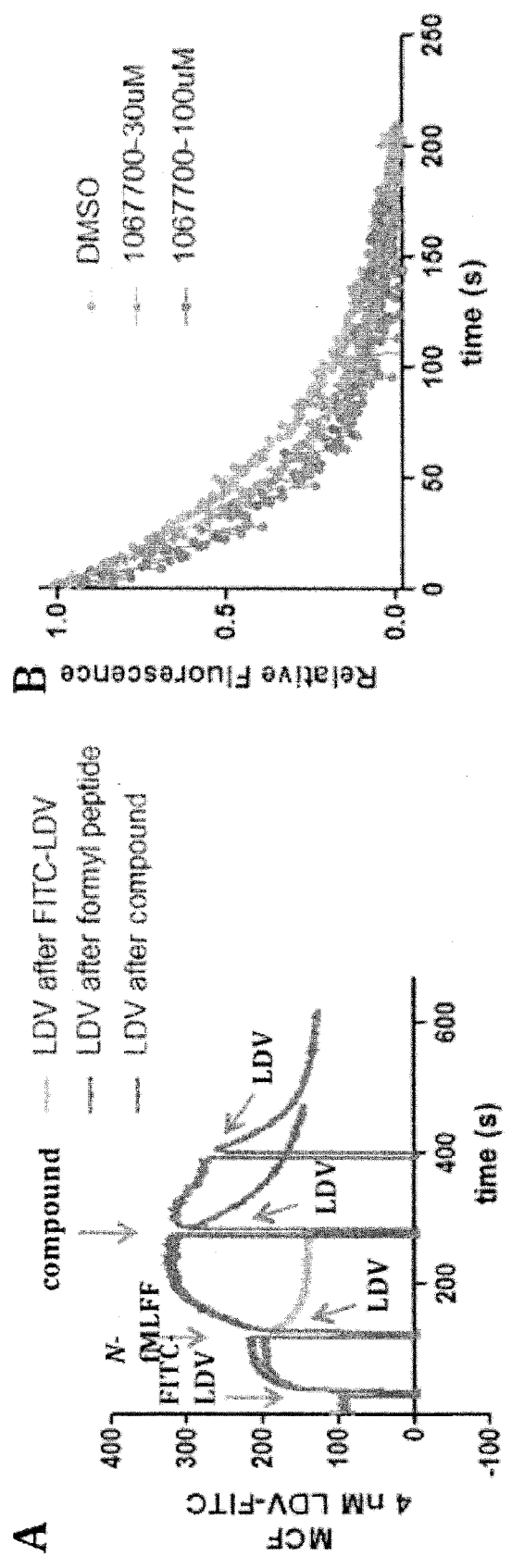
FIG. 27: Shows the binding affinity between FITC-LDV and its receptor, VLA4, was estimated by dissociation rate constant. A. Non-fluorescent LDV was added to the cell suspension after FITC-LDV, N-fMLFF or compounds. B. After compounds or DMSO treatment, LDV was added at the fluorescence minimum. The following fluorescence was regraphed as a ratio compared to that at the time of the addition.

FIG. 29 illustrates in vitro inhibition of Cdc42, Ras and other Rab family members by CID1067700 albeit at lower efficacy than what is observed for Rab7. FIGS. 26-28 show inhibition of cellular signaling downstream of integrin receptors considered to signal to Rho family GTPases. Since CID1067700 is the first example of a class of guanine nucleotide binding inhibitors, rationale drug design could be used to guide the development of inhibitors with greater activity against other small GTPase subfamily members such as Arf, Ras, Rho and Ran. Precedent is provided by tyrosine kinase inhibitors that act on the conserved ATP binding pocket but demonstrate specificity against select kinases.

Methods
Reagents

Reagents used in this study were obtained from Sigma unless otherwise indicated. Sephadex G-25, glutathione (GSH) Sepharose 4B, and Superdex peptide beads (13 µm with an exclusion limit of 7 kDa) were from Amersham Biosciences. BODIPY (4,4-difluoro-4-bora-3a,4a-diaza-s-indacene or dipyrromethene boron difluoride) nucleotide analogues (BODIPY FL GTP 2'-(or 3')-O—[N-(2-aminoethyl)urethane] G-35778 and BODIPY FL GDP 2'-(or -3')-O—[N-(2-aminoethyl)urethane], G-22360) were from Invitrogen Molecular Probes (Carlsbad, Calif., USA). Concentrations of BODIPY nucleotides were based on absorbance measurements and an extinction coefficient value of 80,000 $M^{-1}$ $cm^{-1}$. 2-(benzoylcarbamothioylamino)-5,5-dimethyl-4,7-dihydrothieno[2,3-c]pyran-3-carboxylic acid with compound identification number (CID) 1067700 was from ChemDiv.

Expression and Purification of GST-Rab7

GST-Rab7 protein was expressed in *E. coli* BL21(DE3). Cultures were grown at 37° C. to a bacterial density of 0.5-0.7 absorbance units at 595 nm and protein induced by transfer to room temperature and addition of 0.2 mM isopropyl-beta-D-1-thiogalactopyranoside (IPTG) for 16-18 h to maximize yield of properly folded active fusion protein. Purification of GST-Rab7 was performed according to standard procedures and as previously described (34).

Synthesis of Glutathione Beads for Flow Cytometry Assay

High GSH density beads used for flow cytometry were synthesized by loading Superdex peptide beads with GSH as previously reported (34, 35).

Immobilization of Rab7 on GSH Beads for Flow Cytometry

All nucleotide binding to Rab7 and measurements were performed in the HPS buffer (30 mM Hepes, pH 7.5, 20 mM NaCl and 100 mM KCl) containing 1 mM EDTA. A BectonDickinson FACScan flow cytometer with a 488-nm excitation laser and standard detection optics was used for all assays (33). Pure GST-Rab7 protein was incubated in 96-well plates at 4° C. overnight with $10^5$ GSH beads in a total volume of 100 µl of HPS buffer containing 1 mM EDTA and 1 mM dithiothreitol (DTT) added fresh. Unbound protein was removed by centrifugation twice at 800 g and resuspension in fresh buffer.

Dose Response or Competition Binding Assays

Dose response assays were conducted in two different modes. In the first case, $2 \times 10^3$ GSH beads loaded with GST-Rab7 were incubated with a fixed concentration of nucleotide (GDP or GTP) for 1 h in the presence of 1% DMSO (final) or increasing concentrations of CID1067700 ($10^{-3}$-100 µM) in 1% DMSO and a total volume of 20 µl on a 96-well plate. A stock solution of CID1067700 (10 mM) was prepared in 100% DMSO and stored in single use aliquots at −80° C. In the second mode, $2 \times 10^3$ GSH beads loaded with GST-Rab7 protein were incubated for 2 h 15 min at 4° C. with varying concentrations of fluorescent guanine nucleotide (0-2 µM) in a total volume of 20 µl on a 96-well plate in the presence of either 1% DMSO or a fixed CID1067700 concentration (0.1-1 µM). For measurements on the flow cytometer, samples were transferred to a tube suitable (BD Bioscience) for flow cytometry and were diluted at least 10-fold in HPS buffer. This dilution step was necessary to ensure discrimination of bead-associated fluorescence and background fluorescence of soluble proteins and also ensured sufficient sample volume for the measurement.

Nucleotide Dissociation Assays

Nucleotide dissociation under equilibrium conditions was accomplished by first loading GST-Rab7 with fixed concentrations of BODIPY-GTP (100 nM) or BODIPY-GDP (40 nM) for 2 hr 15 min at 4° C. followed by initiating release of bound nucleotide with either unlabeled GDP (10 µM) or CID1067700 (10 µM). As a negative control, GST-Rab7 was preloaded with unlabelled GDP (1 mM) for 2 hr 15 min at 4° C. prior to adding BODIPY-GTP or BODIPY-GDP at the above concentrations for a further 2 hr 15 min and then similarly initiating release of bound BODIPY-linked nucleotide with unlabeled GDP (10 μM) to obtain fluorescence for non-specific binding under equilibrium binding conditions. This low level bead associated fluorescence was subtracted from specific binding to obtain accurate measurement of the off rates. Data normalization was performed by subtracting dilution only values from competitor treated experimental values.

Molecular Docking of CID1067700 on Rab7

Docking calculations were performed using OpenEye Fred (Fred, version 2.2.5, OpenEye Scientific Software, Inc., Santa Fe, N. Mex., USA, www.eyesopen.com, 2010) docking software. Rab7 crystal structures (PDB code: 1T91 GDP-conformer, 1VG8 GNP-conformer) were used to dock CID1067700 on Rab7 for the wild type. Chemgauss3 scoring function was used to evaluate ligand binging potential. Docking simulations provide only a qualitative assessment of binding probability of our ligand to Rab7 and should be examined with care, however the results indicate that CID1067700 can potentially bind to Rab7 nucleotide binding site and no steric constrains were observed.

Data Analyses

All data processing and analyses employed GraphPad Prism software (GraphPad Software). For kinetic experiments, raw data acquired were first processed using IDLE query software (obtained from University of New Mexico Center for Molecular Discovery, UNM CMD) before further analysis using GraphPad Prism. All experiments are representative of at least three independent trials.

Synthesis of Derivatives for Structure Activity Analyses

General experimental and analytical details: $^1$H and $^{13}$C NMR spectra were recorded on a Bruker AM 400 spectrometer (operating at 400 and 101 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H,3H-tetrafluoropropoxy) phosphazine; and a make-up solvent of 90:10:0.1 MeOH:Water:Formic Acid which was introduced to the LC flow prior to the source to assist ionization. Melting points were determined on a Stanford Research Systems OptiMelt apparatus.

Synthesized analogs were prepared by the general route depicted in FIG. 8. Stepwise procedures for all synthesized analogs and intermediates are described. Analytical characterization is provided for all tested commercial and synthetic compounds itemized in this manuscript.

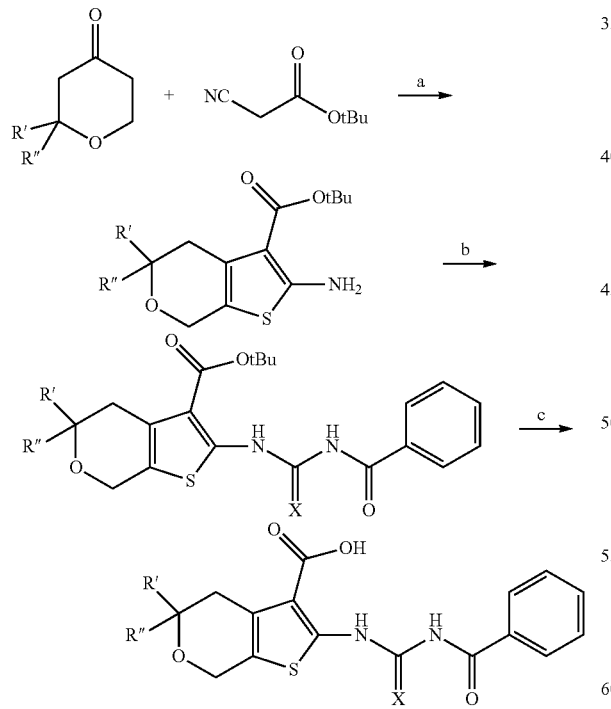

General scheme for synthetic analogs

R' = H or Me
R" = H or Me
X = S or O
Reagents: a) Morpholine, sulfur, EtOH, 50° C.;
b) PhCONCO, THF, 50° C.;
c) TFA, DCM, rt.

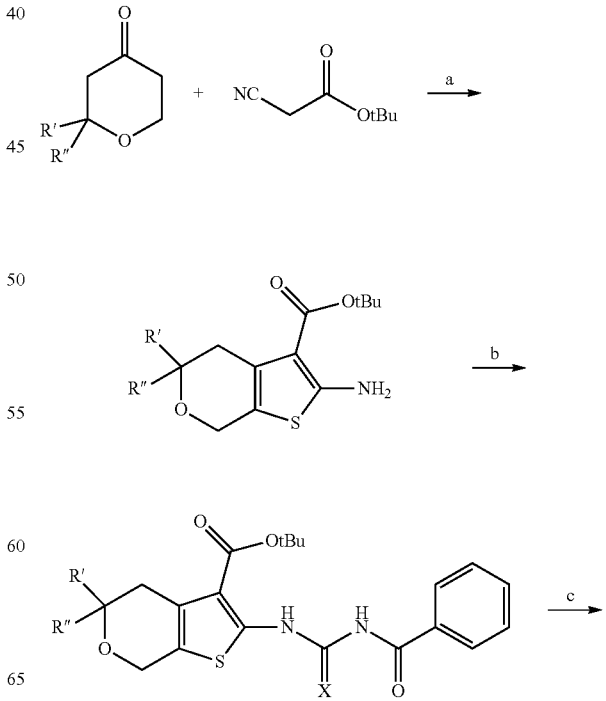

General scheme for synthetic analogs

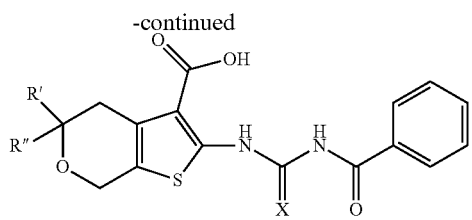

R′ = H or Me
R″ = H or Me
X = S or O
Reagents: a) Morpholine, sulfur, EtOH, 50° C.;
b) PhCONCO, THF, 50° C.;
c) TFA, DCM, rt.

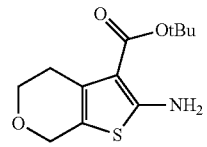

tert-Butyl 2-amino-5,7-dihydro-4H-thieno[2,3-c]pyran-3-carboxylate

Following a previously reported procedure[57] tetrahydro-4H-pyran-4-one (0.28 mL, 3.0 mmol, 1 equiv.), tert-butyl cyanoacetate (0.47 mL, 3.3 mmol, 1.1 equiv.), sulfur (0.106 g, 3.30 mmol, 1.1 equiv.), and morpholine (0.39 mL, 4.5 mmol, 1.5 equiv.) were dissolved in EtOH (9 mL) and stirred at 50° C. 1 for 16 h. The solvent was removed and water (7 mL) was added. The product was extracted with EtOAc (2×7 mL) and purified by preparatory HPLC (0-20% EtOAC:hexanes). The product was isolated as a clear, pale yellow oil (0.77 g, quantitative yield). $^1$H NMR (400 MHz, CDCl$_3$) δ 5.98 (s, 2H), 4.55 (t, J=2.0 Hz, 2H), 3.90 (t, J=5.6 Hz, 2H), 2.79 (ddd, J=7.6, 3.8, 2.0 Hz, 2H), 1.54 (s, 9H). $^{13}$C NMR (101 MHz, CDCl$_3$) δ 165.38, 161.65, 130.33, 114.60, 106.76, 80.37, 65.20, 64.66, 28.57, 27.94.

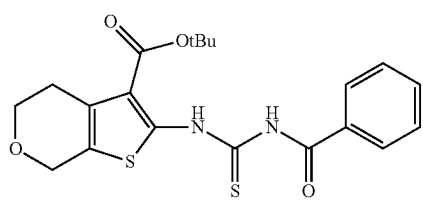 [SMILES: CC(C)(C)OC(=O)c1c(NC(=S)NC(=O)c2ccccc2)sc2c1CCOC2]

tert-Butyl 2-(3-benzoylthioureido)-5,7-dihydro-4H-thieno[2,3-c]pyran-3-carboxylate tert-Butyl 2-amino-5,7-dihydro-4H-thieno[2,3-c]pyran-3-carboxylate (0.099 g, 0.39 mmol, 1 equiv.) and PhCONCS (0.06 mL, 0.4 mmol, 1 equiv.) were dissolved in THF (2 mL) and stirred at 50° C. for 16 h. The solvent was removed and the product was purified by preparatory HPLC (0-30% EtOAC:hexanes). The product was isolated as a white solid (0.131 g, 80% yield). $^1$H NMR (400 MHz, CDCl$_3$) δ 14.75 (s, 1H), 9.21 (s, 1H), 7.92 (dd, J=5.2, 3.3 Hz, 2H), 7.64-7.57 (m, 1H), 7.54-7.46 (m, 2H), 4.71 (s, 2H), 3.94 (t, J=5.6 Hz, 2H), 2.90 (t, J=5.6 Hz, 2H), 1.63 (s, 9H). $^{13}$C NMR (101 MHz, CDCl$_3$) δ 173.72, 165.23, 164.54, 147.15, 133.48, 131.81, 129.36, 129.04, 127.77, 125.77, 117.76, 82.36, 65.20, 64.71, 28.51, 27.38.

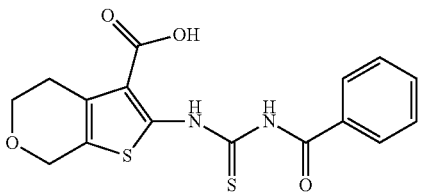

SID 99381129
CID 46916266

2-(3-benzoylthioureido)-5,7-dihydro-4H-thieno[2,3-c]pyran-3-carboxylic acid (SID 99381129, CID46916266)

To a solution of tert-Butyl 2-(3-benzoylthioureido)-5,7-dihydro-4H-thieno[2,3-c]pyran-3-carboxylate (0.104 g, 0.25 mmol, 1 equiv.) in DCM (10 mL) was added TFA (2 mL, 26 mmol, 100 equiv.), and the reaction was stirred at rt for 16 h. The solvent was removed and the product was triturated with 1:1 Et$_2$O/hexanes (25 mL) and filtered. The product was purified by mass-directed reverse-phase chromatography and isolated as a white solid (3 mg, 3% yield). $^1$H NMR (400 MHz, CDCl$_3$) δ 14.92 (br s, 1H), 9.02-9.09 (m, 1H), 7.83-7.91 (m, 1H), 7.55-7.66 (m, 2H), 7.41-7.50 (m, 2H), 7.19-7.23 (m, 1H), 4.69-4.76 (m, 2H), 3.92-3.98 (m, 2H), 2.88-3.03 (m, 2H). LCMS retention time: 2.955 min; LCMS purity at 215 nm=100%. HRMS m/z calculated for $C_{16}H_{15}N_2O_4S_2$ [M$^+$+1]: 363.0468. found 363.0464.

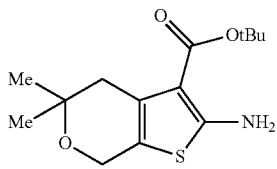

tert-Butyl 2-amino-5,5-dimethyl-5,7-dihydro-4H-thieno[2,3-c]pyran-3-carboxylate A mixture of 2,2-dimethyldihydro-2H-pyran-4(3H)-one (0.300 g, 2.34 mmol, 1 eq), tert-butyl cyanoacetate (0.37 mL, 2.57 mmol, 1.1 eq), sulfur (0.083 g, 2.57 mmol, 1.1 eq), morpholine (0.30 mL, 3.51 mmol, 1.5 eq), and ethanol (7 mL) was heated at 50° C. for 16 h. The reaction mixture was then filtered, and the filter cake washed with ethyl acetate (20 mL). Purification by silica gel chromatography (0-20% EtOAc:Hex ramp over 20 min) afforded the desired product tert-butyl 2-amino-5,5-dimethyl-5,7-dihydro-4H-thieno[2,3-c]pyran-3-carboxylate as a yellow solid (0.631 g, 2.23 mmol, 95% yield). $^1$H NMR (400 MHz, CDCl$_3$) δ 5.88 (s, 2H), 4.52 (t, J=1.9, 2H), 2.64 (t, J=1.9, 2H), 1.53 (s, 9H), 1.26 (s, 6H).

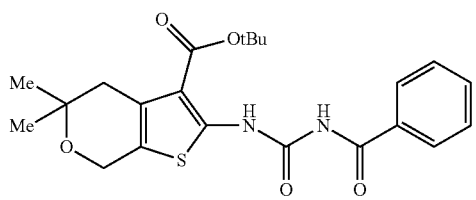 [SMILES: CC(C)(C)OC(=O)c1c(NC(=O)NC(=O)c2ccccc2)sc2c1CC(C)(C)OC2]

tert-Butyl 2-(3-benzoylureido)-5,5-dimethyl-5,7-dihydro-4H-thieno[2,3-c]pyran-3-carboxylate tert-Butyl 2-amino-5,5-dimethyl-5,7-dihydro-4H-thieno[2,3-c]pyran-3-carboxylate (0.116 g, 0.41 mmol, 1 equiv.) and PhCONCO (0.06 mL, 0.5 mmol, 1.2 equiv.) were dissolved in THF (2 mL) and stirred at 50° C. for 16 h. The solvent was removed and the product was purified by preparatory HPLC (0-40% EtOAC:hexanes). The product was isolated as a white solid (0.105 g, 59% yield). $^1$H NMR (400 MHz, CDCl$_3$) δ 13.26 (s, 1H), 9.81 (s, 1H), 8.13 (d, J=7.0 Hz, 2H), 7.65 (d, J=6.7 Hz, 3H), 4.72 (s, 2H), 2.75 (s, 2H), 1.64 (s, 9H), 1.32 (s, 6H).

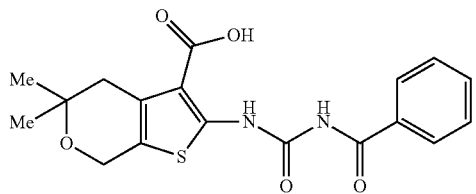

SID 99381130
CID 46916265

2-(3-Benzoylureido)-5,5-dimethyl-5,7-dihydro-4H-thieno[2,3-c]pyran-3-carboxylic acid (SID 99381130, CID46916265)

To a solution of tert-butyl 2-(3-benzoylureido)-5,5-dimethyl-5,7-dihydro-4H-thieno[2,3-c]pyran-3-carboxylate (0.105 g, 0.24 mmol, 1 equiv.) in DCM (10 mL) was added TFA (0.5 mL, 6.5 mmol, 27 equiv.), and the reaction was stirred at rt for 5 days. The solvent was removed under reduced pressure and the product was purified by preparatory HPLC (0-5% MeOH/DCM), followed by mass-directed reverse-phase chromatography and isolated as a white solid (6 mg, 7% yield). $^1$H NMR (400 MHz, DMSO) δ 13.11 (s, 1H), 11.39 (s, 1H), 8.05-7.99 (m, 2H), 7.69-7.63 (m, 1H), 7.55 (t, J=7.7 Hz, 2H), 4.62 (s, 2H), 2.71 (s, 2H), 1.22 (s, 6H). LCMS retention time: 2.872 min; LCMS purity at 215 nm=100%. HRMS m/z calculated for C$_{18}$H$_{19}$N$_2$O$_5$S [M$^+$+1]: 375.1009. found 375.1013.

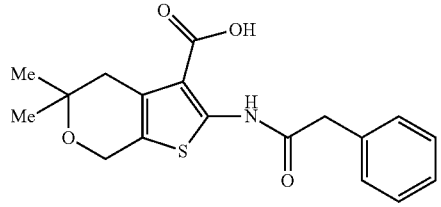

SID 99381117
CID 740871

5,5-dimethyl-2-(2-phenylacetamido)-5,7-dihydro-4H-thieno[2,3-c]pyran-3-carboxylic acid (SID 99381117, CID740871)

5,5-Dimethyl-2-(2-phenylacetamido)-5,7-dihydro-4H-thieno[2,3-c]pyran-3-carboxylic acid was purchased from ChemBridge (CAS 303966-15-6) and purified by mass-directed reverse-phase chromatography and isolated as a white solid (3 mg, 100% purity). $^1$H NMR (400 MHz, CDCl$_3$) δ 10.88 (s, 1H), 7.43-7.37 (m, 2H), 7.33 (dd, J=6.7, 4.3 Hz, 3H), 4.72 (s, 2H), 3.85 (s, 2H), 2.85 (s, 2H), 1.35 (s, 6H). LCMS retention time: 3.045 min; LCMS purity at 215 nm=100%. HRMS m/z calculated for C$_{18}$H$_{20}$NO$_4$S [M$^+$+1]: 346.1108. found 346.1110.

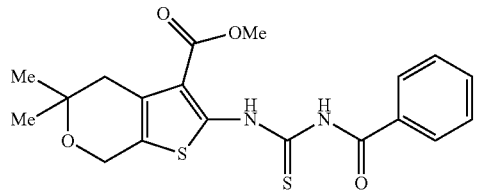

SID 99381118
CID 1251121

Methyl 2-(3-benzoylthioureido)-5,5-dimethyl-5,7-dihydro-4H-thieno[2,3-c]pyran-3-carboxylate (SID 99381118, CID1251121)

To a combined mixture of methyl 2-amino-5,5-dimethyl-5,7-dihydro-4H-thieno[2,3-c]pyran-3-carboxylate (ChemBridge, CAS 713111-73-0, 31 mg, 0.13 mmol, 1 equiv.) and PhCONCS (0.02 mL, 0.15 mmol, 1.2 equiv.) was added THF (0.7 mL) The resulting solution was stirred at 50° C. for 3 days. The solvent was then removed under reduced pressure and the crude product was triturated with hexanes, filtered, and rinsed with hexanes (4×5 mL). The product was further purified by preparatory HPLC (0-50% EtOAC:hexanes) and isolated as a white solid (38 mg, 72% yield). $^1$H NMR (400 MHz, CDCl$_3$) δ 14.83 (s, 1H), 9.14 (s, 1H), 7.98 (dd, J=8.4, 1.2 Hz, 2H), 7.72-7.63 (m, 1H), 7.56 (dd, J=10.5, 4.8 Hz, 2H), 4.77 (t, J=1.5 Hz, 2H), 4.04 (s, 3H), 2.85 (s, 2H), 1.35 (s, 6H). LCMS retention time: 3.508 min; LCMS purity at 215 nm=96%. HRMS m/z calculated for C$_{19}$H$_{21}$N$_2$O$_4$S$_2$ [M$^+$+1]: 405.0937. found 405.0942.

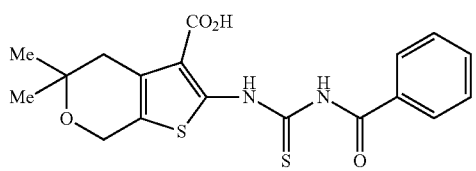

SID 85747738
CID 1067700

2-(3-benzoylthioureido)-5,5-dimethyl-5,7-dihydro-4H-thieno[2,3-c]pyran-3-carboxylic acid (SID 85747738/CID1067700)

2-(3-benzoylthioureido)-5,5-dimethyl-5,7-dihydro-4H-thieno[2,3-c]pyran-3-carboxylic acid was purchased from Chemdiv Inc. (CAS 314042-01-8) and purified by mass-directed reverse-phase chromatography to yield a white solid (6 mg). $^1$H NMR (400 MHz, DMSO) δ 14.84 (s, 1H), 13.39 (s, 1H), 11.81 (s, 1H), 7.98 (dd, J=1.2, 8.4, 2H), 7.74-7.62 (m, 1H), 7.55 (t, J=7.7, 2H), 4.67 (s, 2H), 2.75 (s, 2H), 1.24 (s, 6H). $^{13}$C NMR (101 MHz, DMSO) δ 174.43, 166.86, 165.35, 146.72, 133.08, 132.06, 129.10, 128.75, 128.41, 124.09, 116.50, 70.14, 58.82, 37.27, 26.19. LCMS retention time: 1.871 min; LCMS purity at 214 nm=92.8%. HRMS m/z calculated for $C_{18}H_{19}N_2O_4S_2$ [M$^+$+1]: 391.0781. found 391.0777.

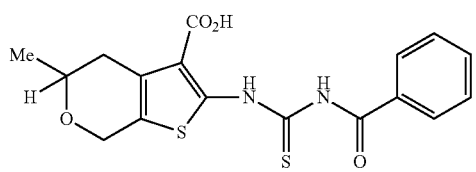

SID 9931128
CID 46916263

2-(3-benzoylthioureido)-5-methyl-5,7-dihydro-4H-thieno[2,3-c]pyran-3-carboxylic acid (SID 9931128/CID46916263)

To tert-butyl 2-(3-benzoylthioureido)-5-methyl-5,7-dihydro-4H-thieno[2,3-c]pyran-3-carboxylate (0.028 g, 0.065 mmol, 1 eq.) was added a 40% v/v solution of trifluoroacetic acid in dichloromethane (2.5 mL). After stirring the solution for 4 hours at rt, the solvent was evaporated in vacuo, and the residue purified by reverse-phase chromatography to yield the product as a white semi-solid (0.011 g, 0.029 mmol, 46% yield). $^1$H NMR (400 MHz, Acetone) δ 8.07 (d, J=7.4, 2H), 7.68 (t, J=7.0, 1H), 7.56 (t, J=7.5, 2H), 4.76 (q, J=14.7, 2H), 3.82-3.68 (m, 1H), 3.05 (d, 1H), 1.47 (d, J=6.5, 1H), 1.32 (d, J=6.1, 3H). $^{13}$C NMR (126 MHz, Acetone) δ 175.37, 166.92, 165.37, 161.89, 148.65, 134.12, 133.28, 131.39, 129.62, 129.28, 126.49, 71.61, 65.11, 35.05, 21.82. LCMS retention time: 3.095 min; Purity at 214 nm=93.3%. HRMS m/z calculated for $C_{17}H_{17}N_2O_4S_2$ [M$^+$+1] 377.0624. found 377.0622.

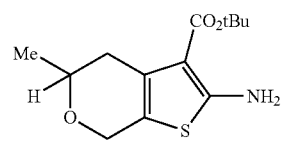

tert-butyl 2-amino-5-methyl-5,7-dihydro-4H-thieno[2,3-c]pyran-3-carboxylate

A mixture of 2-methyldihydro-2H-pyran-4(3H)-one (0.320 g, 2.80 mmol, 1 eq), tert-butyl cyanoacetate (0.44 mL, 3.08 mmol, 1.1 eq), sulfur (0.099 g, 3.08 mmol, 1.1 eq), morpholine (0.36 mL, 4.21 mmol, 1.5 eq), and ethanol (7 mL) was heated at 50° C. for 16 hours. The reaction mixture was then filtered, and the filter cake washed with ethyl acetate (20 mL). Purification by silica gel chromatography (0-30% EtOAc:Hex ramp over 20 min) afforded the desired product tert-butyl 2-amino-5-methyl-5,7-dihydro-4H-thieno[2,3-c]pyran-3-carboxylate as a pale yellow solid (0.745 g, 2.77 mmol, 99% yield). $^1$H NMR (400 MHz, CDCl$_3$) δ 5.90 (s, 2H), 4.71-4.49 (m, 2H), 3.82-3.65 (m, 1H), 2.86-2.73 (m, 1H), 2.52-2.37 (m, 1H), 1.52 (d, J=1.4, 9H), 1.31 (dd, J=2.1, 6.2, 3H).

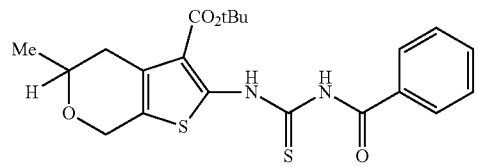 [SMILES: CC1Cc2c(sc(NC(=S)NC(=O)c3ccccc3)c2C(=O)OC(C)(C)C)CO1]

tert-butyl 2-(3-benzoylthioureido)-5-methyl-5,7-dihydro-4H-thieno[2,3-c]pyran-3-carboxylate To a solution of tert-butyl 2-amino-5-methyl-5,7-dihydro-4H-thieno[2,3-c]pyran-3-carboxylate (0.104 g, 0.386 mmol, 1 eq) in dry ethanol (1 mL) under argon was added benzoyl isothiocyanate (0.15 mL, 1.08 mmol, 2.8 eq). The mixture was heated at reflux for 16 hours. The solvent was evaporated in vacuo. Purification by reverse-phase chromatography (10-100% CH$_3$CN: Water ramp over 20 min) afforded the desired product tert-butyl 2-(3-benzoylthioureido)-5-methyl-5,7-dihydro-4H-thieno[2,3-c]pyran-3-carboxylate as a pale yellow oil (0.057 g, 0.132 mmol, 34% yield). $^1$H NMR (400 MHz, DMSO) δ 14.72 (s, 1H), 11.89 (s, 1H), 8.06-7.95 (m, 2H), 7.69 (t, J=7.4, 1H), 7.57 (t, J=7.7, 2H), 4.78 (d, J=14.8, 1H), 4.66 (d, J=15.0, 1H), 3.80-3.63 (m, 1H), 2.93 (d, J=16.7, 1H), 2.50-2.44 (m, 1H), 1.59 (s, 9H), 1.30 (d, J=6.1, 3H).

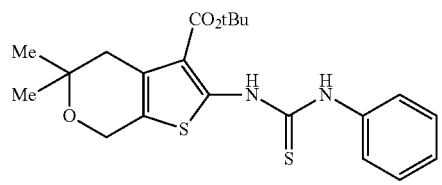 [SMILES: CC(C)(C)OC(=O)c1c(NC(=S)Nc2ccccc2)sc2c1CC(C)(C)OC2]

tert-butyl 5,5-dimethyl-2-(3-phenylthioureido)-5,7-dihydro-4H-thieno[2,3-c]pyran-3-carboxylate To a solution of tert-butyl 2-amino-5,5-dimethyl-5,7-dihydro-4H-thieno[2,3-c]pyran-3-carboxylate (0.100 g, 0.353 mmol, 1 eq) in dry tetrahyrofuran (5 mL) under argon was added phenyl isothiocyanate (0.05 mL, 0.388 mmol, 1.1 eq). The mixture was heated at reflux for 16 hours. The solvent was evaporated in vacuo. Purification by reverse-phase chromatography (0-100% CH$_3$CN: Water ramp over 20 min) afforded the desired product tert-butyl 5,5-dimethyl-2-(3-phenylthioureido)-5,7-dihydro-4H-thieno[2,3-c]pyran-3-carboxylate as a yellow solid (0.045 g, 0.108 mmol, 30% yield). $^1$H NMR (400 MHz, DMSO) δ 11.92 (s, 1H), 11.05 (s, 1H), 7.50 (d, J=7.6, 2H), 7.42 (t, J=7.9, 2H), 7.26 (t, J=7.3, 1H), 4.61 (s, 2H), 2.65 (s, 2H), 1.53 (s, 9H), 1.23 (s, 6H).

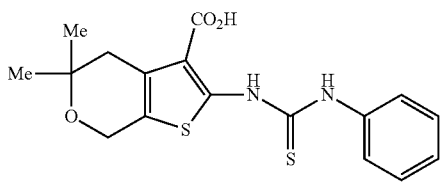 [SMILES: CC1(C)Cc2c(sc(NC(=S)Nc3ccccc3)c2C(=O)O)CO1]

5,5-dimethyl-2-(3-phenylthioureido)-5,7-dihydro-4H-thieno[2,3-c]pyran-3-carboxylic acid (SID 99381127/CID1280844)

To 5,5-dimethyl-2-(3-phenylthioureido)-5,7-dihydro-4H-thieno[2,3-c]pyran-3-carboxylic acid (0.037 g, 0.088 mmol, 1 eq.) was added a 40% v/v solution of trifluoroacetic acid in dichloromethane (2.5 mL). After stirring the solution for 4 hours at rt, the solvent was evaporated in vacuo and the residue purified by reverse-phase LCMS to yield the product as a white solid (0.020 g, 0.065 mmol, 63% yield). $^1$H NMR (400 MHz, Acetone) δ 7.97 (d, J=7.7, 2H), 7.88 (t, J=7.7, 2H), 7.73 (t, J=6.9, 1H), 4.32 (s, 2H), 3.11 (s, 2H), 1.73 (s, 6H). LCMS retention time: 3.113 min; Purity at 214 nm=100%. HRMS m/z calculated for C$_{17}$H$_{19}$N$_2$O$_3$S$_2$ [M$^+$+1] 363.0832. found 363.0829.

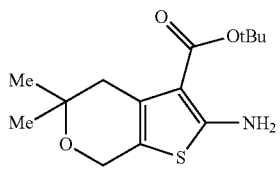 [SMILES: CC(C)(C)OC(=O)c1c(N)sc2c1CC(C)(C)OC2]

tert-Butyl-2-amino-5,5-dimethyl-5,7-dihydro-4H-thieno[2,3-c]pyran-3-carboxylate

Following a previously reported procedure,[42] a mixture of 2,2-dimethyldihydro-2H-pyran-4(3H)-one (0.30 g, 2.34 mmol, 1 eq), tert-butyl cyanoacetate (0.37 mL, 2.57 mmol, 1.1 eq), sulfur (0.083 g, 2.57 mmol, 1.1 eq), morpholine (0.30 mL, 3.51 mmol, 1.5 eq), and ethanol (7 mL) was heated at 50° C. for 16 h. The reaction mixture was then filtered, and the filter cake washed with ethyl acetate (20 mL). Purification by silica gel chromatography (0-20% EtOAc/Hex ramp over 20 min) afforded the desired product tert-butyl 2-amino-5,5-dimethyl-5,7-dihydro-4H-thieno[2,3-c]pyran-3-carboxylate as a yellow solid (0.63 g, 2.23 mmol, 95% yield). $^1$H NMR (400 MHz, CDCl$_3$) δ 5.88 (s, 2H), 4.52 (apparent t, J=1.9, 2H), 2.64 (apparent t, J=1.9, 2H), 1.53 (s, 9H), 1.26 (s, 6H). $^{13}$C NMR (101 MHz, CDCl$_3$) δ 165.22, 161.77, 130.07, 113.43, 106.94, 80.38, 70.83, 59.81, 38.72, 28.56, 26.46.

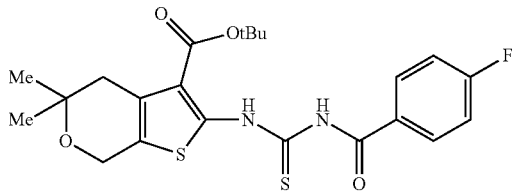 [SMILES: CC(C)(C)OC(=O)c1c(NC(=S)NC(=O)c2ccc(F)cc2)sc2c1CC(C)(C)OC2]

tert-Butyl-2-(3-(4-fluorobenzoyl)thioureido)-5,5-dimethyl-5,7-dihydro-4H-thieno[2,3-c]pyran-3-carboxylate tert-Butyl 2-amino-5,5-dimethyl-5,7-dihydro-4H-thieno[2,3-c]pyran-3-carboxylate (0.28 g, 1.00 mmol) and 4-fluorobenzoyl isothiocyanate (0.18 g, 0.99 mmol) were dissolved in THF (5 mL) and heated at 50° C. for 22 hours. The solvent was removed and EtOH (10 mL) was added. The product was filtered and rinsed with EtOH (2×10 mL). tert-Butyl 2-(3-(4-fluorobenzoyl)thioureido)-5,5-dimethyl-5,7-dihydro-4H-thieno[2,3-c]pyran-3-carboxylate (0.330 g, 0.71 mmol, 71% yield) was isolated as a pale yellow solid. $^1$H NMR (400 MHz, CDCl$_3$) δ 14.70 (s, 1H), 9.01 (s, 1H), 8.00-7.94 (m, 2H), 7.25-7.18 (m, 2H), 4.74 (apparent t, J=1.5 Hz, 2H), 2.76 (apparent t, J=1.5 Hz, 2H), 1.64 (s, 9H), 1.31 (s, 6H).

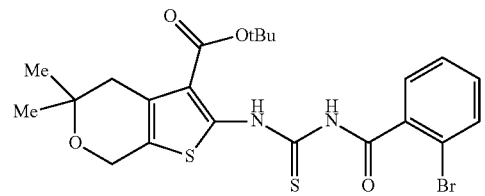 [SMILES: CC(C)(C)OC(=O)c1c(NC(=S)NC(=O)c2ccccc2Br)sc2c1CC(C)(C)OC2]

tert-Butyl-2-(3-(2-bromobenzoyl)thioureido)-5,5-dimethyl-5,7-dihydro-4H-thieno[2,3-c]pyran-3-carboxylate tert-Butyl 2-amino-5,5-dimethyl-5,7-dihydro-4H-thieno[2,3-c]pyran-3-carboxylate (0.28 g, 1.00 mmol) and 2-bromobenzoyl isothiocyanate (0.24 g, 1.00 mmol) were dissolved in THF (5 mL) and heated at 50° C. for 22 hours. The solvent was removed and EtOH (10 mL) was added. The product was filtered and rinsed with EtOH (2×10 mL). tert-Butyl 2-(3-(2-bromobenzoyl)thioureido)-5,5-dimethyl-5,7-dihydro-4H-thieno[2,3-c]pyran-3-carboxylate (0.26 g, 0.49 mmol, 49% yield) was isolated as a white solid. $^1$H NMR (400 MHz, CDCl$_3$) δ 14.64 (s, 1H), 9.04 (s, 1H), 7.75 (apparent dd, J=7.6, 1.8 Hz, 1H), 7.67 (apparent dd, J=7.9, 1.1 Hz, 1H), 7.45 (apparent td, J=7.5, 1.3 Hz, 1H), 7.40 (apparent td, J=7.7, 1.9 Hz, 1H), 4.74 (apparent t, J=1.5 Hz, 2H), 2.77 (t, J=1.5 Hz, 2H), 1.63 (s, 9H), 1.31 (s, 6H).

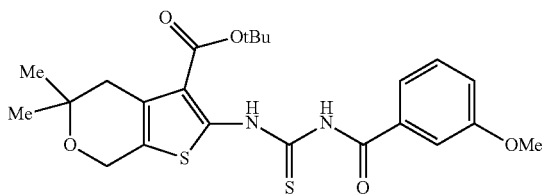 [SMILES: COc1cccc(C(=O)NC(=S)Nc2sc3c(c2C(=O)OC(C)(C)C)CC(C)(C)OC3)c1]

tert-Butyl-2-(3-(3-methoxybenzoyl)thioureido)-5,5-dimethyl-5,7-dihydro-4H-thieno[2,3-c]pyran-3-carboxylate tert-Butyl 2-amino-5,5-dimethyl-5,7-dihydro-4H-thieno[2,3-c]pyran-3-carboxylate (0.28 g, 1.00 mmol) and 3-methoxybenzoyl isothiocyanate (0.20 g, 1.01 mmol) were dissolved in THF (5 mL) and heated at 50° C. for 22 hours. The solvent was removed and EtOH (10 mL) was added. The product was filtered and rinsed with EtOH (2×10 mL). tert-Butyl-2-(3-(3-methoxybenzoyl)thioureido)-5,5-dimethyl-5,7-dihydro-4H-thieno[2,3-c]pyran-3-carboxylate (0.32 g, 0.68 mmol, 68% yield) was isolated as a pale yellow solid. $^1$H NMR (400 MHz, CDCl$_3$) δ 14.71 (s, 1H), 9.06 (s, 1H), 7.51-7.49 (m, 1H), 7.44-7.40 (m, 2H), 7.19-7.13 (m, 1H), 4.74 (apparent t, J=1.5 Hz, 2H), 3.89 (s, 3H), 2.77 (apparent t, J=1.5 Hz, 2H), 1.64 (s, 9H), 1.31 (s, 6H).

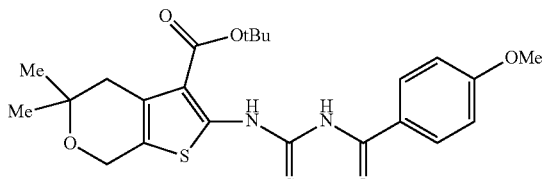

tert-Butyl-2-(3-(4-methoxybenzoyl)thioureido)-5,5-dimethyl-5,7-dihydro-4H-thieno[2,3-c]pyran-3-carboxylate A solution of tert-butyl 2-amino-5,5-dimethyl-5,7-dihydro-4H-thieno[2,3-c]pyran-3-carboxylate (1.0 mL, 0.083 M, 0.083 mmol) in THF was added to a solution of 4-methoxybenzoyl isothiocyanate (51 mg, 0.26 mmol) in THF (1 mL) and heated at 50° C. for 16 hours, then cooled to room temperature. The solvent was removed and EtOH (2 mL) was added. The product was filtered and rinsed with EtOH (3×5 mL). tert-Butyl 2-(3-(4-methoxybenzoyl)thioureido)-5,5-dimethyl-5,7-dihydro-4H-thieno[2,3-c]pyran-3-carboxylate (31 mg, 0.065 mmol, 78% yield) was isolated as a white solid. $^1$H NMR (400 MHz, CDCl$_3$) δ 14.65 (s, 1H), 8.98 (s, 1H), 7.83 (apparent d, J=8.9 Hz, 2H), 6.91 (apparent d, J=8.9 Hz, 2H), 4.66 (s, 2H), 3.81 (s, 3H), 2.69 (s, 2H), 1.56 (s, 9H), 1.24 (s, 6H). $^{13}$C NMR (101 MHz, CDCl$_3$) 173.90, 164.52, 164.49, 163.88, 147.40, 129.93, 129.13, 124.58, 123.65, 118.03, 114.34, 82.36, 70.79, 59.81, 55.62, 38.25, 28.49, 26.48.

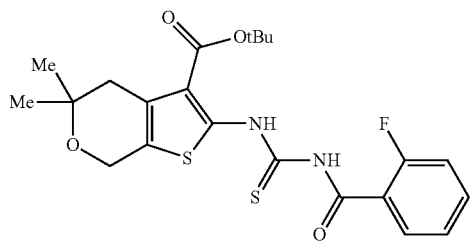 [SMILES: CC(C)(C)OC(=O)c1c(NC(=S)NC(=O)c2ccccc2F)sc2c1CC(C)(C)OC2]

tert-Butyl-2-(3-(2-fluorobenzoyl)thioureido)-5,5-dimethyl-5,7-dihydro-4H-thieno[2,3-c]pyran-3-carboxylate To a solution of tert-butyl 2-amino-5,5-dimethyl-5,7-dihydro-4H-thieno[2,3-c]pyran-3-carboxylate (50 mg, 0.18 mmol) in THF (3 mL) was added 2-fluorobenzoyl isothiocyanate (35.2 mg, 0.19 mmol) and the mixture heated at 60° C. for 16 h. The solvent was removed in vacuo. The residue was sonicated (1 min) with cold EtOH, filtered and the resulting solid rinsed with cold EtOH to yield tert-butyl 2-(3-(2-fluorobenzoyl)thioureido)-5,5-dimethyl-5,7-dihydro-4H-thieno[2,3-c]pyran-3-carboxylate (41 mg, 0.088 mmol, 50% yield) as a pale yellow solid. $^1$H NMR (400 MHz, CDCl$_3$) δ 14.70 (s, 1H), 9.69 (s, 1H), 8.25-8.11 (m, 1H), 7.63-7.49 (m, 1H), 7.36-7.26 (m, 1H), 7.23-7.17 (m, 1H), 4.72 (s, 2H), 2.73 (d, J=6.3, 2H), 1.58 (d, J=2.4, 9H), 1.29 (d, J=1.7, 6H). $^{13}$C NMR (101 MHz, CDCl$_3$) δ 173.27, 164.59, 161.79, 161.21, 161.18, 159.30, 147.36, 135.67, 135.57, 132.79, 129.15, 125.37, 125.34, 124.64, 119.06, 118.96, 118.06, 116.70, 116.46, 82.42, 70.79, 59.81, 38.24, 28.49, 26.48.

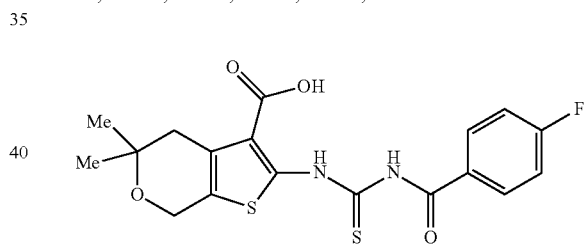

SID 125299368

2-(3-(4-Fluorobenzoyl)thioureido)-5,5-dimethyl-5,7-dihydro-4H-thieno[2,3-c]pyran-3-carboxylic acid (SID 125299368)

A solution of 40% v/v TFA/DCM (20 mL) was added to tert-butyl 2-(3-(4-fluorobenzoyl)thioureido)-5,5-dimethyl-5,7-dihydro-4H-thieno[2,3-c]pyran-3-carboxylate (0.33 g, 0.71 mmol) and the mixture was stirred at RT for 1 hour. The volatiles were removed at 30° C. and the material was purified by reverse-phase chromatography (10-100% MeCN/water). 2-(3-(4-Fluorobenzoyl)thioureido)-5,5-dimethyl-5,7-dihydro-4H-thieno[2,3-c]pyran-3-carboxylic acid (0.21 g, 0.51 mmol, 72% yield) was isolated as a pale, yellow solid. $^1$H NMR (400 MHz, DMSO) δ 14.81 (s, 1H), 13.36 (s, 1H), 11.83 (s, 1H), 8.11-8.00 (m, 2H), 7.38 (apparent t, J=8.9 Hz, 2H), 4.66 (s, 2H), 2.74 (s, 2H), 1.23 (s, 6H). $^{13}$C NMR (101 MHz, DMSO) δ 174.33, 166.13, 165.72, 165.35, 163.63, 146.76, 131.80, 131.70, 129.08, 128.60, 128.57, 124.06, 116.48, 115.54, 115.32, 70.12, 58.80, 37.25, 26.16. LCMS retention time: 3.206 min; LCMS purity at 214 nm=98%.

HRMS m/z calculated for $C_{18}H_{18}FN_2O_4S_2$ [$M^+$+1]: 409.0687. found 409.0687. Melting point 205.3° C., decomposition.

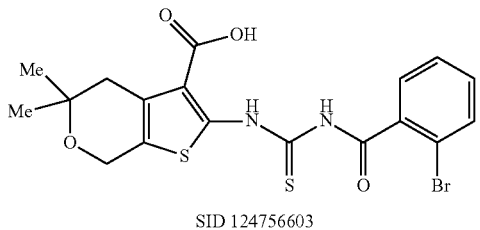 [SMILES: CC1(C)Cc2c(sc(NC(=S)NC(=O)c3ccccc3Br)c2C(=O)O)CO1]

SID 124756603

2-(3-(2-Bromobenzoyl)thioureido)-5,5-dimethyl-5,7-dihydro-4H-thieno[2,3-c]pyran-3-carboxylic acid (SID 124756603)

A solution of 40% v/v TFA/DCM (13.4 mL) was added to tert-butyl 2-(3-(2-bromobenzoyl)thioureido)-5,5-dimethyl-5,7-dihydro-4H-thieno[2,3-c]pyran-3-carboxylate (0.25 g, 0.48 mmol) and the mixture was stirred at room temperature for 1 h. The volatiles were removed at 30° C. and the material was purified by reverse-phase chromatography (10-100% MeCN/water). 2-(3-(2-Bromobenzoyl)thioureido)-5,5-dimethyl-5,7-dihydro-4H-thieno[2,3-c]pyran-3-carboxylic acid (0.16 g, 0.33 mmol, 69% yield) was isolated as a pale, yellow solid. $^1$H NMR (400 MHz, DMSO) δ 14.70 (s, 1H), 13.48 (s, 1H), 12.21 (s, 1H), 7.72 (apparent dd, J=7.8, 1.2 Hz, 1H), 7.62 (apparent dd, J=7.4, 1.8 Hz, 1H), 7.53-7.42 (m, 2H), 4.66 (s, 2H), 2.75 (s, 2H), 1.23 (s, 6H). $^{13}$C NMR (101 MHz, DMSO) δ 174.29, 167.42, 165.95, 147.16, 137.00, 133.01, 132.56, 129.70, 129.60, 128.04, 124.63, 119.33, 116.98, 70.62, 59.29, 37.74, 26.65. LCMS retention time: 3.193 min; LCMS purity at 214 nm=98%. HRMS m/z calculated for $C_{18}H_{18}BrN_2O_4S_2$ [$M^+$+1]: 468.9886. found 468.9860. Melting point 188.4° C., decomposition.

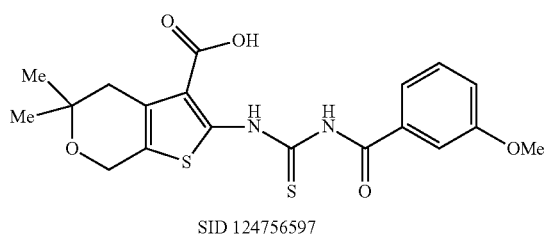 [SMILES: COc1cccc(C(=O)NC(=S)Nc2sc3c(c2C(=O)O)CC(C)(C)OC3)c1]

SID 124756597

2-(3-(3-Methoxybenzoyl)thioureido)-5,5-dimethyl-5,7-dihydro-4H-thieno[2,3-c]pyran-3-carboxylic acid (SID 124756597)

A solution of 40% v/v TFA/DCM (20 mL) was added to tert-butyl 2-(3-(3-methoxybenzoyl)thioureido)-5,5-dimethyl-5,7-dihydro-4H-thieno[2,3-c]pyran-3-carboxylate (0.32 g, 0.67 mmol) and the mixture was stirred at room temperature for 1 h. The volatiles were removed at 30° C. and the material was purified by reverse-phase chromatography (10-100% MeCN/water). 2-(3-(3-Methoxybenzoyl)thioureido)-5,5-dimethyl-5,7-dihydro-4H-thieno[2,3-c]pyran-3-carboxylic acid (0.114 g, 0.26 mmol, 39% yield) was isolated as a pale, yellow solid. $^1$H NMR (500 MHz, DMSO) δ 14.84 (s, 1H), 13.39 (s, 1H), 11.78 (s, 1H), 7.58-7.54 (m, 1H), 7.54-7.51 (m, 1H), 7.45 (apparent t, J=7.9 Hz, 1H), 7.22 (apparent ddd, J=8.3, 2.6, 0.9 Hz, 1H), 4.66 (s, 2H), 3.85 (s, 3H), 2.74 (s, 2H), 1.23 (s, 6H). $^{13}$C NMR (126 MHz, DMSO) δ 174.24, 166.41, 165.25, 158.88, 146.70, 133.23, 129.51, 128.99, 123.98, 120.94, 119.29, 116.40, 113.19, 70.04, 58.71, 55.33, 37.16, 26.08. LCMS retention time: 3.199 min; LCMS purity at 214 nm=97%. HRMS m/z calculated for $C_{19}H_{21}N_2O_5S_2$ [$M^+$+1]: 421.0886. found 421.0889. Melting point 199.3° C., decomposition.

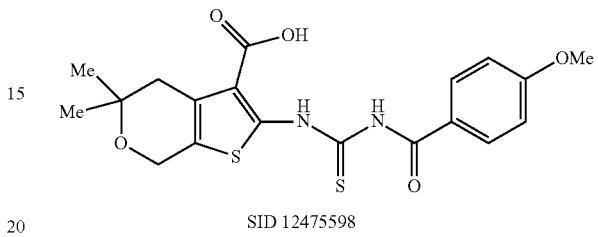

SID 12475598

2-(3-(4-Methoxybenzoyl)thioureido)-5,5-dimethyl-5,7-dihydro-4H-thieno[2,3-c]pyran-3-carboxylic acid (SID 124756598)

A solution of 40% v/v TFA/DCM (2.5 mL total) was added to tert-butyl 2-(3-(4-methoxybenzoyl)thioureido)-5,5-dimethyl-5,7-dihydro-4H-thieno[2,3-c]pyran-3-carboxylate (34 mg, 0.071 mmol) and the mixture was stirred at room temperature for 1 h. The volatiles were removed at 30° C. and the material was purified by mass-directed reverse-phase chromatography. 2-(3-(4-Methoxybenzoyl)thioureido)-5,5-dimethyl-5,7-dihydro-4H-thieno[2,3-c]pyran-3-carboxylic acid (14 mg, 0.033 mmol, 46% yield) as a white solid. $^1$H NMR (500 MHz, DMSO) δ 14.86 (s, 1H), 13.38 (s, 1H), 11.59 (s, 1H), 8.04-7.97 (m, 2H), 7.11-7.03 (m, 2H), 4.65 (s, 2H), 3.86 (s, 3H), 2.73 (s, 2H), 1.22 (s, 6H). $^{13}$C NMR (126 MHz, DMSO) δ 174.55, 165.94, 165.28, 163.16, 146.98, 131.01, 129.02, 123.95, 123.75, 116.39, 113.76, 70.12, 58.80, 55.58, 37.25, 26.16. LCMS retention time: 3.264 min; LCMS purity at 214 nm=99%. HRMS m/z calculated for $C_{19}H_{21}N_2O_5S_2$ [$M^+$+1]: 421.0886. found 421.0893. Melting point 213.2° C., decomposition.

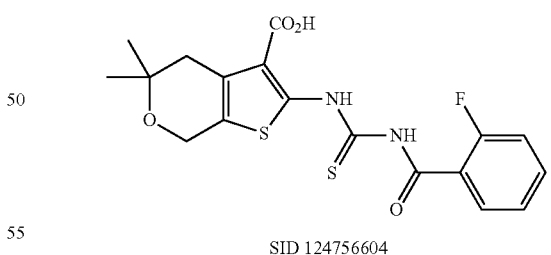

SID 124756604

2-(3-(2-fluorobenzoyl)thioureido)-5,5-dimethyl-5,7-dihydro-4H-thieno[2,3-c]pyran-3-carboxylic acid (SID 124756604)

To tert-butyl 2-(3-(2-fluorobenzoyl)thioureido)-5,5-dimethyl-5,7-dihydro-4H-thieno[2,3-c]pyran-3-carboxylate (36 mg, 0.077 mmol) was added a solution of 2,2,2-trifluoroacetic acid (0.75 mL, 9.76 mmol) in $CH_2Cl_2$ (1.1 mL) [40% v/v] and the mixture stirred at RT for 1 h. The solvent was evaporated in vacuo and the residue chromatographed using reversed-phase MPLC (0-100% ACN—H$_2$O; 40 g C18 column) to yield 2-(3-(2-fluorobenzoyl)thioureido)-5,5-dimethyl-5,7-dihydro-4H-thieno[2,3-c]pyran-3-carboxylic acid (10.5 mg, 0.026 mmol, 33% yield) as a pale yellow solid. $^1$H NMR (500 MHz, DMSO) δ 14.70 (s, 1H), 11.94 (s, 1H), 7.72 (apparent d, J=7.3, 1H), 7.65 (s, 1H), 7.38-7.32 (m, 2H), 4.65 (s, 2H), 2.73 (s, 2H), 1.22 (s, 6H). $^{13}$C NMR (126 MHz, DMSO) δ 173.69, 165.48, 163.91, 160.34, 158.35, 146.81, 134.19, 134.12, 130.50, 129.19, 124.64, 124.61, 124.24, 122.28, 122.17, 116.60, 116.32, 116.14, 70.20, 58.87, 37.32, 26.23. LCMS retention time: 3.275 min; LCMS purity at 214 nm=99.6%. HRMS m/z calculated for C$_{18}$H$_{18}$FN$_2$O$_4$S$_2$ [M$^+$+1]: 409.0687. found 409.0687. Melting point 202.8° C., decomposition.

Materials and Instrumentation

GST-tagged GTPases were from Cytoskeleton (Denver, Colo.) and Rab7 was purified by the assay provider. BODIPY (4,4-difluoro-4-bora-3a,4a-diaza-s-indacene or dipyrromethene boron difluoride) nucleotide analogues (BODIPY FL GTP 2'-(or 3')-O—[N-(2-aminoethyl)urethane] G-35778 and BODIPY FL GDP 2'-(or -3')—O—[N-(2-aminoethyl) urethane], G-22360) were from Invitrogen Molecular Probes (Carlsbad, Calif.). 2-(benzoylcarbamothioylamino)-5,5-dimethyl-4, 7-dihydrothieno[2,3-c]pyran-3-carboxylic acid with compound identification number (CID) 1067700 was from ChemDiv and from University of Kansas Specialized Chemistry Center, which also supplied analogs to CID1067700. Detergents Nonidet P-40 and Tween 20 were from Sigma (St. Louis, Mo.) and Bio-Rad (Hercules, Calif.), respectively. Precision Plus Protein™ Standards were also purchased from Bio-Rad. For cell permeabilization, CelLytic™M Cell Lysis Reagent, Protein Inhibitor Cocktail for Mammalian Cells and phenylmethanesulfonyl fluoride were from Sigma. BCA protein assay kit was from Thermo Fisher Scientific (Waltham, Mass.). EGF Receptor Rabbit mAb was from Cell Signaling (Danvers, Mass.). Anti-actin antibody produced in rabbit was from Sigma. Stabilized goat anti-rabbit IgG with peroxidase conjugated and SuperSignal West Dura were from Thermo Fisher Scientific. Recombinant human epidermal growth factor, EGF, was purchased from Invitrogen. Cycloheximide was from Sigma. The sequences of peptide LDV, FITC-LDV, and N-formyl peptide have been described before [36] and are products of Biogen Idec (San Diego, Calif.).

The CyAn$_{ADP}$ flow instrument and Biomek FX are products of Beckman Coulter (Indianapolis, Ind.). Low volume transfers (100 nL) were done via pintool (V&P Scientific; San Diego, Calif.). FACScan flow instrument is from Becton Dickinson (Franklin Lakes, N.J.). Cyto-Plex™ Microspheres (4.0 µm) are from Thermo Fisher Scientific. Quantum™ FITC-5MESF is from Bangs Laboratories, Inc (Fishers, Ind.). Countess Cell Counter is from Life Technologies (Carlsbad, Calif.). The HyperCyt system is from Intellicyt (Albuquerque, N. Mex.). ChemiDoc™ XRS+ molecular imager is from Bio-Rad. HyperView software (version 2.5.1, IntelliCyt) was modified to enable specialized analysis functions used in these studies.

Cell Culture

U937 ΔST cells (a gift from Dr. Eric Prossnitz, Dept. Cell Biology and Physiology, University of New Mexico, Albuquerque, N. Mex.) were grown at 37° C. in a humidified incubator with 5% CO$_2$ and 95% air in RPMI 1640 supplemented with 2 mM L-glutamine, 100 units/mL penicillin, 100 µg/mL streptomycin, and 10% heat-inactivated fetal bovine serum. SCC-12F cells (a gift from Dr. Laurie Hudson, Department of Pharmaceutical Sciences, University of New Mexico, College of Pharmacy, Albuquerque, N. Mex.) were grown in a 1:1 mixture of DMEM and nutrient mixture F-12 Ham's medium supplemented with 10% fetal bovine serum. HeLa cells stably overexpressing Rab7 wild-type (a gift from Dr. Matthew Seaman, Dept. Clinical Biochemistry, Cambridge Institute for Medical Research, Cambridge, UK) were grown in MEM with 10% serum or MEM without serum during starvation.

Assays

Dose-Response Inhibition

The compound was serially diluted 3-fold and the resulting concentrations in the reactions ranged from 100 µM to 15 nM. The eight GTPases were grouped into two sets: Rab7, H-Ras wild type and its V12 mutant, and Cdc42 and its L61 mutant were assayed in a buffer containing 1 mM EDTA, while Rho, Rac1 and its L61 mutant, and Cdc42 and its L61 mutant were assayed in the same buffer but instead containing 1 mM Mg$^{2+}$ with Cdc42 and its mutant being tested in both buffers. Besides 1 mM EDTA or 1 mM Mg$^{2+}$, the buffer contained 30 mM HEPES, pH 7.5, 40 mM KCl, 100 mM NaCl, 0.1% (v/v) NP-40 and 1% BSA. For each multiplex reaction, an extra set of beads was included to serve as scavengers to bind any proteins that dissociate from their assigned bead set and thereby reduce interference due to protein dissociation during the assay. As a control, GST-tagged GFP was bound to a set of glutathione beads in a separate reaction to make sure that the fluorescence drop observed in the assay reaction in the presence of a compound was not due to fluorescence quenching of GFP nor interference of GST-tagged protein binding to beads, but due to the bona fide inhibition of fluorescent nucleotide binding. The assay protocol has been described previously [29-30]. Briefly, each individual GST-tagged enzyme was incubated with 4 µm glutathione-coated microsphere beads overnight with gentle rotation. The microsphere beads have different red fluorescence dyes incorporated and therefore could be separated by a flow cytometer. The unbound enzyme was removed by sufficient washing with the buffer. The bead sets were then combined and dispensed to 384-well plates at 5 µL/well. For one plate, 0.5 µg each of the enzymes and 4.0×10$^4$ of each bead were used. Then 100 nL compound was added using Biomek FX followed by the addition of 5 µL/well of BODIPY-FL-GTP (ribose-linked BODIPY). For assays carried out in EDTA-containing buffer, the final concentration of BODIPY-FL-GTP was 100 nM while in Mg buffer, the concentration of BODIPY-FL-GTP was 1 nM. The plate was incubated at 4° C. for 2 h with gentle rotation. The beads were aspirated and delivered with the HyperCyt® instrument and read on CyAnADP flow cytometer. Forward scatter and side scatter was used to define the whole bead population. FL9 channel (ext/em: 635/750LP nm) was used to separate different bead sets each of which was bound with an individual enzyme. FL1 channel (ext/em: 488/530 nm) measures the FITC fluorescence associated with the beads. The data was analyzed by the HyperView® software developed by Dr. Bruce Edward at the University of New Mexico.

Secondary Assays

Cytotoxicity of Compounds

U937 cells were grown to a density of 0.4×10$^6$ cells/mL Compounds were added to a final concentration of 20 µM or otherwise indicated. As a control, cells were treated with DMSO of the same volume. After 24 h incubation, the density and viability of the cells were measured with Countess Cell Counter according to the protocols from the manufacturer.

LDV Binding Assay (FIG. 26)

The procedure followed the established protocols described previously [36-38]. U937 ΔST cells (0.4–0.8×10$^6$ cells/mL) were constantly stirred with a magnetic stir bar at 500 rpm in a test tube. The fluorescence was recorded on a FACScan flow cytometer. The base line fluorescence of the cells was established for 30s. FITC-LDV at a concentration of 4 nM was then added. After the fluorescence stabilized at around 120s, the chemotactic ligand N-formyl peptide was added for stimulation resulting activation of VLA-4 integrin and additional FITC-LDV binding. When a plateau was reached at around 280s, compounds at different concentrations were added to the cell suspension. Fluorescence was continually recorded until no further change was observed. The inhibition percentage was calculated according to Equation 1.

$$\text{Inhibition percentage} = \left(1 - \frac{\text{remaining fluorescense after compound treatment}}{\text{fluorescence after } DMSO \text{ treatment}}\right) * 100\% \quad \text{(Equation 1)}$$

FITC-LDV Dissociation Assay (FIGS. 27-28)

The dissociation kinetics of FITC-LDV was measured by the addition of 100-fold of non-fluorescent LDV (The kinetic constants obtained are the same within experimental errors whether adding 100-fold or 200-fold of non-fluorescent LDV) [36,38]). The fluorescence decrease was recorded. For the resting state, when a fluorescence plateau was reached after the addition of FITC-LDV, LDV was added to the cell suspension. For the high affinity state, when the fluorescence reached equilibrium after the sequential addition of FITC-LDV and N-formyl peptide, LDV was added. To study the compounds effect, LDV was added at the time point when the fluorescence dropped to the minimum. The fluorescence decrease curve was fitted to either Equation 2 to obtain the dissociation rate constant $k_{off}$, or Equation 3 to calculate the active receptor percentage according to equation 4. In Equation 3, kh is the dissociation constant when the integrin is at the high affinity state while kl is the dissociation constant at the resting state. The values are 0.014 s$^{-1}$ and 0.036 s$^{-1}$, respectively, as determined in separate experiments using Equation 2.

$$y = A^* \exp(-k\text{off}^* x) + C \quad \text{(Equation 2)}$$

$$y = Ah^* \exp[(-kh]^* x) + Al^* \exp(-kl^* x) + C \quad \text{(Equation 3)}$$

$$\text{Active receptor percentage} = Ah/(Ah + Al) * 100\% \quad \text{(Equation 4)}$$

EGFR Degradation in SCC-12F Cells (FIG. 18b)

SCC-12F cells were seeded in 12-well plates at 0.12×10$^6$ cells/well and allowed to grow overnight. On the day of the experiment, the cells were starved in serum free medium containing 25 µg/mL cycloheximide for 2 h before compounds at different concentrations were added. The cells were treated for 30 min. Then, ligand EGF was added to 20 nM. At time points of 0, 15, 30, 60, and 120 min after the EGF addition, the suspension medium was removed and the cell was quickly washed with cold PBS and frozen at −80° C. For electrophoresis and blotting, CelLytic™M Cell Lysis buffer containing protease inhibitor cocktails was added to the frozen cells to obtain the cell lysates according to the protocols from the manufacture. Protein concentration was quantified using BCA assay kit. For SDS-PAGE, 10 µg protein was loaded to each lane and proteins transferred to nitrocellulose. The nitrocellulose membranes were probed with antibodies directed against EGFR or actin and detected using peroxidase conjugated secondary antibodies and SuperSignal West Dura.

Signal intensities were measured and quantified using a ChemiDoc™ XRS+ molecular imager coupled with Image Lab software.

EGFR Degradation in Rab7 Overexpressing HeLa Cells (FIG. 18c)

EGFR degradation was also monitored in HeLa cells with some minor modifications. Briefly, HeLa cells overexpressing GFP-Rab7 wild-type protein were serum starved overnight, incubated with 100 µM ML282 or CID1067700 for 3 h, and then treated with cycloheximide and stimulated with 100 ng/ml EGF in serum free medium for 0-180 min. Cell lysates were prepared at various time points and immunoblotted for total EGFR while actin served as a loading control.

Probe Chemical Characterization

A. Probe Chemical Structure, Physical Parameters and Probe Properties:

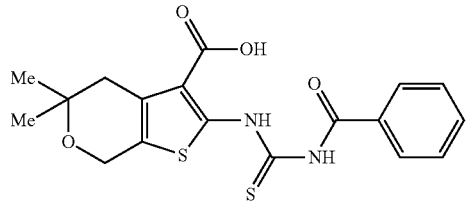

SID85747738
CID1067700
ML282

Molecular Formula: C$_{18}$H$_{18}$N$_2$O$_4$S$_2$
Molecular Weight: 390.48 [g/mol]
Exact Mass: 390.07 [g/mol]
CLogP: 3.5956
Topological Polar Surface Area: 87.66
Purity (LCMS, 214 nm): 92.8%
Physical State: white solid
Decomposition Point: 217.0° C.

Figure 6:
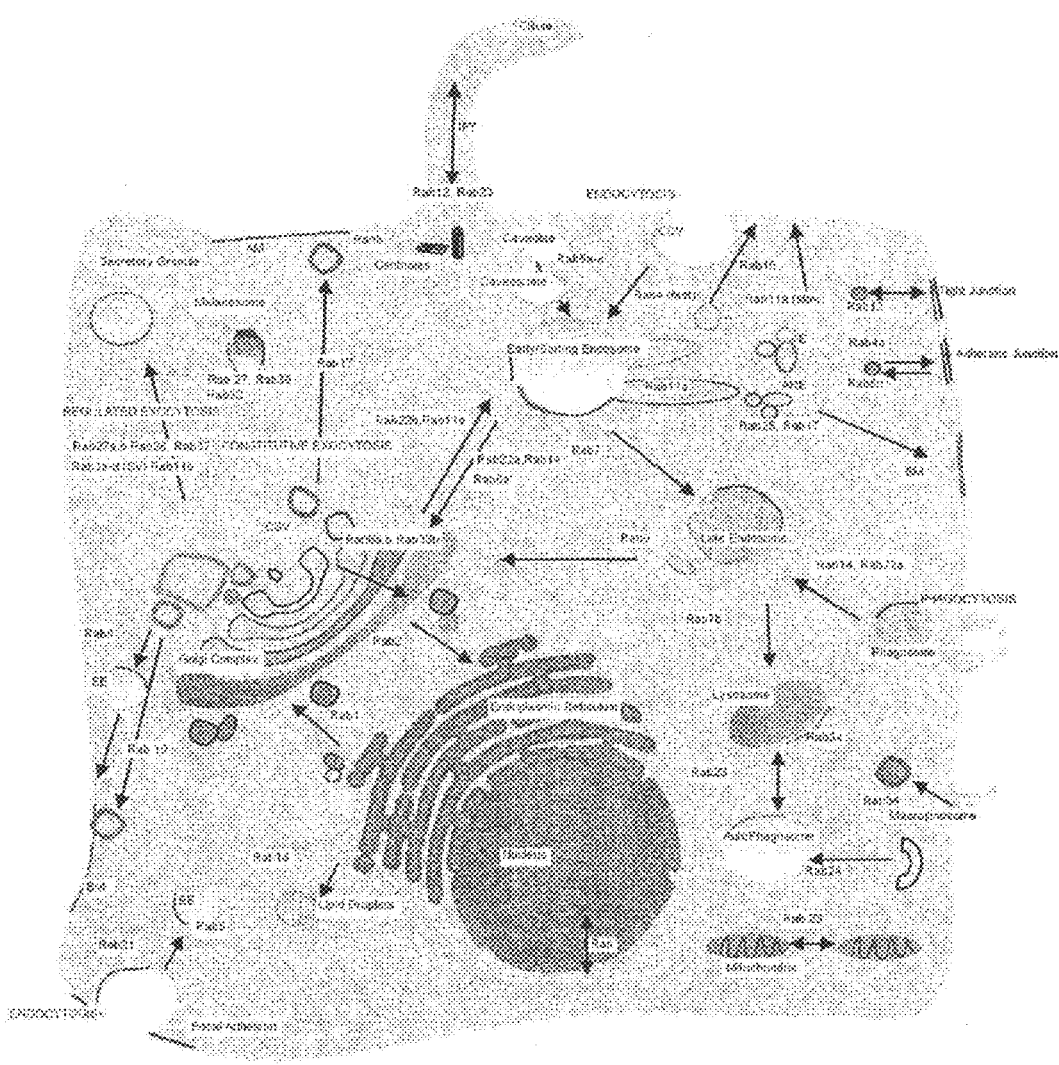
FIG. 6: Illustrates regulation of membrane trafficking by Rab GTPases.

B. Structure Verification and Purity: $^1$H NMR, $^{13}$C NMR, LCMS, and HRMS Data Proton and carbon NMR data for CID1067700:

Detailed analytical methods and instrumentation are described in section 2.3, entitled "Probe Preparation" under general experimental and analytical details. The numerical experimental proton and carbon data are represented below. The experimental proton and carbon spectra are included for reference (Appendix, FIGS. 6A and 6B, respectively).

Proton NMR Data for CID1067700:

$^1$H NMR (400 MHz, DMSO-d$_6$) δ 14.84 (s, 1H), 13.39 (s, 1H), 11.81 (s, 1H), 7.98 (apparent dd, J=1.2, 8.4, 2H), 7.74-7.62 (m, 1H), 7.55 (apparent t, J=7.7, 2H), 4.67 (s, 2H), 2.75 (s, 2H), 1.24 (s, 6H).

Carbon NMR Data for CID1067700:

$^{13}$C NMR (101 MHz, DMSO-d$_6$) δ 174.43, 166.86, 165.35, 146.72, 133.08, 132.06, 129.10, 128.75, 128.41, 124.09, 116.50, 70.14, 58.82, 37.27, 26.19.

LCMS and HRMS Data for CID1067700:

Detailed analytical methods and instrumentation are described in section 2.3, entitled "Probe Preparation" under general experimental and analytical details. The numerical experimental LCMS and HRMS data are represented below. LCMS retention time: 1.871 min. LCMS purity at 214 nm: 92.8%. HRMS: m/z calculated for C$_{18}$H$_{19}$N$_2$O$_4$S$_2$ [M$^+$+1]: 391.0781. found 391.0777. The experimental LCMS and HRMS spectra are included for reference (Appendix, FIGS. 6C and 6D, respectively).

C. Solubility:

Solubility was measured in phosphate buffered saline (PBS) at room temperature (23° C.). PBS by definition is 137 mM NaCl, 2.7 mM KCl, 10 mM sodium phosphate dibasic, 2 mM potassium phosphate monobasic and a pH of 7.4. Detection was based on UV absorbance [39,40]. Probe ML282 or CID1067700 (SID 85747738) was found to have an excellent PBS solubility measurement of >116 μg/mL, or >297 μM, under these conditions. Solubility was also assessed in the each of the four media used in the individual assays. Probe ML282 (SID 85747738) was determined to have excellent assay media solubility, as depicted in Table 1, below.

TABLE 1

Solubility for CID1067700 in Assay Media

| | Assay Conditions | | | |
|---|---|---|---|---|
| | Dose Response-EDTA buffer: 30 mM HEPES, pH 7.5, 100 mM KCl, 20 mM NaCl, 0.01% (v/v) NP-40, 1 mM EDTA | Dose Response-Mg buffer: 30 mM HEPES, pH 7.5, 100 mM KCl, 20 mM NaCl, 0.01% (v/v) NP-40, 1 mM MgCl2 | LDV-FITC assay buffer: RPMI 1640 +10% HI-FBS) | EGFR degradation assay medium: DMEM/F-12, Invitrogen # 11320-082) |
| ML282 Solubility mg/mL | 69.7 | 68.1 | >116 | >116 |
| ML282 Solubility mM | 178.5 | 174.4 | 297.1 | 297.1 |

Figure 23:
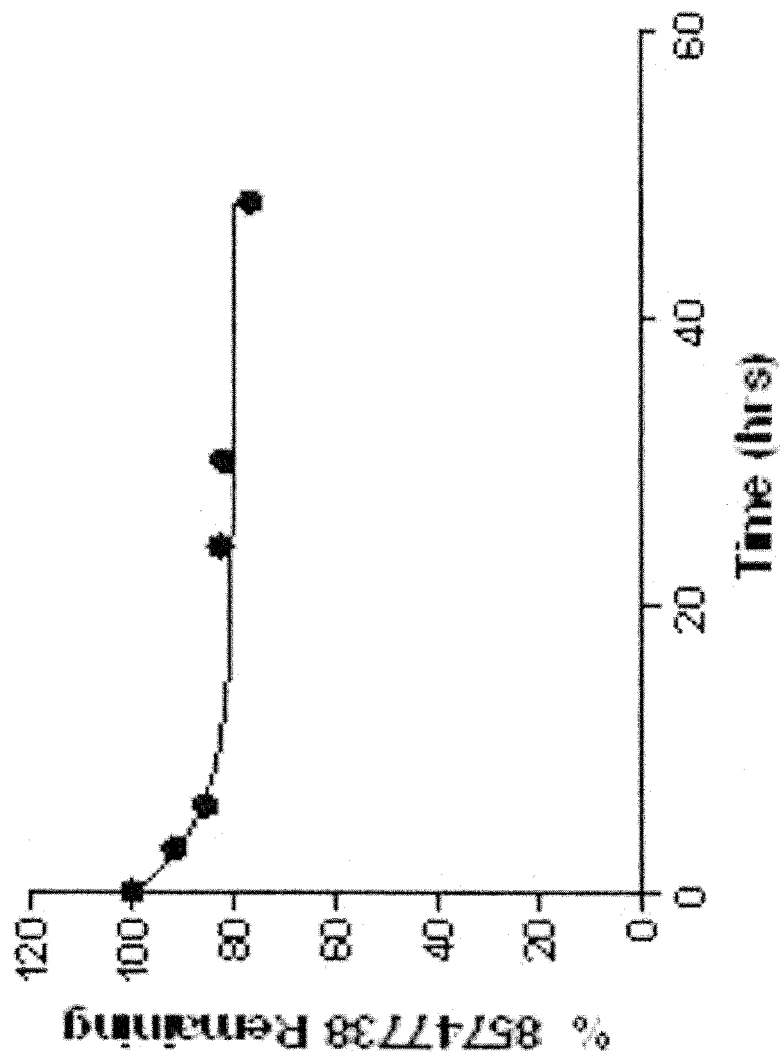
FIG. 23: Shows a graph depicting stability of ML282 or CID1067700 after 48 h in PBS (no additives).

D. Stability:

Stability was measured under two distinct conditions with CID1067700 (FIG. 23). Stability, depicted as closed circles in the graph, was assessed at room temperature (23° C.) in PBS (no antioxidants or other protectants and DMSO concentration below 0.1%). Stability data is depicted as a graph showing the loss of compound with time over a 48 hr period with a minimum of 6 time points and providing the percent remaining compound at end of the 48 hr period [39, 41]. Under these conditions, 77% of CID1067700 remains after 48 hours. It is unknown at this time if or what degradation might be occurring or what this result truly represents.

To assess the chemical stability of CID1067700 and its propensity towards nucleophilic attack, the compound was treated with a range of equivalents of L-glutathione in DMSO for 72 h at 37° C. The three experiments were monitored by LCMS at each of the following time points: 1 h, 2 h, 4 h, 24 h, 48 h, and 72 h. Procedure: To a solution of CID1067700 (2-(3-benzoylthioureido)-5,5-dimethyl-5,7-dihydro-4H-thieno[2,3-c]pyran-3-carboxylic acid, SID 85747738), 1.0 mg, 2.56 μmol, 1 eq) in DMSO (1.0 mL) was added:

a) L-glutathione (1.0 mg, 3.25 μmol, 1.2 eq) and the mixture stirred at 37° C. for 72 h b) L-glutathione (1.6 mg, 5.12 μmol, 2.0 eq) and the mixture stirred at 37° C. for 72 h c) L-glutathione (2.4 mg, 7.68 μmol, 3.0 eq) and the mixture stirred at 37° C. for 72 h LCMS analysis of each reaction vial, taken after time (t)=1 h, 2 h, 4 h, 24 h, 48 h, and 72 h, showed only the presence of 2-(3-benzoylthioureido)-5,5-dimethyl-5,7-dihydro-4H-thieno[2,3-c]pyran-3-carboxylic acid (SID 85747738). No glutathione conjugate or other peaks were observed. These results suggest that the compound is not generally electrophilic or susceptible to protein-derived nucleophiles Submission of Five Related Analogues to the MLSMR:

Five analogues were selected for a more thorough comparison to and support of probe ML282 (FIG. 24). These compounds have been fully characterized, submitted to the MLSMR and MLS numbers are pending. The structures of five selected analogs and solubility data for select compounds are summarized in Table 2, below.

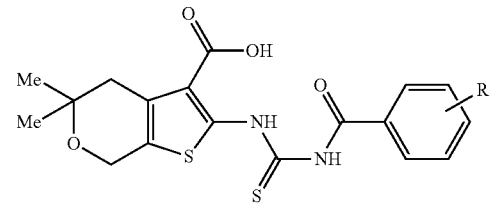

TABLE 2

MLSMR analogss and solubility data collected for select compounds

| | | | Aqueous Assay Conditions | | | |
|---|---|---|---|---|---|---|
| Entry | PubChem ID | R | 1 × PBS, pH 7.4 | Dose Response-EDTA buffer: 30 mM HEPES, pH 7.5, 100 mM KCl, 20 mM NaCl, 0.01% (v/v) NP-40, 1 mM EDTA | Dose Response-Mg buffer: 30 mM HEPES, pH 7.5, 100 mM KCl, 20 mM NaCl, 0.01% (v/v) NP-40, 1 mM MgCl2 | LDV-FITC assay buffer: RPMI 1640 + 10% HI-FBS | EGFR degradation assay medium: DMEM/F-12, Invitrogen #11320-082 |
| 1 | SID125299368 CID53377405 | 4-F | 85.7 μg/mL, 209.8 μM | 98.2 μg/mL, 240.4 μM | 69.1 μg/mL, 169.2 μM | 115.3 μg/mL, 282.3 μM | 67.6 μg/mL, 165.5 μM |
| 2 | SID124756603 CID53301931 | 2-Br | >93 μg/mL, >198 μM | >93 μg/mL, >198 μM | >93 μg/mL, >198 μM | >93 μg/mL, >198 μM | >93 μg/mL, >198 μM |
| 3 | SID124756597 CID53301934 | 3-MeO | 36.5 μg/mL, 86.8 μM | 33.8 μg/mL, 80.4 μM | 29.7 μg/mL, 70.6 μM | >83 μg/mL, >197.4 μM | 54.5 μg/mL, 129.6 μM |

TABLE 2-continued

MLSMR analogss and solubility data collected for select compounds

| | | | | Aqueous Assay Conditions | | | |
|---|---|---|---|---|---|---|---|
| Entry | PubChem ID | R | 1 × PBS, pH 7.4 | Dose Response-EDTA buffer: 30 mM HEPES, pH 7.5, 100 mM KCl, 20 mM NaCl, 0.01% (v/v) NP-40, 1 mM EDTA | Dose Response-Mg buffer: 30 mM HEPES, pH 7.5, 100 mM KCl, 20 mM NaCl, 0.01% (v/v) NP-40, 1 mM MgCl$_2$ | LDV-FITC assay buffer: RPMI 1640 + 10% HI-FBS) | EGFR degradation assay medium: DMEM/F-12, Invitrogen #11320-082) |
| 4 | SID12456604 CID53301935 | 2-F | NT | NT | NT | NT | NT |
| 5 | SID124756598 CID53301932 | 4-MeO | NT | NT | NT | NT | NT |

NT = not tested

Probe and Analog Preparation
General Experimental and Analytical Details:

$^1$H and $^{13}$C NMR spectra were recorded on a Bruker AM 400 spectrometer (operating at 400 and 101 MHz respectively) or a Bruker AVIII spectrometer (operating at 500 and 126 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis (1H,1H,3H-tetrafluoropropoxy) phosphazine; and a make-up solvent of 90:10:0.1 MeOH:Water:Formic Acid which was introduced to the LC flow prior to the source to assist ionization. Melting points were determined on a Stanford Research Systems OptiMelt apparatus.

Results

High throughput screening of the MLSMR identified CID1067700 as a compound that inhibits fluorescent guanine nucleotide binding to all of the small GTPases tested which included representatives of Rho, Ras and Rab subfamilies. The compound was titrated in the presence of fluorescent GTP and the EC$_{50}$ values for the panel were determined to be in the nanomolar potency range. The biochemical binding assay was performed in a multiplex format with multiple purified GST-GTPases tested simultaneously. Integrin VLA4 binding towards its receptors is known to be activated by Rho GTPases. This interaction was found to be inhibited by CID1067700. EGFR degradation in response to growth factor stimulation was used to assess cellular inhibition of Rab-regulated pathways. CID1067700 inhibited EGFR degradation in two independent cell lines. Thus, CID1067700 is capable of inhibiting both Rho and Rab subfamily GTPases in cells. SAR was also conducted to characterize the molecular features that are important for the CID1067700 activity.

Scaffold/Moiety Chemical Liabilities

Aqueous PBS and media solubility was for CID1067700 and several analogs was determined to be excellent. The thienylpyran-benzoylthiourea scaffold and its derivatives have been easily handled in terms of stability to reaction conditions, exposure to acid or base, heating, and general manipulation. We have not observed decomposition under these conditions nor have we experienced any chemical liability with these compounds. Most compounds were obtained as stable solid materials. The CID1067700 structure does not contain moieties that are known generally to be reactive. As discussed above, aqueous stability of CID1067700 revealed that after 48 h, only 77% of parent compound remained. It is unknown at this time what degradation might be occurring or what this result truly represents. As it was also shown, treatment of CID1067700 with excess glutathione for 72 h at 37° C. did not result in LCMS detection of any conjugates or other product peaks; only the unchanged parent CID1067700 was detected. These results suggest that the compound is not generally electrophilic or susceptible to protein-derived nucleophiles. The team recommends generally that CID1067700 be prepared for dilution prior to use in any assay, as opposed to doing so days in advance.

SAR Tables

The HTS effort produced a single hit that demonstrated potent Rab7 potency and was suitable for chemical manipulation and SAR exploration. The potency for the thienylpyran hit of interest (CID1067700, 2 batches were used: SIDs 57578339 and 85747738, FIG. 4) showed inhibition for each of the tested GTPases in the panel with potencies for each summarized in the table set forth in FIG. 34. While the hit met the defined probe criteria, the team set out to determine if the hit scaffold had tractable SAR and if any selectivity could be developed through the generation of supporting analogs. For this effort, 39 compounds were tested (31 synthesized, 8 purchased), and all analogs were purified and analyzed for structural integrity and purity prior to assay. The SAR strategy focused on five regions of the scaffold (shaded areas, FIG. 24).

Data from the primary assay using EDTA were used to drive the SAR, except for Rac and Rho GTPases which could not be assessed under these conditions. These targets, Rab7 and Cdc42, were also assayed using magnesium, and that data are tabulated for comparison in this section. The parent hit compound, submitted as two separate batches, was found to potently inhibit each of the GTPases in the panel. The separate batches of the hit and the associated data are listed individually (Table 4, entries 1-2), along with averaged values (entry 3). Generally, for active compounds, the percent response for Rab7 was greater than that for other GTPases.

Some of the first structural modifications that were investigated involved modification of the pyran ring. Reducing the steric bulk at the gem dimethyl position, effected by removal of one or both of the methyl groups (entries 4 and 5, respectively), was tolerated without much change in potency or selectivity. Likewise, exchange for one methyl group for ethyl or installation of a spiro-cyclopentane ring (entries 6 and 7, respectively) afforded analogs with profiles analogous to the hit activity. Exchange of the gem dimethyl groups for a t-butyl group resulted in a decline in potency, particularly for Rab7 (entry 8). Lastly, replacement of the pyran oxygen atom with a methylene unit (entry 9, X=O→CH$_2$) did not appreciably alter the activity profile from that of the hit. These changes indicated that the pyran ring is relatively flexible in terms of substitution and alteration without attenuating potency; however, these measured modifications also did not affect selectivity.

Figure 25:
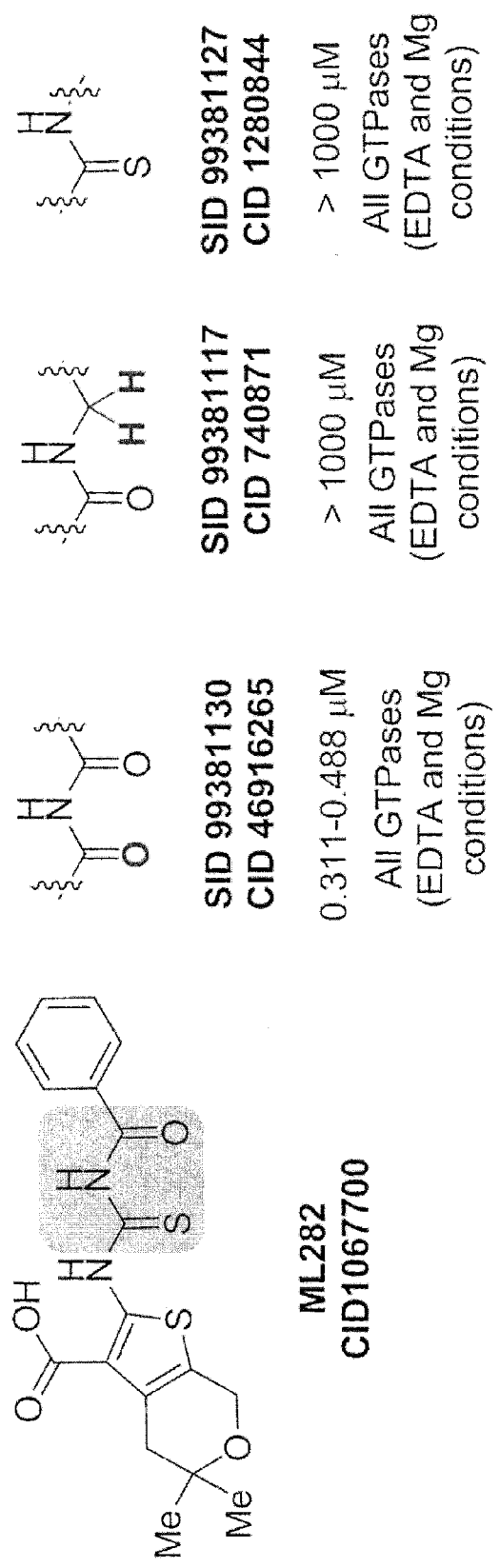
FIG. 25: Shows the effect of modifying the thiourea-carbonyl linker (shaded area) on potency.

Some focus was shifted to the importance of the carboxylic acid moiety. Esterification of this functionality resulted in loss of activity for all GTPases tested; thereby, indicating it was essential for retaining potency (data not shown). Isosteres or other replacements were not pursued due to synthetic challenges; however, this may be a possibility in future work. Alterations of the thiourea-carbonyl linker were also briefly studied (FIG. 25). Replacement of the sulfur atom with an oxygen atom (SID 99381130) led to an average 7-fold loss in potency across all GTPases. Replacement of the carbonyl with a methylene unit (SID 9938117) or alternatively, removal of the carbonyl (SID 99381127), thus shortening the linker, led to inactive analogs for all GTPases.

Most structural variations resulted from phenyl moiety substitutions (Table 4). Generally, of the 2- or 3- or 4-substituted phenyl rings that were tested, 2-substituted phenyl rings were the least active. Regardless of the electronics of the substituent installed on the ring, none were more beneficial than the parent structure which possessed an unsubstituted phenyl ring. Replacement of the phenyl ring with other heterocycles such as 2-furyl or 2-thiophene (entries 16 and 17) gave analogs with profiles analogous to the parent hit. The 2-thiophene analog possessed a slightly better potency profile across all GTPases tested, and no changes in selectivity were noted. A non-aromatic cyclohexyl substituent was also surveyed (entry 18) without benefit.

Probe Selection The structural modifications described in this section delivered several analogs with potency near that of the hit and demonstrated that there are critical features of the scaffold that are necessary for retaining potency. As many analogs had a similar profile to the hit and much more biology had been explored with this compound, the team decided to select the hit, CID1067700, as the probe, ML282.

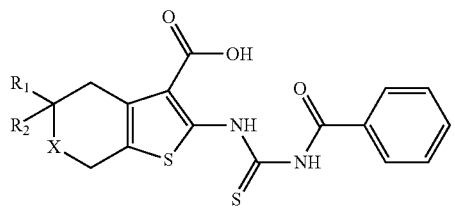

General structure for Table 3

TABLE 3

SAR data for modification of the pyran moiety of CID1067700

| | | FIG. 7 | | | Assay | GTS-tagged Rab7 GTPase Assay Potency (µM) mean (n = # replicates) | | |
|---|---|---|---|---|---|---|---|---|
| Entry | PubChem ID | X | $R_1$ | $R_2$ | P or S | Format | n | $EC_{50}$ µM | % Res |
| 1 | SID 57578339 CID1067700 | O | Me | Me | P | EDTA Mg | 1 0 | 0.084 ND | 92 |
| 2 | SID85747738 CID1067700 | O | Me | Me | P | EDTA Mg | 1 1 | 0.022 0.038 | 58 43 |
| 3 | SID57578339 SID85747738 CID1067700 | O | Me | Me | P | EDTA Mg | 2 1 | 0.053 0.038 | 75 43 |
| 4 | SID99381128 CID46916263 | O | Me | H | S | EDTA Mg | 2 1 | 0.14 ± 0.11 0.192 | 91 ± 4 56 |
| 5 | SID99381129 SID125299359 CID46916266 | O | H | H | S | EDTA Mg | 3 2 | 0.11 ± 0.13 0.24 | 91 ± 12 45 ± 2 |
| 6 | SID125299362 CID53377401 | O | Me | Et | S | EDTA Mg | 1 1 | 0.037 0.035 | 109 43 |
| 7 | SID125299361 CID53377403 | O | -(CH$_2$)$_4$- | | S | EDTA Mg | 1 1 | 0.035 0.033 | 72 56 |
| 8 | SID125299360 CID53377399 | O | H | t-butyl | S | EDTA Mg | 1 1 | 0.47 0.22 | 18 47 |
| 9 | SID124756600 CID53301937 | CH$_2$ | Me | Me | S | EDTA Mg | 3 2 | 0.066 ± 0.02 0.063 ± 0.01 | 97 ± 5 53 ± 1 |

P = purchased;
S = synthesized;
ND = not determined

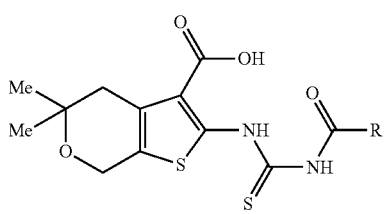

Structure for Table 4, below.

Cellular Activity

ML282 (CID106770) has No Obvious Cellular Toxicity.

The most useful molecular probes have a generous "therapeutic" window in which they do not demonstrate cellular toxicity. As a model cell line used in biomedical research, U937 cells mature and differentiate in response to a number of soluble stimuli [44]. Also, a mutant form of U937 cells was used in the cellular VLA4 binding assay. Therefore, the cytotoxicity of ML282 (CID106770) and its analogues were evaluated in the U937 cells. The compound was included in the growth medium of U937 cells for 24 h. The cell density and viability were subsequently measured. The cells had a

TABLE 4

Summary of SAR data for modification of the phenyl ring of the hit scaffold, CID1067700

| | | FIG. 9 | | Assay | GTS-tagged Rab7 GTPase Assay Potency (μM) mean (n = # replicates) | | |
|---|---|---|---|---|---|---|---|
| Entry | PubChem ID | R | P or S | Format | N | $EC_{50}$ μM | % Res |
| 1 | SID57578339 | phenyl | P | EDTA | 1 | 0.084 | 92 |
| | CID1067700 | | | Mg | 0 | ND | |
| 2 | SID85747738 | phenyl | P | EDTA | 1 | 0.022 | 58 |
| | CID1067700 | | | Mg | 1 | 0.038 | 43 |
| 3 | SID57578339 SID85747738 | phenyl | P | EDTA | 2 | 0.053 | 75 |
| | CID1067700 | | | Mg | 1 | 0.038 | 43 |
| 4 | SID125299370 | 2-MeO-phenyl | S | EDTA | 1 | 1.12 | 52 |
| | CID53377397 | | | Mg | 0 | ND | |
| 5 | SID124756597 | 3-MeO-phenyl | S | EDTA | 3 | 0.15 ± 0.13 | 68 ± 25 |
| | CID53301934 | | | Mg | 1 | 0.32 | 37 |
| 6 | SID124756598 | 4-MeO-phenyl | S | EDTA | 3 | 0.14 ± 0.07 | 94 ± 14 |
| | CID53301932 | | | Mg | 2 | 0.14 ± 0.11 | 54 ± 2 |
| 7 | SID124756604 | 2-F-phenyl | S | EDTA | 3 | 0.14 ± 0.16 | 97 ± 15 |
| | CID53301935 | | | Mg | 2 | 0.17 ± 0.21 | 45 ± 2 |
| 8 | SID124756599 | 3-F-phenyl | S | EDTA | 3 | 0.32 ± 0.09 | 90 ± 6 |
| | CID53301930 | | | Mg | 2 | 0.29 ± 0.19 | 39 ± 3 |
| 9 | SID125299368 | 4-F-phenyl | S | EDTA | 1 | 0.095 | 100 |
| | CID53377405 | | | Mg | 1 | 0.077 | 39 |
| 10 | SID124756603 | 2-Br-phenyl | S | EDTA | 3 | 0.43 ± 0.68 | 86 ± 10 |
| | CID53301931 | | | Mg | 2 | 0.65 ± 0.87 | 35 ± 4 |
| 11 | SID124756601 | 3-Br-phenyl | S | EDTA | 2 | 2.51 ± 2.1 | 41 ± 0 |
| | CID53301936 | | | Mg | 1 | >100 | NA |
| 12 | SID124756602 | 4-Br-phenyl | S | EDTA | 3 | 0.30 ± 0.18 | 93 ± 6 |
| | CID53301933 | | | Mg | 2 | 0.27 ± 0.22 | 41 ± 6 |
| 13 | SID125299363 | 2-Me-phenyl | S | EDTA | 1 | 0.41 | 95 |
| | CID53377404 | | | Mg | 1 | 0.52 | 47 |
| 14 | SID125299364 | 3-Me-phenyl | S | EDTA | 1 | 1.16 | 93 |
| | CID53377400 | | | Mg | 1 | 0.36 | 30 |
| 15 | SID125299365 | 4-Me-phenyl | S | EDTA | 1 | 0.14 | 102 |
| | CID53377395 | | | Mg | 1 | 0.097 | 40 |
| 16 | SID125299366 | 2-furyl | S | EDTA | 1 | 0.074 | 105 |
| | CID53377402 | | | Mg | 1 | 0.082 | 63 |
| 17 | SID125299367 | 2-thiophene | S | EDTA | 1 | 0.025 | 103 |
| | CID53377398 | | | Mg | 1 | 0.025 | 56 |
| 18 | SID125299369 | cyclohexyl | S | EDTA | 1 | 0.81 | 89 |
| | CID53377396 | | | Mg | 1 | 0.46 | 39 |

P = purchased;
S = synthesized;
ND = not determined;
NA = not applicable growth rate comparable to that treated with the DMSO control and maintained their viability (Table 5). Thus, ML282 (CID106770) and its analogues demonstrate no obvious cytotoxicity and supports their use in cellular assays.

TABLE 5

Cell viability of U937 cells after treatment with analogs[a]

| DMSO | CID1067700 | CID1280844 | CID46916263 | CID46916266 |
|---|---|---|---|---|
| (control) 94% | 94% | ND | 94% (100 µM) | 92% (100 µM) |
| CID46916265 | CID53301934 | CID53301932 | CID53301930 | CID53301937 |
| 98% (100 µM) | 94% | 96% | 92% | 91% |
| CID53301936 | CID53301933 | CID53301931 | CID53301935 | CID53377399 |
| ND | 93% | 94% | 96% | ND |
| CID53377403 | CID53377401 | CID53377404 | CID53377400 | CID53377395 |
| ND | ND | ND | ND | ND |
| CID53377402 | CID53377398 | CID53377405 | CID53377396 | CID53377397 |
| ND | ND | 94% | ND | ND |

[a]Experiment done for 24 h at a concentration of 20 µM unless indicated otherwise
ND = not determined Results
Identification of a Small Molecule (CID1067700) as an Inhibitor of Nucleotide Binding by Ras-Related GTPases CID1067700 was identified as an inhibitor of GTP-binding using a high throughput screen that we described previously in the context of an allosteric Rho GTPase inhibitor (35). Briefly, six sets of beads (each with a unique red fluorescence intensity) were individually coated with six representative GST-tagged Ras-related GTPases (Cdc42 wt, Rac1wt, Rac1Q61L, Rab2 wt, Rab7 wt, and H-Ras wt) (FIG. 29A). The individually conjugated beads were then assayed in the presence of individual compounds in the Molecular Libraries Small Molecule Repository using a HyperCyt flow cytometry to identify molecules that altered the binding of fluorescent nucleotide to Ras-family GTPases (36). CID1067700 (FIG. 29B) was identified as a hit that decreased fluorescent nucleotide (GTP) binding in the primary screen and was confirmed in secondary, multiplex dose response assays to have an $EC_{50}$ of 20-500 nM and at least 40% inhibition against all tested GTPases (FIG. 29C). CID1067700 was the only compound identified in the screen to have significant inhibitory activity against the Rab GTPases (Rab2 and Rab7). Because of its pronounced inhibitory effect on BODIPY-nucleotide binding (>90%) to Rab7 (FIG. 29D), analogous to unlabeled nucleotides (FIG. 29E), and the absence of any known chemical inhibitors for Rab-family GTPases, we further characterized the mechanism of CID1067700 inhibition using Rab7 as a model protein.

Dose Dependent Inhibition of Rab7 Nucleotide Binding by CID1067700

Single-plex dose response measurements were used to determine the inhibitory efficacy and potency of CID1067700 on nucleotide binding by Rab7. This allowed the GDP and GTP concentrations in the assay to be fixed to the previously determined equilibrium dissociation constants ($K_d$=100 nM BODIPY-GTP; $K_d$=40 nM BODIPY-GDP) for the wild-type (wt) Rab7 protein (33). Increasing CID1067700 concentrations resulted in strong inhibition of both BODIPY-GDP- and BODIPY-GTP-binding by Rab7 wt with $EC_{50}$ values of 25 nM for BODIPY-GTP and 40 nM for BODIPY-GDP (FIG. 28d). The efficacy of inhibition was 40% for BODIPY-GDP and 80% for BODIPY-GTP. These results demonstrate high efficacy and potency of the CID1067700 molecule with respect to inhibition of Rab7 nucleotide binding. Maximum inhibition by CID1067700 occurred at 1-10 µM concentration range. Lower inhibitory efficacy against BODIPY-GDP binding may either represent a preference for one nucleotide conformer over another or the known higher affinity of Rab7 for GDP than for GTP (33, 37).

Inhibition of Rab7 wt nucleotide binding by CID1067700 could be effected through allosteric or competitive binding. To distinguish between the two scenarios, we tested the inhibition of Rab7 wt by CID1067700 under conditions where CID1067700 concentration was held at a fixed concentration (100-200 nM) while increasing the concentration of the fluorescent nucleotide competitor (FIG. 30a-h). These values were equivalent to approximately 5 times the observed $EC_{50}$ for CID1067700 using each of the two nucleotides. The inhibitory effect of CID1067700 was most pronounced at lower nucleotide concentrations, resulting in an overall rightward shift of the dose response curves (FIG. 30b, d). Significantly, both control (DMSO only) and inhibitor (CID1067700 treated) curves had statistically similar $B_{max}$ values that correspond to the number of binding sites on Rab7 (FIG. 30a, c). Thus, at high concentrations, the nucleotide out competes the CID1067700 compound for the binding pocket, accounting for the $B_{max}$ values that are not statistically different. On the contrary, there was ≤3-fold increase in the observed $EC_{50}$ for both nucleotides in the presence of CID1067700 indicating competition of nucleotides by the inhibitor. Inhibitor constants ($K_i$) calculated using Cheng Prusoff equation (38) show a 2-fold increase between inhibition of BODIPY-GTP and BODIPY-GDP confirming that CID1067700 is better at inhibiting BODIPY-GTP binding than BODIPY-GDP binding (Supplemental Table 51). Analysis of the constitutively active Rab7Q67L and dominant negative Rab7T22N mutants, that mimic the GTP-bound and GDP-bound conformers respectively showed that both were similarly inhibited by CID1067700 (FIG. 30e-h). The composite data suggest that the CID1067700 compound and the nucleotide most likely compete for the nucleotide binding pocket of Rab7.

CID1067700 does not Affect Nucleotide Release by Rab7

To further confirm the mode of Rab7 nucleotide inhibition by CID1067700, we analyzed the fluorescent nucleotide dissociations rates from Rab7 in the presence of CID1067700. The experiment was carried out by pre-binding BODIPY-GTP or BODIPY-GDP to GST-tagged Rab7 protein to equilibrium and then assaying for the loss of fluorescence over time occasioned by the release of bound nucleotide (FIG. 31A-D). As a competitor, we used CID1067700 (10 µM) or unlabeled GDP (10 µM). Dissociation rate constants were calculated from data fit to exponential functions using Prism software. $K_{off}$ values of Rab7 wt obtained at room temperature were statistically similar between unlabeled GDP and CID1067700 competitor for both BODIPY-GTP or BODIPY-GDP. Together the data confirm that the CID1067700 compound has no effect on the rate of release of bound fBODIPY-GTP or BODIPY-GDP by Rab7, ruling out allosteric binding of the CID1067700 inhibitor in preference to competitive binding to the nucleotide pocket.

Figure 32A:
FIGS. 32A-H: Shows that CID1067700 docks optimally in the nucleotide binding pocket of Rab7 in the GTP-bound conformation. (A-D) CID1067700 docked in the nucleotide binding site of Rab7 in the (GTP)-bound (PDB 1VG8) and GDP-bound (PDB 1VG9) conformations. Molecular docking carried out using Fred docking software. Both GTP or GDP and CID1067700 are shown simultaneously docked in the pocket for purposes of comparing their orientations in the pocket. (E-H) Interaction maps for Rab7-GTP vs. CID1067700 and Rab7-GDP vs. CID1067700 illustrate differences in number and sites of interaction.
Figure 32B:
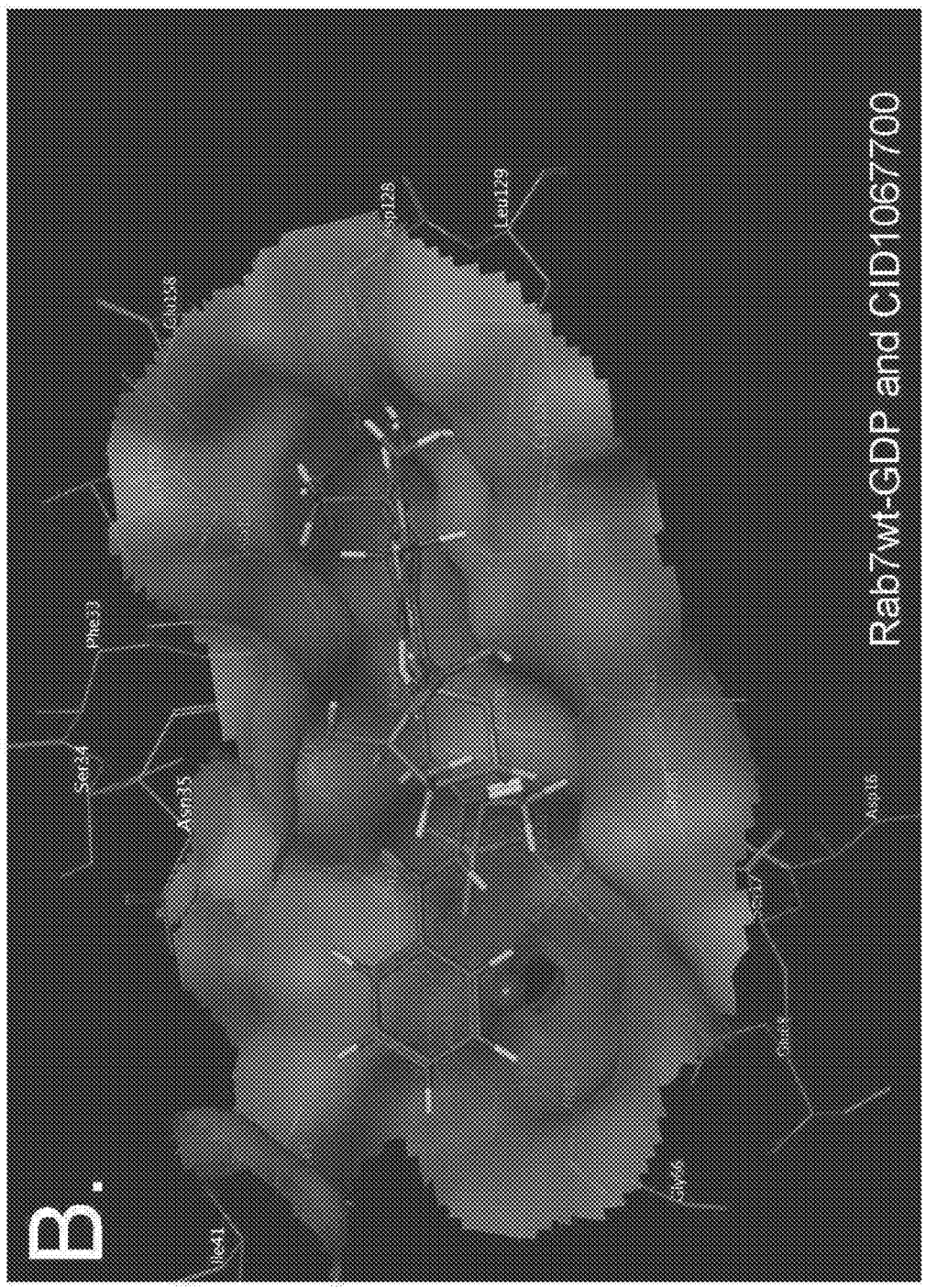
Figure 32C:
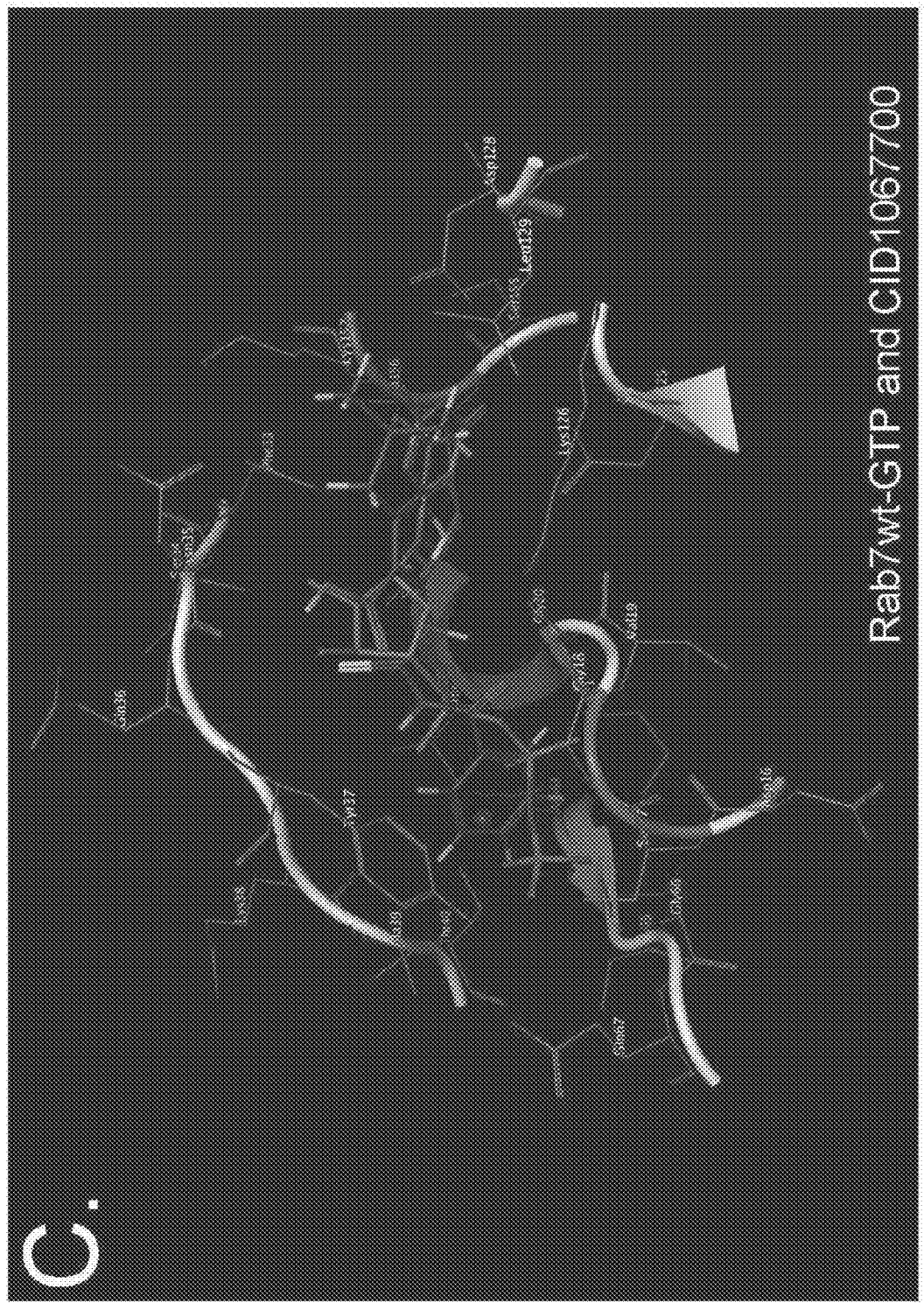
Figure 32D:
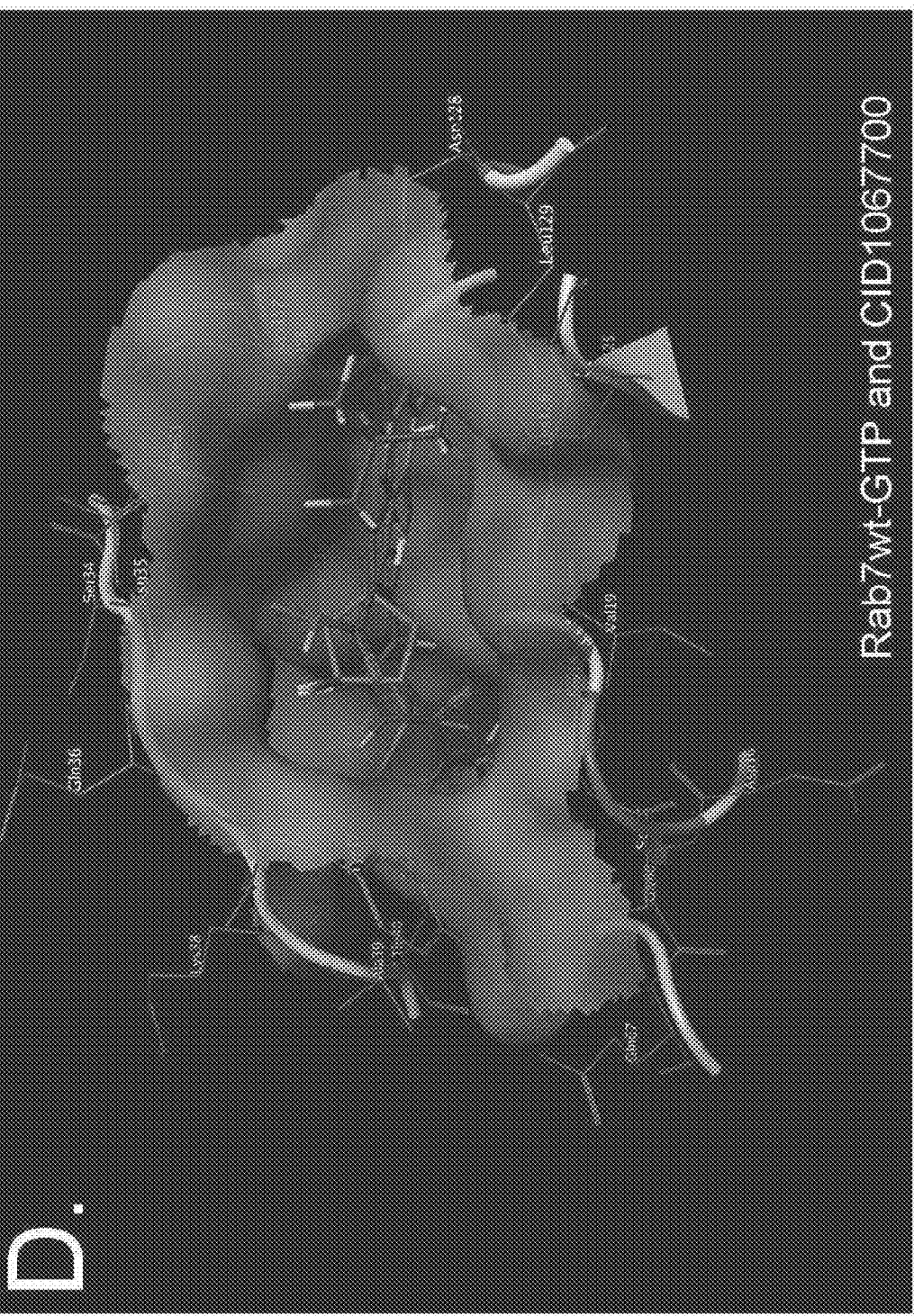
Figure 32E:
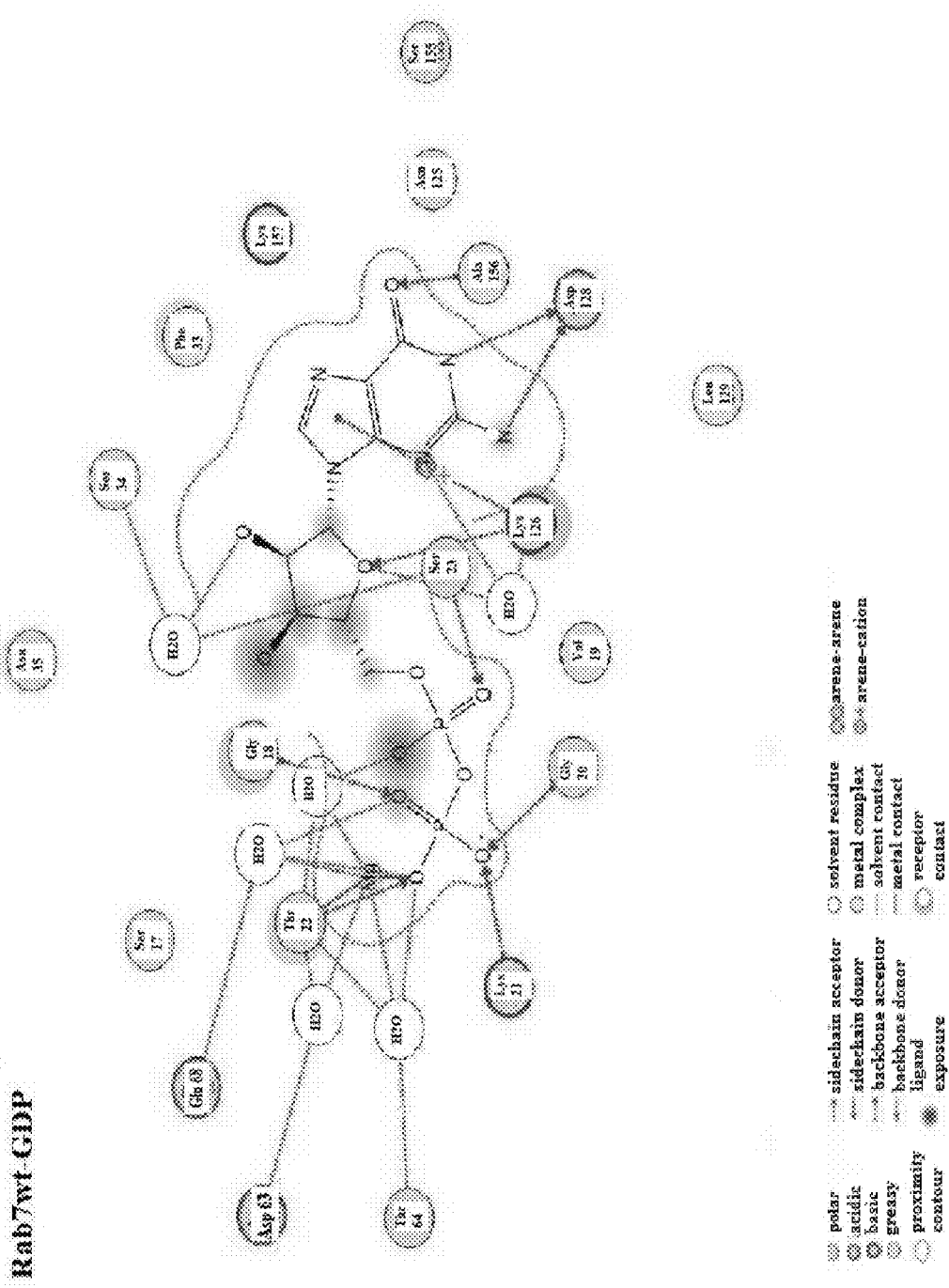
Figure 32F:
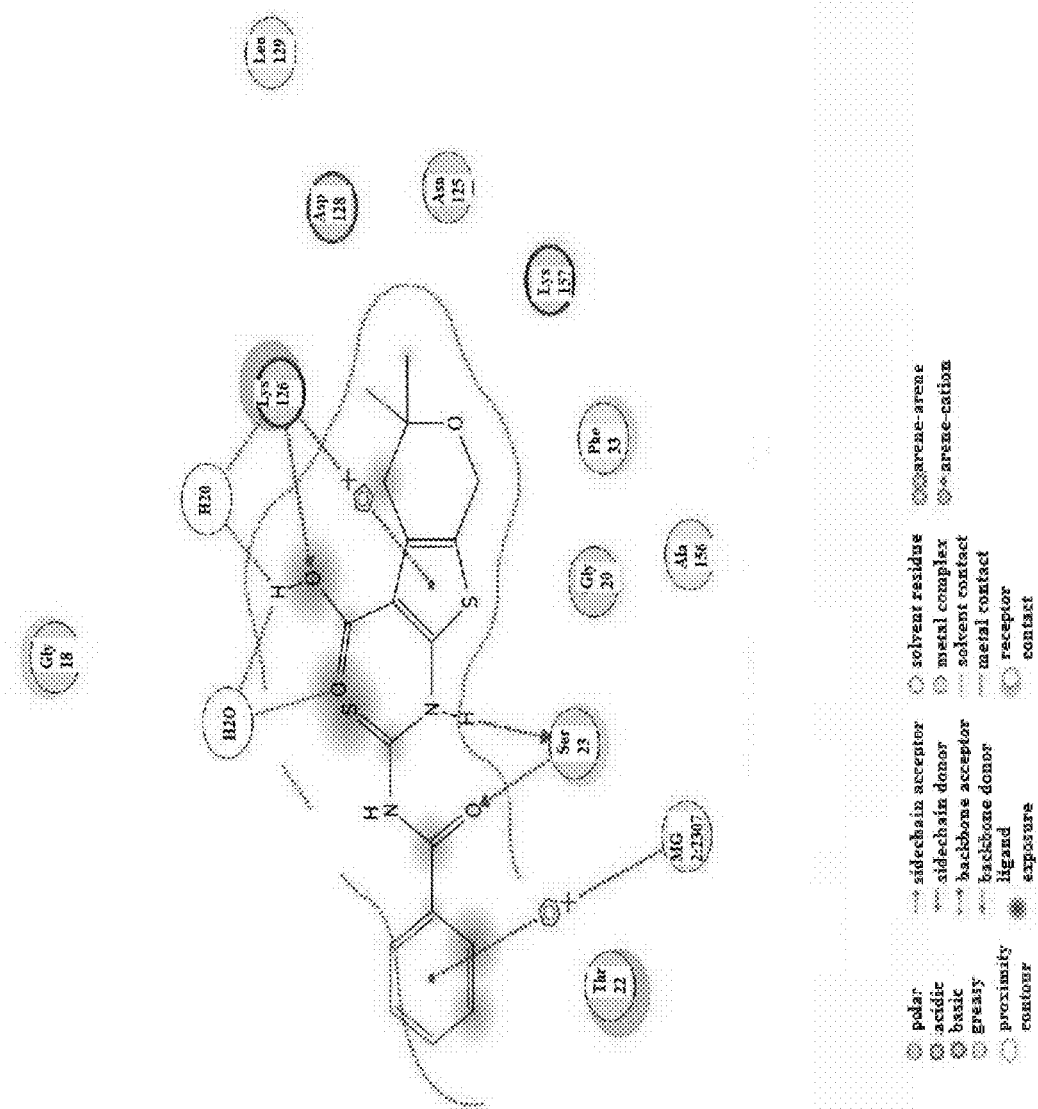
Figure 32G:
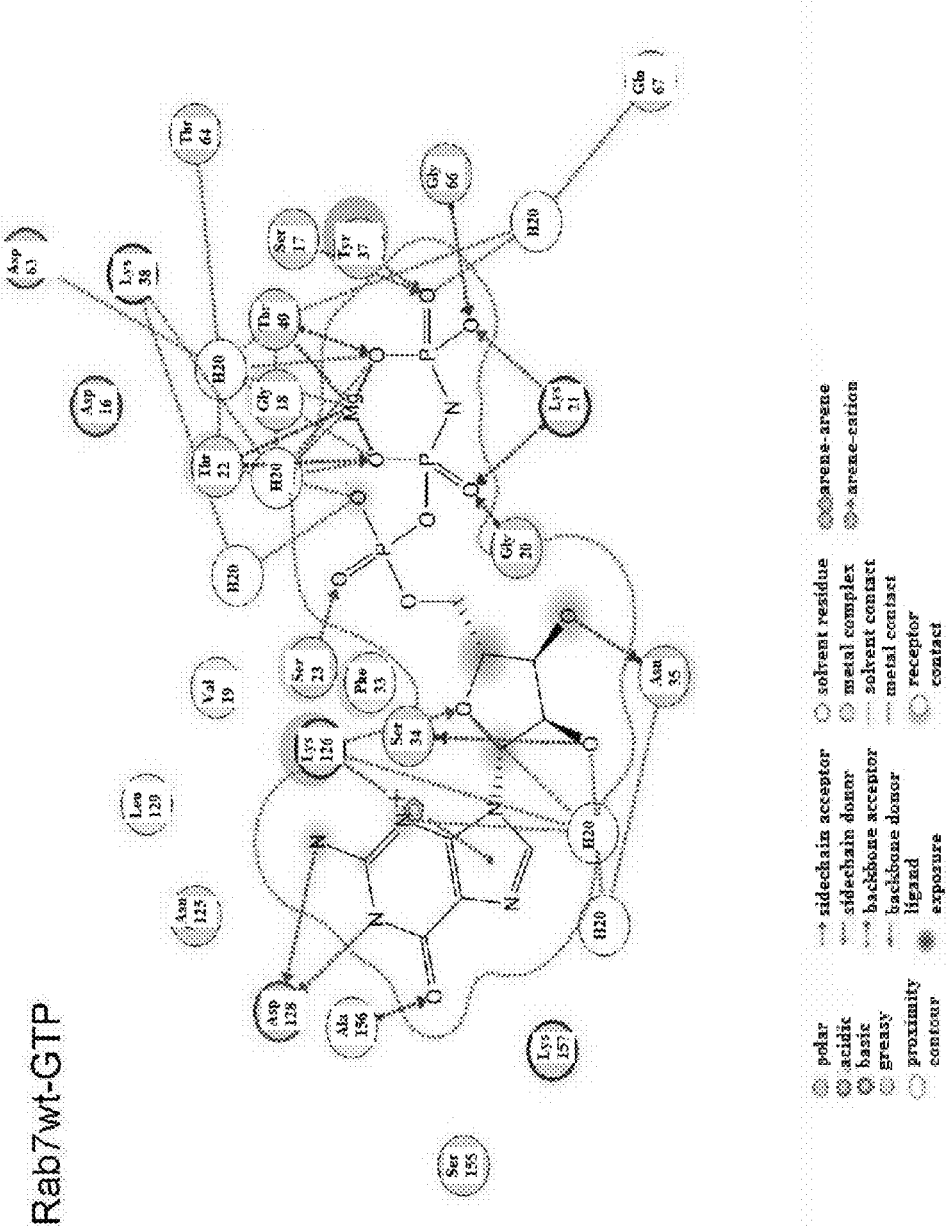
Figure 32H:
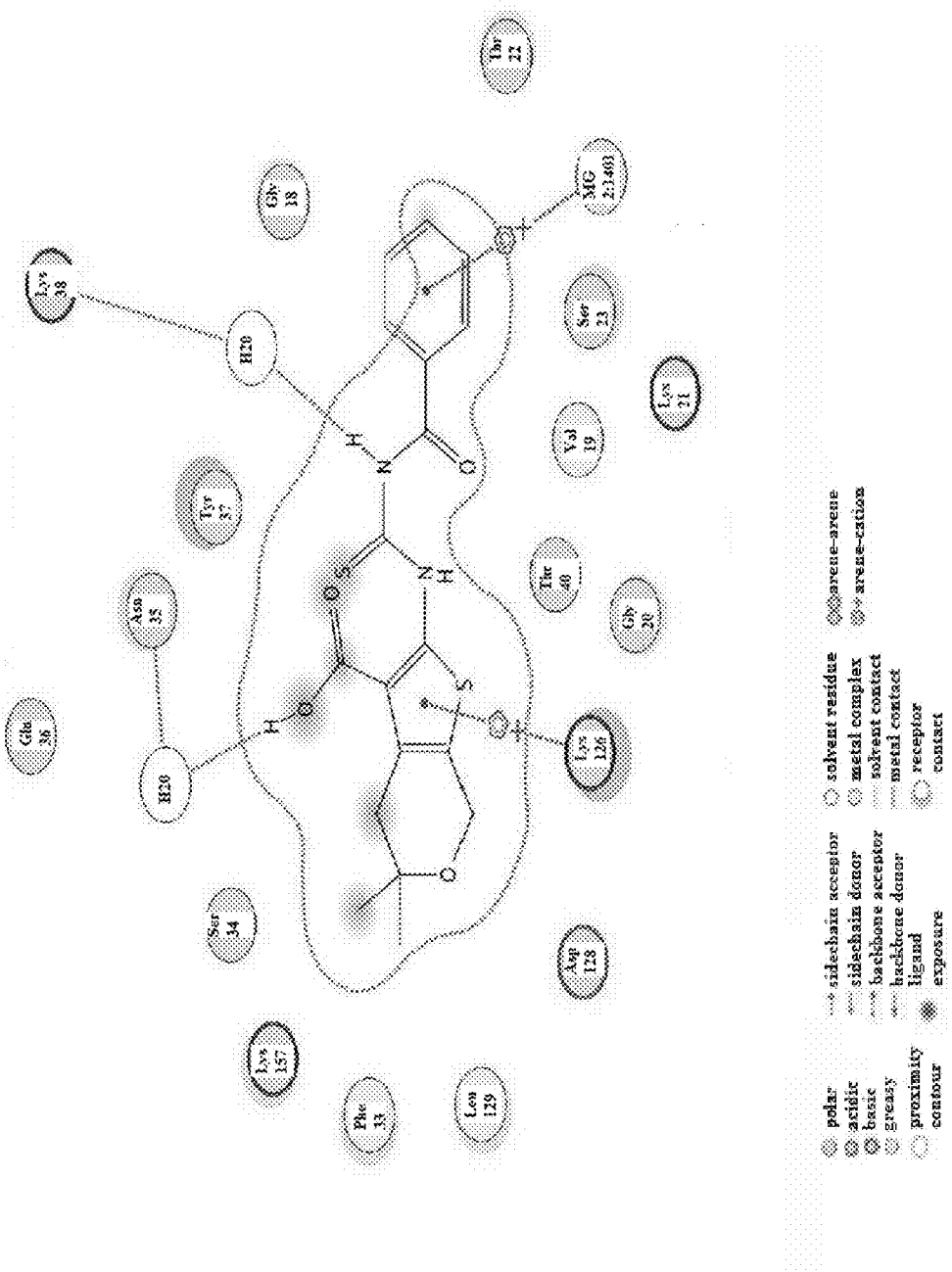

Molecular Docking of CID1067700 on Rab7 Wt GDP and GTP Bound Crystal Structures Shows Optimal Binding to the Nucleotide Binding Pocket of the GTP-Conformer The molecular docking of CID1067700 in the nucleotide binding site of Rab7 as predicted by the experimental data was examined using molecular docking OpenEye Fred docking software (FIG. 32a-h). Docking of CID1067700 on the GDP- and GTP-conformers revealed that the molecule fills the nucleotide binding pocket of both conformers in a manner that mimics the nucleotides (FIG. 32a-d). However, the interaction map revealed that the compound had fewer potential interactions with the GDP-conformer where the binding pocket is more exposed to solvent, which may also explain why BODIPY-GDP outcompetes CID1067700 better than the BODIPY-GTP (FIG. 32e-f). The good alignment between CID1067700 with GNP where 5,7-dihydro-4H-thieno[2,3-c] pyran ring system has the same orientation as guanine ring system could suggest the binding mode of the small molecule in the nucleotide binding pocket. To confirm the most likely binding mode however, a crystal structure determination study involving both CID1067700 and Rab7 will be required.

Structure Activity Analyses Identify Critical Determinants for Competitive Inhibition To determine structure activity relationships (SAR), eighteen variants of the parent compound were evaluated. This preliminary SAR set was obtained through synthetic effort (11 compounds) or commercial acquisition (7 compounds). The parent scaffold, represented by CID1067700, was modified in any of three major regions to afford the initial analog collection. The structural alterations focused on esterification of the carboxylic acid ($R_1$), geminal substitution changes on the fused pyran ring ($R_2$, $R_3$), mutation of the ring-fused pyran to an N-methylated ring-fused piperidine, or revision of the N-acyl thiourea linker (L). Only three of the compounds retained activity in a multiplex GTPase screen with all other derivatives being inactive (FIG. 33). The parent, three active derivatives and one inactive derivative were assayed in single-plex dose response assays and $EC_{50}$ determined against Rab7 (FIG. 33a-e). Esterification of the carboxylic acid moiety resulted in loss of inhibition, a finding that supports the suggested participation of this group in hydrogen bonding (FIG. 32). Removal of one or both of the gem-dimethyl groups from the parental thiophenylpyran structure ($R_2$-$R_3$) resulted in a 10- or 20-fold loss in potency respectively when compared across multiple GTPases (FIG. 34). The effect on potency observed with the gem dimethyl substitution suggests an advantageous lipophilic ligand-binding site interaction that is lost upon substituent removal. Alteration of the N-acyl thiourea linker further attenuated potency, as demonstrated by the 35-fold loss in potency observed with N-acyl urea CID46916265 (FIGS. 33d and 34), and the complete loss of activity for thiourea CID1251121 (FIGS. 33e and 34) and amide CID740871 (FIGS. 33 and 34). These results indicate that the orientation of tethered groups, and the length and hydrogen-bonding character of the linker region are critical to maintaining a beneficial activity profile.

Discussion

In the present study we identify CID1067700 as a small chemical molecule that inhibits nucleotide binding to Rab7 in the nanomolar range with $EC_{50}$ values of 25 nM for GTP and 40 nM for GDP and a calculated efficacy of nucleotide binding inhibition as 40% for BODIPY-GDP and 80% for BODIPY-GTP. Kinetic and equilibrium binding studies demonstrate that the compound acts as a competitive inhibitor and exhibits a good fit to the nucleotide binding pockets of both the GTP- and GDP-bound conformations of Rab7. By assaying on rate kinetics of Rab7 nucleotide binding in the presence of CID1067700, we noted a decrease in the number of available BODIPY-GTP and BODIPY-GDP binding sites on Rab7 across the entire nucleotide concentration range considered (data not shown). Based on equilibrium dissociation measurements, we also showed that CID1067700 does not affect how fast or slow Rab7 releases bound nucleotide and hence confirming that CID1067700 inhibits Rab7 nucleotide binding through a competitive mechanism. Initial structure activity relationships demonstrate a dependence on the lipophilic interactions with the substituted ring-fused pyran, the hydrogen bonding capability of the carboxylic acid, and the integrity of an extended N-acyl thiourea linker to properly extend and orient the tethered aryl functionality. Although our assays focused on characterizing the small molecule on Rab7, CID1067700 also exhibits inhibitory activity on other small GTPases. To the best of our knowledge CID1067700 is the first example of a competitive inhibitor for small GTPases.

CID1067700 was found to inhibit nucleotide binding by both the Rab7Q67L and Rab7T22N mutants that are known to be constitutively in the GTP and GDP bound states, respectively (39). Although the Q67L mutation lies in the nucleotide binding pocket of Rab7, the actual location of the Gln67 residue in the pocket is remote from all predicted contacts with CID1067700. From analysis of the crystal structure Thr22 residue is involved in forming interactions with Mg cofactor which is required for GTP/GDP binding, and although our small molecule inhibitor has a similar binding mode to nucleotides, molecular docking studies suggest that a Mg cofactor may not be essential for its binding. The identification of CID1067700 as a competitive inhibitor of Rab7 nucleotide binding presents an exciting and novel route to characterize Rab family proteins. Most small molecules reported to be active against low molecular GTPases are allosteric inhibitors and have activities that are restricted to the Rho-family GTPases based on their mechanism of action of blocking GEF interactions with Cdc42, Rac1 and RhoA. Thus, the identification of CID1067700 together with our analyses of structure activity relationships suggest that it may be possible with further development to prepare more specific analogs with unique advantages when compared to traditional approaches such as conditional knock out or RNA interference as a means to perturb Rab GTPase functionality. Small molecules can be applied to cells to rapidly and often reversibly inhibit targets. This is exemplified by Brefeldin A, an allosteric inhibitor of Arf GTPases (Vigil, 2010} and inhibitors of phosphoinositide 3-kinases that have been shown to inhibit specific kinase isoforms (40). More over, Rab7 function depends on numerous protein-protein interaction partners including hVps39 (41), TBC1D15 (42), RILP (27, 43), ORPIL (44, 45), Rabring7 (46) and the alpha proteasome subunit XAPC7 (47, 48) whose interaction with Rab7 may be potential candidates for small molecule modulation. Use of small molecule might also be useful for dissecting the order of protein binding to a multimeric complex and/or the importance of nucleotide for stability of the protein complex involving Rab7. Taken together, our findings present CID1067700 as a novel competitive inhibitor of small GTPase nucleotide binding that has potential in vitro for dissecting protein function. It may serve as a springboard for further development of families of compounds selective for individual GTPases.

REFERENCES

First Set of Examples

1. M. P. East, R. A. Kahn, *Semin Cell Dev Biol* (2010).
2. A. K. Gillingham, S. Munro, *Annu Rev Cell Dev Biol* 23, 579 (2007).

3. A. B. Jaffe, A. Hall, *Annu Rev Cell Dev Biol* 21, 247 (2005).
4. S. Mitra, K. W. Cheng, G. B. Mills, *Semin Cell Dev Biol* (2010).
5. M. Parri, P. Chiarugi, *Cell Commun Signal* 8, 23 (2010).
6. M. P. Stein, J. Dong, A. Wandinger-Ness, *Adv Drug Deliv Rev* 55, 1421 (2003).
7. B. J. Grant, A. A. Gorfe, J. A. McCammon, *PLoS Comput Biol* 5, e1000325 (2009).
8. J. L. Bos, H. Rehmann, A. Wittinghofer, *Cell* 129, 865 (2007).
9. F. Barr, D. G. Lambright, *Curr Opin Cell Biol* 22, 461 (2010).
10. S. M. Sebti, A. D. Hamilton, *Oncogene* 19, 6584 (2000).
11. S. F. Sousa, P. A. Fernandes, M. J. Ramos, *Curr Med Chem* 15, 1478 (2008).
12. K. M. Sane et al., *J Pharmacol Exp Ther* 333, 23 (2010).
13. S. Machida, N. Kato, K. Harada, J. Ohkanda, *J Am Chem Soc* (2010).
14. S. Fletcher et al., *J Med Chem* 53, 6867 (2010).
15. C. E. McKenna et al., *J Med Chem* 53, 3454 (2010).
16. D. Vigil, J. Cherfils, K. L. Rossman, C. J. Der, *Nat Rev Cancer* 10, 842 (2010).
17. N. Nassar, J. Cancelas, J. Zheng, D. A. Williams, Y. Zheng, *Curr Top Med Chem* 6, 1109 (2006).
18. H. E. Pelish et al., *Nat Chem Biol* 2, 39 (2006).
19. A. Shutes et al., *J Biol Chem* 282, 35666 (2007).
20. J. T. Hartmann, M. Haap, H. G. Kopp, H. P. Lipp, *Curr Drug Metab* (2009).
21. C. Progida et al., *J Cell Sci* 120, 3729 (2007).
22. P. A. Vanlandingham, B. P. Ceresa, *J Biol Chem* 284, 12110 (2009).
23. S. BasuRay, S. Mukherjee, E. Romero, M. C. Wilson, A. Wandinger-Ness, *PLoS One* 5, e15351 (2010).
24. A. de Gassart, C. Geminard, D. Hoekstra, M. Vidal, *Traffic* 5, 896 (2004).
25. K. Croizet-Berger, C. Daumerie, M. Couvreur, P. J. Courtoy, M. F. van den Hove, *Proc Natl Acad Sci USA* 99, 8277 (2002).
26. K. Roepstorff, L. Grovdal, M. Grandal, M. Lerdrup, B. van Deurs, *Histochem Cell Biol* 129, 563 (2008).
27. M. Bains, V. Zaegel, J. Mize-Berge, K. A. Heidenreich, *Neurosci Lett* 488, 112 (2011).
28. M. G. Gutierrez, D. B. Munafo, W. Beron, M. I. Colombo, *J Cell Sci* 117, 2687 (2004).
29. C. Liang et al., *Nat Cell Biol* 10, 776 (2008).
30. V. Deretic, *Curr Opin Cell Biol* 22, 252 (2010).
31. E. Wong, A. M. Cuervo, *Nat Neurosci* 13, 805 (2010).
32. L. Cogli et al., *Acta Neuropathol* 120, 491 (2010).
33. S. L. Schwartz et al., *Anal Biochem* 381, 258 (2008).
34. M. Tessema et al., *Cytometry A* 69, 326 (2006).
35. Z. Survilladze et al., *J Biomol Screen* 15, 10 (2010).
36. S. Ramirez, C. T. Aiken, B. Andrzejewski, L. A. Sklar, B. S. Edwards, *Cytometry A* 53, 55 (2003).
37. I. Simon, M. Zerial, R. S. Goody, *J Biol Chem* 271, 20470 (1996).
38. J. Giraldo, J. Serra, D. Roche, X. Rovira, *Curr Drug Targets* 8, 197 (2007).
39. Y. Feng, B. Press, A. Wandinger-Ness, *J Cell Biol* 131, 1435 (1995).
40. M. C. Manara et al., *Clin Cancer Res* 16, 530 (2010).
41. R. J. Flinn, Y. Yan, S. Goswami, P. J. Parker, J. M. Backer, *Mol Biol Cell* 21, 833 (2010).
42. X. M. Zhang, B. Walsh, C. A. Mitchell, T. Rowe, *Biochem Biophys Res Commun* 335, 154 (2005).
43. S. Seto, S. Matsumoto, K. Tsujimura, Y. Koide, *Microbiol Immunol* 54, 170 (2010).
44. M. Johansson et al., *J Cell Biol* 176, 459 (2007).
45. N. Rocha et al., *J Cell Biol* 185, 1209 (2009).
46. K. Mizuno, A. Kitamura, T. Sasaki, *Mol Biol Cell* 14, 3741 (2003).
47. J. Dong, W. Chen, A. Welford, A. Wandinger-Ness, *J Biol Chem* 279, 21334 (2004).
48. S. Mukherjee et al., *Methods Enzymol* 403, 650 (2005).

REFERENCES

Second Set of Examples

1. Colicelli, J., *Human RAS superfamily proteins and related GTPases*. Sci STKE, 2004. 2004(250): p. RE13.
2. Vigil, D., et al., *Ras superfamily GEFs and GAPs: validated and tractable targets for cancer therapy?* Nat Rev Cancer, 2010. 10(12): p. 842-57.
3. DerMardirossian, C. and G. M. Bokoch, *GDIs: central regulatory molecules in Rho GTPase activation*. Trends Cell Biol, 2005. 15(7): p. 356-63.
4. Konstantinopoulos, P. A., M. V. Karamouzis, and A. G. Papavassiliou, *Post-translational modifications and regulation of the RAS superfamily of GTPases as anticancer targets*. Nat Rev Drug Discov, 2007. 6(7): p. 541-55.
5. Shaw, R. J. and L. C. Cantley, *Ras, PI(3)K and mTOR signalling controls tumour cell growth*. Nature, 2006. 441(7092): p. 424-30.
6. Etienne-Manneville, S, and A. Hall, *Rho GTPases in cell biology*. Nature, 2002. 420(6916): p. 629-35.
7. Tybulewicz, V. L. and R. B. Henderson, *Rho family GTPases and their regulators in lymphocytes*. Nat Rev Immunol, 2009. 9(9): p. 630-44.
8. Stenmark, H., *Rab GTPases as coordinators of vesicle traffic*. Nat Rev Mol Cell Biol, 2009. 10(8): p. 513-25.
9. Agola, J., et al., *Rab GTPases as regulators of endocytosis, targets of disease and therapeutic opportunities*. Clin Genet, 2011.
10. Overmeyer, J. H. and W. A. Maltese, *Death pathways triggered by activated Ras in cancer cells*. Front Biosci, 2011. 16: p. 1693-713.
11. Sahai, E. and C. J. Marshall, *RHO-GTPases and cancer*. Nat Rev Cancer, 2002. 2(2): p. 133-42.
12. Vega, F. M. and A. J. Ridley, *Rho GTPases in cancer cell biology*. FEBS Lett, 2008. 582(14): p. 2093-101.
13. Stengel, K. and Y. Zheng, *Cdc42 in oncogenic transformation, invasion, and tumorigenesis*. Cell Signal, 2011. 23(9): p. 1415-23.
14. Hooff, G. P., et al., *Isoprenoids, small GTPases and Alzheimer's disease*. Biochim Biophys Acta, 2010. 1801(8): p. 896-905.
15. McCray, B. A., E. Skordalakes, and J. P. Taylor, *Disease mutations in Rab7 result in unregulated nucleotide exchange and inappropriate activation*. Hum Mol Genet, 2010. 19(6): p. 1033-47.
16. Cogli, L., F. Piro, and C. Bucci, *Rab7 and the CMT2B disease*. Biochem Soc Trans, 2009. 37(Pt 5): p. 1027-31.
17. BasuRay, S., et al., *Rab7 mutants associated with Charcot-Marie-Tooth disease exhibit enhanced NGF-stimulated signaling*. PLoS One, 2010. 5(12): p. e15351.
18. Schafer, W. R., et al., *Genetic and pharmacological suppression of oncogenic mutations in ras genes of yeast and humans*. Science, 1989. 245(4916): p. 379-85.
19. Sebti, S. M. and A. D. Hamilton, *Farnesyltransferase and geranylgeranyltransferase I inhibitors and cancer therapy: lessons from mechanism and bench-to-bedside translational studies*. Oncogene, 2000. 19(56): p. 6584-93.
20. Cherfils, J. and P. Melancon, *On the action of Brefeldin A on Sec7-stimulated membrane-recruitment and GDP/GTP exchange of Arf proteins*. Biochem Soc Trans, 2005. 33(Pt 4): p. 635-8.

21. Sata, M., et al., *Brefeldin A-inhibited guanine nucleotide-exchange activity of Sec7 domain from yeast Sec7 with yeast and mammalian ADP ribosylation factors.* Proc Natl Acad Sci USA, 1998. 95(8): p. 4204-8.
22. Peyroche, A., et al., *Brefeldin A acts to stabilize an abortive ARF-GDP-Sec7 domain protein complex: involvement of specific residues of the Sec7 domain.* Mol Cell, 1999. 3(3): p. 275-85.
23. Sata, M., J. Moss, and M. Vaughan, *Structural basis for the inhibitory effect of brefeldin A on guanine nucleotide-exchange proteins for ADP-ribosylation factors.* Proc Natl Acad Sci USA, 1999. 96(6): p. 2752-7.
24. Renault, L., B. Guibert, and J. Cherfils, *Structural snapshots of the mechanism and inhibition of a guanine nucleotide exchange factor.* Nature, 2003. 426(6966): p. 525-30.
25. Viaud, J., et al., *Structure-based discovery of an inhibitor of Arf activation by Sec7 domains through targeting of protein-protein complexes.* Proc Natl Acad Sci USA, 2007. 104(25): p. 10370-5.
26. Nassar, N., et al., *Structure-function based design of small molecule inhibitors targeting Rho family GTPases.* Curr Top Med Chem, 2006. 6(11): p. 1109-16.
27. Pelish, H. E., et al., *Secramine inhibits Cdc42-dependent functions in cells and Cdc42 activation in vitro.* Nat Chem Biol, 2006. 2(1): p. 39-46.
28. Shutes, A., et al., *Specificity and mechanism of action of EHT 1864, a novel small molecule inhibitor of Rac family small GTPases.* J Biol Chem, 2007. 282(49): p. 35666-78.
29. Surviladze, Z., et al., *A Potent and Selective Inhibitor of Cdc42 GTPase.* 2010.
30. Surviladze, Z., et al., *Identification of a small GTPase inhibitor using a high-throughput flow cytometry bead-based multiplex assay.* J Biomol Screen, 2010. 15(1): p. 10-20.
31. Nakano, H. and S. Omura, *Chemical biology of natural indolocarbazole products: 30 years since the discovery of staurosporine.* J Antibiot (Tokyo), 2009. 62(1): p. 17-26.
32. Gescher, A., *Analogs of staurosporine: potential anticancer drugs?* Gen Pharmacol, 1998. 31(5): p. 721-8.
33. Lapenna, S, and A. Giordano, *Cell cycle kinases as therapeutic targets for cancer.* Nat Rev Drug Discov, 2009. 8(7): p. 547-66.
34. Hill, M. M. and B. A. Hemmings, *Inhibition of protein kinase B/Akt. implications for cancer therapy.* Pharmacol Ther, 2002. 93(2-3): p. 243-51.
35. Ustun, C., D. L. DeRemer, and C. Akin, *Tyrosine kinase inhibitors in the treatment of systemic mastocytosis.* Leuk Res, 2011. 35(9): p. 1143-52.
36. Chigaev, A., et al., *Real time analysis of the affinity regulation of alpha 4-integrin. The physiologically activated receptor is intermediate in affinity between resting and Mn(2+) or antibody activation.* J Biol Chem, 2001. 276 (52): p. 48670-8.
37. Chigaev, A. and L. A. Sklar, *Overview: assays for studying integrin-dependent cell adhesion.* Methods Mol Biol, 2012. 757: p. 3-14.
38. Chigaev, A., Y. Smagley, and L. A. Sklar, *Nitric oxide/cGMP pathway signaling actively down-regulates alpha4beta1-integrin affinity: an unexpected mechanism for inducing cell de-adhesion.* BMC Immunol, 2011.12: p. 28.
39. Solubility and stability data assessment was outsourced to a data was collected by the Sanford-Burnham Institute, under the direction of Dr. Layton Smith
40. Gopinathan, S., Nouraldeen, A., Wilson, A. G. E. Development and application of a highthroughput formulation screening strategy for oral administration in drug discovery. Future Med. Chem. (2010) 2(9), 1391-1398.
41. Ibrahim F, El-Din M K, Eid M I, Wahba M E. 2011. Validated stability-indicating spectrofluorimetric methods for the determination of ebastine in pharmaceutical preparations. Chem Cent J. 5(1):11.
42. Andersen, H. S., Olsen, O. H., Iversen, L. F., Sorensen, A. L. P., Mortensen, S. B., Christensen, M. S., Branner, S., Hansen, T. K., Lau, J. F., Jeppesen, L., Moran, E. J., Su, J., Bakir, F., Judge, L., Shahbaz, M., Collins, T., Vo, T., Newman, M. J., Ripka, W. C., Moller, N. P. H. (2002) Discovery and SAR of a Novel Selective and Orally Bioavailable Nonpeptide Classical Competitive Inhibitor Class of Protein-Tyrosine Phosphatase 1B, *J. Med. Chem.* 45, 4443-4459.
43. Copeland, R. A., *Evaluation of enzyme inhibitors in drug discovery: a guide for medicinal chemists and pharmacologists.* 2005, Hoboken, N.J.: Wiley-Interscience. xvii, 271p.
44. Zella, D., et al., *Interferon-gamma increases expression of chemokine receptors CCR1, CCR3, and CCR5, but not CXCR4 in monocytoid U937 cells.* Blood, 1998. 91(12): p. 4444-50.
45. Hogg, N., I. Patzak, and F. Willenbrock, *The insider's guide to leukocyte integrin signalling and function.* Nat Rev Immunol, 2011. 11(6): p. 416-26.
46. Abram, C. L. and C. A. Lowell, *The ins and outs of leukocyte integrin signaling.* Annu Rev Immunol, 2009. 27: p. 339-62.
47. Hyun, Y. M., C. T. Lefort, and M. Kim, *Leukocyte integrins and their ligand interactions.* Immunol Res, 2009.
48. Yusuf-Makagiansar, H., et al., *Inhibition of LFA-1/ICAM-1 and VLA-4/VCAM-1 as a therapeutic approach to inflammation and autoimmune diseases.* Med Res Rev, 2002. 22(2): p. 146-67.
49. Rice, G. P., H. P. Hartung, and P. A. Calabresi, *Anti-alpha4 integrin therapy for multiple sclerosis: mechanisms and rationale.* Neurology, 2005. 64(8): p. 1336-42.
50. Chatterjee, M., et al., *Individual rac GTPases mediate aspects of prostate cancer cell and bone marrow endothelial cell interactions.* J Signal Transduct, 2011. 2011: p. 541851.
51. Laudanna, C., J. J. Campbell, and E. C. Butcher, *Role of Rho in chemoattractant-activated leukocyte adhesion through integrins.* Science, 1996. 271(5251): p. 981-3.
52. Arpaia, E., et al., *The interaction between caveolin-1 and Rho-GTPases promotes metastasis by controlling the expression of alpha5-integrin and the activation of Src, Ras and Erk.* Oncogene, 2011.
53. Rathinam, R., A. Berrier, and S. K. Alahari, *Role of Rho GTPases and their regulators in cancer progression.* Front Biosci, 2011. 17: p. 2561-71.
54. Szczur, K., Y. Zheng, and M. D. Filippi, *The small Rho GTPase Cdc42 regulates neutrophil polarity via CD11b integrin signaling.* Blood, 2009. 114(20): p. 4527-37.
55. Langereis, J. D., et al., *A 2D-DIGE approach to identify proteins involved in inside-out control of integrins.* J Proteome Res, 2009. 8(8): p. 3824-33.
56. Fernandez-Sauze, S., et al., *Regulation of fibronectin matrix assembly and capillary morphogenesis in endothelial cells by Rho family GTPases.* Exp Cell Res, 2009. 315(12): p. 2092-104.
57. Bolomini-Vittori, M., et al., *Regulation of conformer-specific activation of the integrin LFA-1 by a chemokine-triggered Rho signaling module.* Nat Immunol, 2009. 10(2): p. 185-94.

58. Ceresa, B. P., *Regulation of EGFR endocytic trafficking by rab proteins*. Histol Histopathol, 2006. 21(9): p. 987-93.
59. Barbieri, M. A., et al., *Role of rab5 in EGF receptor-mediated signal transduction*. Eur J Cell Biol, 2004. 83(6): p. 305-14.
60. Li, G., *Rab GTPases, membrane trafficking and diseases*. Curr Drug Targets, 2011. 12(8): p. 1188-93.
61. Reck, M., et al., *Erlotinib in advanced non-small cell lung cancer: efficacy and safety findings of the global phase IV Tarceva Lung Cancer Survival Treatment study*. J Thorac Oncol, 2010. 5(10): p. 1616-22.
62. Gridelli, C., et al., *Erlotinib in the treatment of non-small cell lung cancer: current status and future developments*. Anticancer Res, 2010. 30(4): p. 1301-10.
63. Bayraktar, S, and C. M. Rocha-Lima, *Advanced or metastatic pancreatic cancer: molecular targeted therapies*. Mt Sinai J Med, 2010. 77(6): p. 606-19.
64. Mountzios, G. and K. N. Syrigos, *A benefit-risk assessment of erlotinib in non-small-cell lung cancer and pancreatic cancer*. Drug Saf, 2011. 34(3): p. 175-86.
65. Catellani, S., et al., *Imatinib treatment induces CD5+ B lymphocytes and IgM natural antibodies with anti-leukemic reactivity in patients with chronic myelogenous leukemia*. PLoS One, 2011. 6(4): p. e18925.
66. Mazzeo, F., et al., *Nonadherence to imatinib treatment in patients with gastrointestinal stromal tumors: the ADAGIO study*. Anticancer Res, 2011. 31(4): p. 1407-9.
67. Jaffe, A. B. and A. Hall, *Rho GTPases: biochemistry and biology*. Annu Rev Cell Dev Biol, 2005. 21: p. 247-69.
68. Korlach, J., et al., *Spontaneous nucleotide exchange in low molecular weight GTPases by fluorescently labeled gamma-phosphate-linked GTP analogs*. Proc Natl Acad Sci USA, 2004. 101(9): p. 2800-5.
69. Schwartz, S. L., et al., *Flow cytometry for real-time measurement of guanine nucleotide binding and exchange by Ras-like GTPases*. Anal Biochem, 2008. 381(2): p. 258-66.
70. Segel, I. H., *Enzyme kinetics: behavior and analysis of rapid equilibrium and steady state enzyme systems*. 1975, New York: Wiley. xxii, 957 p.

What is claimed is:

1. A method of treating or inhibiting ovarian cancer in a patient in need thereof comprising administering to said patient an anti-cancer effective amount of a compound according to the formulae below:

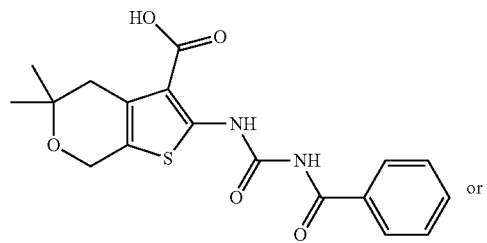 [SMILES: CC1(C)Cc2c(sc(NC(=O)NC(=O)c3ccccc3)c2C(=O)O)CO1] or

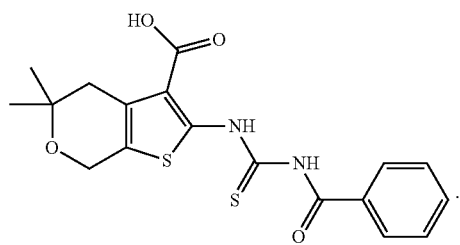 [SMILES: CC1(C)Cc2c(sc(NC(=S)NC(=O)c3ccccc3)c2C(=O)O)CO1].

2. The method according to claim 1 wherein said compound inhibits metastasis of said cancer.

3. The method according to claim 1 wherein said additional anticancer agent is cisplatin, carboplatin, paclitaxel, docetaxel, capecitabine, altretamine, etoposide, gemcitabine, ifosfamide, PEG-labeled irinotecan, doxorubicin, melphalan, pemetrexed, vinorelbine or a mixture thereof.

* * * * *